(12) United States Patent
Grissom et al.

(10) Patent No.: US 6,315,978 B1
(45) Date of Patent: Nov. 13, 2001

(54) BIOCONJUGATES AND DELIVERY OF BIOACTIVE AGENTS

(75) Inventors: Charles B. Grissom; Frederick G. West, both of Salt Lake City, UT (US); Allen W. Howard, Jr., Dexter, MI (US)

(73) Assignee: University of Utah, Research Foundation, Salt Lake City, UT (US)

( * ) Notice: Subject to any disclaimer, the term of this patent is extended or adjusted under 35 U.S.C. 154(b) by 0 days.

(21) Appl. No.: 09/202,328

(22) PCT Filed: Aug. 22, 1997

(86) PCT No.: PCT/US97/14140

§ 371 Date: Oct. 22, 1999

§ 102(e) Date: Oct. 22, 1999

(87) PCT Pub. No.: WO98/08859

PCT Pub. Date: Mar. 5, 1998

Related U.S. Application Data

(60) Provisional application No. 60/024,430, filed on Aug. 27, 1996, and provisional application No. 60/025,036, filed on Aug. 27, 1996.

(51) Int. Cl.⁷ .......................... A61K 51/00; A61K 49/00; A61K 39/385; A61B 5/055; A01N 61/00

(52) U.S. Cl. ................... 424/1.53; 424/1.11; 424/9.361; 424/193.1; 514/1; 514/2; 514/4; 514/6; 514/44

(58) Field of Search .................................. 424/1.11, 9.1, 424/9.322, 9.34, 9.361, 9.362, 193.1, 194.1, 1.53, 155.1, 131; 514/2, 4, 6, 12, 44, 1; 530/300, 402

(56) References Cited

U.S. PATENT DOCUMENTS

| | | | |
|---|---|---|---|
| 4,758,421 | * | 7/1988 | Goodwin et al. ............... 424/1.1 |
| 5,047,227 | * | 9/1991 | Rodwell et al. ................ 424/1.1 |
| 5,428,023 | * | 6/1995 | Russell-Jones et al. ......... 514/21 |
| 5,512,443 | | 4/1996 | Schlom et al. ................ 435/7.23 |
| 5,589,463 | | 12/1996 | Russell-Jones et al. ......... 514/21 |
| 5,608,046 | | 3/1997 | Cook et al. .................. 536/23.1 |
| 5,763,569 | * | 8/1998 | Brown et al. .................. 530/324 |

FOREIGN PATENT DOCUMENTS

| | | | |
|---|---|---|---|
| 95/27723 | * | 10/1995 | (WO) . |
| WO95/27723 | * | 10/1995 | (WO) . |

OTHER PUBLICATIONS

Volipin, M. et al. 1996. Agnew Chem. Int. Ed. Engl. vol 35 (20) pp. 2395–2396, 1996.*
Marzilli, L.G. et al 1987. J. Am. Chem. Soc. vol. 109, pp. 6045–6052, 1987.*
Mandal, S.S. et al. 1997 Bioconj. Chem. vol. 8(6): pp. 798–812, 1997.*
Osinsky, S.P. et al. 1997. Anticancer Res. vol 17, pp. 3457–3462, 1997.*
Routier, S. et al. 1998 J. Chem. Soc., Perkin Trans. 2 pp. 863–868, 1998.*
Grissom et al. Zeitschrift fur Physikalische Chemie, Bd. vol. 182, pp. 181–188, 1993.*
Natarajan et al. Abstracts of Papers of the American Chemical Society, vol. 213, No. 2, p. 17–INOR, 1996.*
Crooke, S.T. Antisense Research and Application, Chapter 1, pp. 1–50, published by Springer–Verlag, 1998.*
Schofield et al. Brit. Med. Bull, vol. 51, No. 1, pp. 56–71, 1995.*
Branch, A.D. Trends in Biochem. Sci., vol. 23, pp. 45–50, 1998.*
Friedmann, T. Scientific American, June vol., pp. 96–101, 1997.*
Verma et al. Nature, vol. 389, pp. 239–242, 1997.*
Crystal, R.G. Science, vol. 270, pp. 404–410, 1995.*
Hogenkamp et al. Chemistry and Biochemistry of B12, Edited by Ruma Banerjee, Chapter 15, Diagnostic and Therapeutic Analogues of Cobalamin, pp. 386–410, published by John Wiley and Sons, Inc., 1999.*
Russell–Jones, G.J., et al. "Vitamin $B_{12}$ Mediated Oral Delivery Systems for Granulocyte–Colony Stimulating Factor and Erythropoietin", *Bioconjugate Chem.*, 1995; 6:459–465.

* cited by examiner

*Primary Examiner*—Andrew Wang
*Assistant Examiner*—Jane Zara
(74) *Attorney, Agent, or Firm*—Rothwell, Figg, Ernst & Manbeck

(57) ABSTRACT

The present invention relates to bioconjugates and the delivery of bioactive agents which are preferably targeted for site-specific release in cells, tissues or organs. More particularly, this invention relates to bioconjugates which comprise of bioactive agent and an organocobalt complex. The bioactive agent is covalently bonded directly or indirectly to the cobalt atom of the organocobalt complex. The bioactive agent is released from the bioconjugate by the cleavage of the covalent bond between the bioactive agent and the cobalt atom in the organocobalt complex. The cleavage may occur as a result of normal displacement by cellular nucleophiles or enzymatic action, but is preferably caused to occur selectively at a predetermined release site by application of an external signal. The external signal may be light or photoexcitation, i.e. photolysis, or it may be ultrasound, i.e. sonolysis. Further, if the photolysis takes places in the presence of a magnetic field surrounding the release site, the release of the bioactive agent into surrounding healthy tissue is minimized.

28 Claims, 9 Drawing Sheets

BIOCONJUGATES AND DELIVERY OF BIOACTIVE AGENTS

This application claims benefit under 35 U.S.C. 119(e) provisional application Nos. 60/024,430, filed Aug. 27, 1996 and 60/025,036, filed Aug. 27, 1996.

This invention was made in part with Government support under Grant No. ES05728 awarded by the National Institutes of Health, Bethesda, Md. The United States Government has certain rights in the invention.

BACKGROUND OF THE INVENTION

The present invention relates to bioconjugates and the delivery of bioactive agents which are preferably targeted for site-specific release in cells, tissues or organs. More particularly, this invention relates to bioconjugates which comprise a bioactive agent and an organocobalt complex. The bioactive agent is covalently bonded directly or indirectly to the cobalt atom of the organocobalt complex. The bioactive agent is released from the bioconjugate by the cleavage of the covalent bond between the bioactive agent and the cobalt atom in the organocobalt complex. The cleavage may occur as a result of normal displacement by cellular nucleophiles or enzymatic action, but is preferably caused to occur selectively at a predetermined release site by application of an external signal. The external signal may be light or photoexcitation, i.e. photolysis, or it may be ultrasound, i.e. sonolysis. Further, if the photolysis takes place in the presence of a magnetic field surrounding the release site, the release of the bioactive agent into surrounding healthy tissue is minimized.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The focus of a substantial body of research has been the development of a system whereby a pharmaceutical agent can be selectively delivered to a desired anatomic location; namely the site in need of treatment. In spite of the great progress which has been achieved in this regard, many pharmaceutical delivery systems for the treatment of various diseases or health risks, e.g., the treatment of cancer, impart substantial risk to the patient. With respect to the treatment of cancer, drugs which are effective in attacking malignant cells to destroy them, or at least limit their proliferation, have a tendency to attack benign cells also. Therefore, it is highly desirable to limit the location of their action to that of the malignancy, and to ensure that at any particular time effective, but not excessive, amounts of such drugs are used.

Although it is desired to concentrate a cytotoxic agent at a targeted site, current cancer treatment protocols for administering these cytotoxic agents typically call for repeated intravenous dosing, with careful monitoring of the patient. The drugs are often used in combination to exert a multi-faceted assault on neoplastic cells. The dose is selected to be just below the amount that will produce acute (and sometimes chronic) toxicity that can lead to life-threatening cardiomyopathy, myelotoxicity, hepatic toxicity, or renal toxicity. Alopecia (hair loss), mucositis, stomatitis, and nausea are other common, but generally not life-threatening, side effects at these doses. Since many of these compounds are potent vesicants, tissue necrosis will occur if localized extravasation (loss of the drug from blood to the surrounding tissue) occurs. These effects occur since the blood generally attains a specified concentration of that drug before becoming effective. Because the blood is transported throughout the body of the host being treated, so is the pharmaceutical agent. Following this technique provides an even distribution of the drug throughout the body, rather than concentrating it at the treatment site. Moreover, such systemic treatment methods expose the healthy cells to the cytotoxic agent concurrent with the treatment of the unhealthy or diseased cells besides limiting the concentration of the drug at the site where it is most needed.

Previous attempts to administer such drugs by direct injection into the location of the organ having the malignancy are only partially effective, because of migration of the drug from that location and as a result of extensive tissue necrosis from extravasation. Such dispersion cannot be totally prevented, with the result that excessive quantities of drug need to be administered to attain a desired result. Although careful clinical monitoring may prevent extensive damage or loss of viable tissue, the providing of a pharmaceutical agent-carrier system which is actively transported through standard biological systems to the treatment site prior to activation of the pharmaceutical agent would be highly desirable not only in optimizing, utilization of the drug but also in the reduction of side effects and/or the minimization of the destruction of healthy cells. The direct injection of cytotoxic agents into solid tumors of the breast, bladder, prostate and lung using conventional cytotoxic chemotherapeutic agents as adjuvants to surgery and/or radiotherapy has been of limited success in prolonging the lives of patients. This is partially due to the dose limitations imposed by the acute and chronic toxicity to tissues or organ systems beyond those that are targeted.

As it relates to the administration of cytotoxic or antineoplastic drugs, the effective resolution of concerns relating to modes of administration, to the limitation of dosage size and frequency of administration, and to side effects would certainly be of benefit to the treatment of cancer.

Oligonucleotides that specifically interfere with gene expression at the transcriptional or translational levels have the potential to be used as therapeutic agents to control the synthesis of deleterious proteins associated with viral, neoplastic or other diseases. It is possible to select single-stranded oligonucleotides that recognize and bind to the major groove of a stretch of double-stranded DNA in a sequence-specific manner to form a triple helix (Le Doan et al., 1987; Moser and Dervan, 1987). Triple helix-forming oligonucleotides targeted to the promoter region of certain genes have been used to physically block RNA synthesis in cell-free transcription assays (Cooney et al., 1988; Postel et al., 1992; Skoog et al., 1993; Rando et al., 1994). Similarly, in vitro translation assays have been used to demonstrate that antisense oligonucleotides can bind mRNA targets and prevent protein synthesis (Uhlmann and Peyman, 1990; Cohen and Hogan, 1994).

Although antisense oligonucleotides have shown great efficacy in the selective inhibition of gene expression (Stein and Cohen, 1988; Szczylik et al., 1991; Gray et al., 1993), the therapeutic applications of such antisense oligonucleotides are currently limited by their low physiological stability, slow cellular uptake, and lack of tissue specificity. The instability obstacles have been largely overcome by use of backbone-modified oligonucleotides that are more resistant to nucleases. Methylphosphonates, protein-nucleic acid conjugates, and phosphorothioates all appear to resist enzymatic digestion better than the corresponding natural oligonucleotides (Chang and Miller, 1991; Wickstrom et al., 1992; Letsinger, 1993; Zon, 1993).

Problems with cellular uptake of antisense oligonucleotides have been more difficult to solve. Endogenous uptake pathways that rely on pinocytosis and related processes generally have insufficient capacity to deliver the quantities of antisense of oligonucleotides required to suppress gene expression (Vlassov et al., 1994). Hydrophobic modifications have also been undertaken to improve membrane permeability, but such derivatization strategies are most useful only for short oligonucleotides (Vlassov et al., 1994). Although complexes of antisense constructs with cationic liposomes or immunoliposomes (Gao and Huang, 1991; Bennett et al., 1992, Ma and Wei, 1996) and polylsine (Trubetskoy et al., 1992; Bunnell et al., 1992) have significantly enhanced intracellular delivery, they have simultaneously introduced new disadvantages of their own. Thus, both methods exhibit some carrier cytotoxicity, and like other protocols, neither strategy allows for any tissue or cell targeting. In short, intracellular delivery and tissue specificity remain major obstacles to the implementation of antisense drugs in the treatment of human disorders.

Other techniques for the delivery of oligonucleotides to cells include the use of: (a) folate-PEG-liposome constructs for the delivery of antisense DNA against growth factor receptor (Wang et al., 1995); (b) folic acid-polylysine constructs for the delivery of c-myc antisense DNA (Ginobbi et al., (1997); (c) tris(N-acetylgalactosamine aminohexyl glycoside) amide of tyrosyl(glutamyl)-glutamate (YEE (GalNAcAH)$_3$) linked to polylysine for the delivery of DNA to cells via the asialoglycoprotein receptor (Merwin et al., 1994); and (d) water-soluble block polycations (Kabanov et al., 1995).

It has been known for some time that a pharmaceutically active agent can be attached to a carrier or molecule. The term "prodrug" is often associated with such systems wherein the active agent is bonded to another molecule for purposes of administration. The drug is usually inactive in the prodrug state and the bond is later cleaved releasing the drug at a site where it can be effective. However, such systems are not as useful as might be desired for various reasons, site specificity being one. Also, the release of the drug from its carrier requires the presence of some agent or event to separate the active drug from its carrier or molecule and, as such, may rely on factors such as the presence of a specific enzyme, pH conditions, time release and the like, which may be variable from host to host and which may not be effectively implemented.

For example, transmembrane transport of nutrient molecules is a critical cellular function. Because practitioners have recognized the importance of transmembrane transport to many areas of medical and biological science, including drug therapy, peptide therapy and gene transfer, there have been significant research efforts directed to the understanding and application of such processes. Thus, for example, transmembrane delivery of nucleic acids has been encouraged through the use of protein carriers, antibody carriers, liposomal delivery systems, electroporation, direct injection, cell fusion, vital carriers, osmotic shock, and calcium-phosphate mediated transformation. However, many of those techniques are limited both by the types of cells in which transmembrane transport is enabled and by the conditions of use for successful transmembrane transport of exogenous molecular species. Further, many of these known techniques are limited in the type and size of exogenous molecule that can be transported across a membrane without loss of bioactivity.

One method for transmembrane delivery of exogenous molecules having a wide applicability is based on the mechanism of receptor-mediated endocytotic activity. Unlike many other methods, receptor-mediated endocytotic activity can be used successfully both in vivo and in vitro. Receptor-mediated endocytosis involves the movement of ligands bound to membrane receptors into the interior of an area bounded by the membrane through invagination of the membrane. The process is initiated or activated by the binding of a receptor-specific ligand to the receptor. Many receptor-mediated endocytotic systems have been characterized, including those recognizing galactose, mannose, mannose 6-phosphate, transferrin, asialoglycoprotein, transcobalamin (Vitamin B$_{12}$), α-2-macroglobulins, insulin, and other peptide growth factors such as epidermal growth factor (EGF).

Receptor-mediated endocytotic activity has been utilized for delivering exogenous molecules such as proteins and nucleic acids to cells. Generally, a specified ligand is chemically conjugated by covalent, ionic or hydrogen bonding to an exogenous molecule of interest (i.e. the exogenous compound), forming a conjugate molecule having a moiety (the ligand portion) that is still recognized in the conjugate by a target receptor. Using this technique, the phototoxic agent psoralen has been conjugated to insulin and internalized by the insulin receptor endocytotic pathway (Gasparro, 1986); the hepatocyte-specific receptor for galactose terminal asialoglycoproteins has been utilized for the hepatocyte-specific transmembrane delivery of asialoorosomucoid-poly-L-lysine non-covalently complexed to a DNA plasmid (Wu, 1987); the cell receptor for epidermal growth factor has been utilized to deliver polynucleotides covalently linked to EGF to the cell interior (Myers, 1988); the intestinally situated cellular receptor for the organometallic Vitamin B$_{12}$-intrinsic factor complex has been used to mediate delivery to the circulatory system of a vertebrate host a drug, hormone, bioactive peptide or immunogen complexed with Vitamin B$_{12}$ and delivered to the intestine through oral administration (Russell-Jones et al., 1995); the mannose-6-phosphate receptor has been used to deliver low density lipoproteins to cells (Murray and Neville, 1980); the cholera toxin binding subunit receptor has been used to deliver insulin to cells lacking insulin receptors (Roth and Maddox, 1983); the human chorionic gonadotropin receptor has been employed to deliver a ricin a-chain coupled to HCG to cells with the appropriate HCG receptor in order to kill the cells (Oeltmann and Heath, 1979); the transferrin receptor has been used to deliver mitomycin C to sarcoma cells (Tanaka et al., 1996) or to deliver doxorubicin to multidrug-resistant cells (Fritzer et al., 1996); the biotin receptor has been employed to deliver hypoxanthine-guanine phosphoribosyl transferase (HGPRT) by biotinylating the HGPRT to restore growth to HGPRT deficient cells (Low et al., 1995); and the folic acid receptor has been used to deliver antisense DNA to src-transformed fibroblast cells (Low et al., 1995).

Russell-Jones et al. (1995), describes a system which involves the formation of a covalent bond between the pharmaceutical agent one wishes to deliver and a modified Vitamin B$_{12}$ to form a conjugate molecule. The conjugate is orally administered and is then transported from the intestinal lumen to the circulation. Importantly, the pharmaceutical agent and the vitamin are bound through an amide linkage which is prone to acid hydrolysis. Russell-Jones et al. found that many biologically active pharmaceutical agents can be bound to B$_{12}$ for facilitating the introduction of the drug into the blood stream through oral administration. Importantly, no method was provided whereby the drug-B$_{12}$ bond could be selectively cleaved, nor could location of the active pharmaceutical agent be controlled once activated. Instead, Russell-Jones et al. relied on biochemical degradation of the drug-$B_{12}$ bond to release the drug in its active form. Importantly, under this method the drug could be released in its active form anywhere within the circulation system, diminishing the importance of the active transport of $B_{12}$ into cancer tissue. Moreover, the conjugates formed under this method require the modification of the structure of the corrin ring of the $B_{12}$ molecule, which modification can have serious effects on receptor interactions.

Thus, there exists a need for a drug delivery system which can be utilized for the delivery of bioactive agents, including pharmaceuticals, peptides and oligonucleotides. There is also a need for a drug delivery system which can be used for site-specific release of the bioactive agent in the cells, tissues, or organs in which a therapeutical effect is desired to be effected.

SUMMARY OF THE INVENTION

The present invention relates to bioconjugates and the delivery of bioactive agents which are preferably targeted for site specific release in cells, tissues or organs. More particularly, this invention relates to bioconjugates which comprise a bioactive agent and an organocobalt complex. The bioactive agent is covalently bonded directly or indirectly to the cobalt atom of the organocobalt complex. The bioactive agent is released from the bioconjugate by the cleavage of the covalent bond between the bioactive agent and the cobalt atom in the organocobalt complex, as described herein.

The bioactive agent is any agent which is desired to be delivered to cells, tissues or organs for nutrient or therapeutic effects. In accordance with the present invention, bioactive agents include, but are not limited to, nutrients, pharmaceuticals, drugs, peptides and oligonucleotides.

The organocobalt complex is any organic complex containing a cobalt atom having bound thereto 4–5 -nitrogen and/or chalcogens such as oxygen, sulfur, etc., as part of a multiple unsaturated heterocyclic ring system. In accordance with the present invention, suitable organocobalt complexes include, but are not limited to, cobalamin, Co[SALEN], organo-(pyridine)bis(dimethylglyoximato)cobalt, corrinoids, derivatives thereof and analogues thereof. The organocobalt complexes may be unsubstituted or substituted with conventional organic functional groups which will not alter the basic nature of the organocobalt complex. The basic nature of the organocobalt complex is to directly or indirectly bind the bioactive agent covalently to the cobalt such that the cobalt-bioactive agent bond is readily cleavable as described herein. The organocobalt complex may also be covalently bound directly or indirectly to a targeting molecule. The targeting molecule is a molecule for which the desired cell, tissue or organ has a requirement or a receptor, as described herein.

The bioconjugate according to the present invention is administered to a subject in need of therapeutic treatment. The bioconjugate concentrates in a targeted cell, tissue or organ site as a result of the organocobalt complex. As an example, a bioconjugate containing a chemotherapeutic is administered to a patient and the bioconjugate concentrates in neoplastic cells where the active chemotherapeutic is released from the bioconjugate by cleavage. Similarly, other pharmaceuticals, drugs, peptides or oligonucleotides are administered to a subject as part of the bioconjugate which is concentrated in the desired cells, tissues or organs. The pharmaceuticals, drugs, peptides or oligonucleotides are released by cleavage. In one embodiment, the cleavage may occur as a result of normal displacement by cellular nucleophiles or enzymatic action. In a second embodiment, the cleavage is caused to occur selectively at the release site by an external signal. The external signal may be light or photoexcitation, i.e. photolysis, or it may be ultrasound, i.e. sonolysis. Further, if the photolysis takes place in the presence of a magnetic field surrounding the release site, the release of the drug, such as a cytotoxic agent, into surrounding healthy tissue can be minimized.

DETAILED DESCRIPTION OF THE INVENTION

Figure 1:
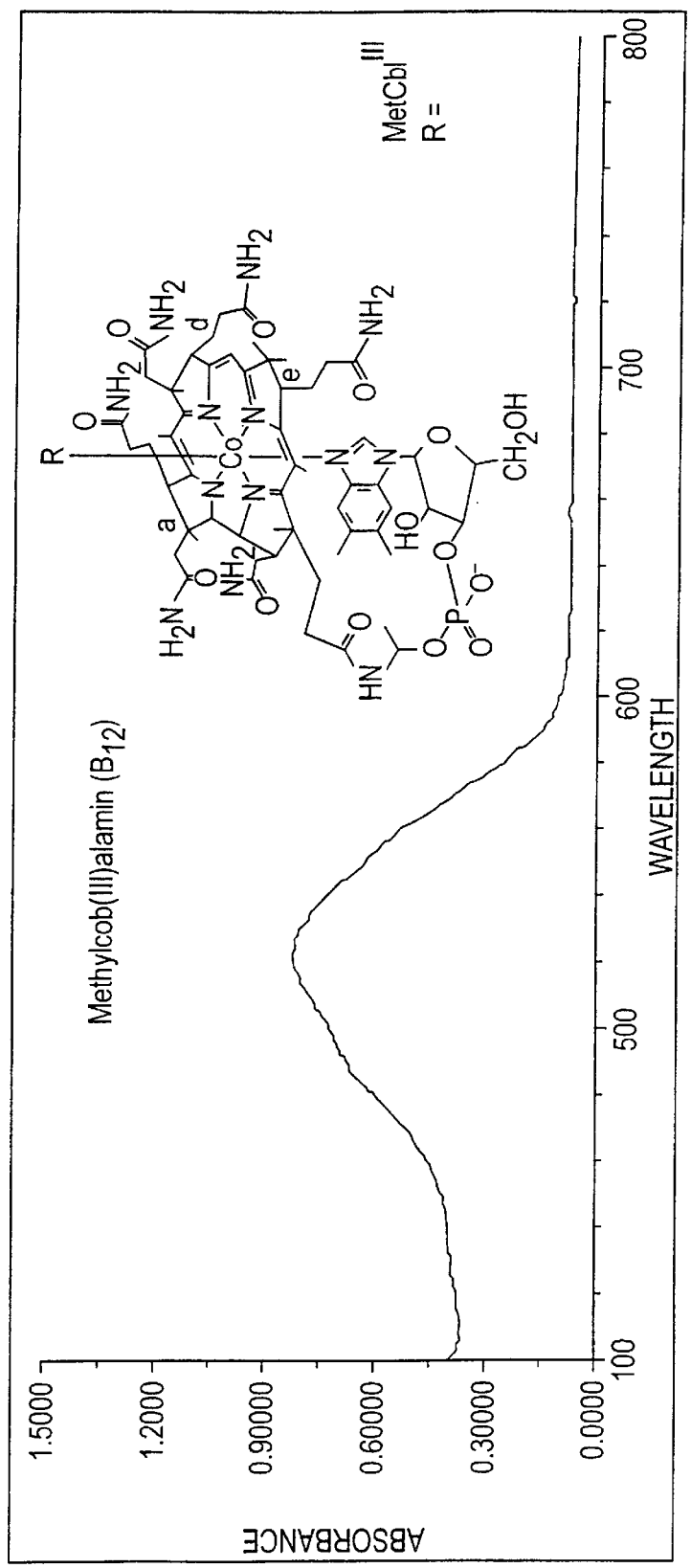
FIG. 1 shows the structure and absorption spectrum of methylcobalamin ($B_{12}$).

The present invention relates to bioconjugates and the delivery of bioactive agents which are preferably targeted for site-specific release in cells, tissues or organs. More particularly, this invention relates to bioconjugates which comprise a bioactive agent and an organocobalt complex. The bioactive agent is covalently bonded directly or indirectly to the cobalt atom of the organocobalt complex. The bioactive agent is released from the bioconjugate by the cleavage of the covalent bond between the bioactive agent and the cobalt atom in the organocobalt complex. The cleavage may occur as a result of normal displacement by cellular nucleophiles or enzymatic action, but is preferably caused to occur selectively at a predetermined release site by application of an external signal. The external signal may be light or photoexcitation, i.e. photolysis, or it may be ultrasound, i.e. sonolysis. Further, if the photolysis takes place in the presence of a magnetic field surrounding the release site, the release of the bioactive agent into surrounding healthy tissue is minimized.

The bioconjugate according to the present invention is administered to a subject in need of therapeutic treatment. The bioconjugate concentrates in a targeted cell, tissue or organ site as a result of the organocobalt complex. The bioactive agent is released from the bioconjugate by cleavage. In one embodiment, the cleavage may occur as a result of normal displacement by cellular nucleophiles or enzymatic action. In a second embodiment, the cleavage is caused to occur selectively at the release site by an external signal. The external signal may be light or photoexcitation, i.e. photolysis, or it may be ultrasound, i.e. sonolysis. Further, if the photolysis takes place in the presence of a magnetic field surrounding the release site, the release of the drug, such as a cytotoxic agent, into surrounding healthy tissue is minimized.

As one example, the bioconjugate contains a chemotherapeutic agent and is administered to a patient having cancer. In this example, a therapeutically effective amount of the bioconjugate is administered intravenously to a patient such that the bioconjugate concentrates in the neoplastic cells. The chemotherapeutic agent is released from the bioconjugate by natural means (e.g., cellular nucleophiles or enzymatic action) or preferably by means of an external signal (e.g., light or ultrasound).

As a second example, the bioconjugate contains a cytotoxic agent and is administered to a patient having psoriasis. In this example, a therapeutically effective amount of the bioconjugate is administered to an afflicted skin site. The cytotoxic agent is released by natural means or preferably by means of an external signal.

As a third example, the bioconjugate contains the enzymatic domain of diphtheria toxin (Nichols et al., 1997) and is administered to a patient having cancer. In this example, a therapeutically effective amount of the bioconjugate is administered intravenously to a patient such that the bioconjugate concentrates in the neoplastic cells. The enzymatic domain of diphtheria toxin is released from the bioconjugate by natural means (e.g., cellular nucleophiles or enzymatic action) or preferably by means of an external signal (e.g., light or ultrasound) and proceeds to kill the cancer cells.

As a fourth example, the bioconjugate contains an antisense oligonucleotide against hepatitis B virus (Yao et al., 1996; Madon and Blum, 1996) and is administered to a subject having hepatitis B. In this example, a therapeutically effective amount of the bioconjugate is administered intravenously to a patient such that the bioconjugate concentrates in the liver. The antisense oligonucleotide is released from the bioconjugate by natural means (e.g., cellular nucleophiles or enzymatic action) or preferably by means of an external signal (e.g., light or ultrasound) and proceeds to inhibit gene expression and replication of hepatitis B virus.

The present invention employs the following definitions:

Bioactive agent: any agent which is desired to be delivered to cells, tissues or organs for modulating or otherwise modifying cell function, including for therapeutic effects. In accordance with the present invention, bioactive agents include, but are not limited to, pharmaceutically active compounds or diagnostic compounds. Bioactive agents include, but are not limited to, peptides, oligopeptides, proteins, apoproteins, glycoproteins, antigens and antibodies or antibody fragments thereto, receptors and other membrane proteins, retro-inverso oligopeptides, protein analogs in which at least one non-peptide linkage replaces a peptide linkage, enzymes, coenzymes, enzyme inhibitors, amino acids and their derivatives, hormones, lipids, phospholipids, liposomes, ricin or ricin fragments; toxins such as aflatoxin, digoxin, xanthotoxin, rubratoxin; antibiotics such as cephalosporins, penicillin and erythromycin; analgesics such as aspirin, ibuprofen and acetaminophen, bronchodilators such as theophylline and albuterol; beta-blockers such as propranolol, metoprolol, atenolol, labetolol, timolol, penbutolol and pindolol; antimicrobial agents such as those described above and ciprofloxacin, cinoxacin and norfloxacin; antihypertensive agents such as clonidine, methyldopa, prazosin, verapamil, nifedipine, aptopril and enalapril; cardiovascular agents including antiarrhythmics, cardiac glycosides, antianginals and vasodilators, central nervous system agents including stimulants, psychotropics, antimanics and depressants; antiviral agents; antihistamines such as chlorpheniramine and brompheniramine; cancer drugs including chemotherapeutic agents, such as chlorambucil, carboplatin, derivatives of busulfan, doxorubicin, etoposide, topotecan (TPT); tranquilizers such as diazepam, chordiazepoxide, oxazepam, alprazolam and triazolam, antidepressants such as fluoxetine, amitriptyline, nortriptyline and imipramine; H-2 antagonists such as nizatidine, cimetidine, famotidine and ranitidine, anticonvulsants; antinauseants; prostaglandins; muscle relaxants; antiinflammatory substances; stimulants; decongestants; antiemetics; diuretics; antispasmodics; antiasthmatiics; anti-Parkinson agents; expectorants; cough suppressants, mucolytics; vitamins; and mineral and nutritional additives. Other molecules include nucleotides; oligonucleotides; polynucleotides; and their art-recognized and biologically functional analogs and derivatives including, for example, methylated polynucleotides and nucleotide analogs having phosphorothioate linkages; plasmids, cosmids, artificial chromosomes, other nucleic acid vectors; antisense polynucleotides including those substantially complementary to at least one endogenous nucleic acid or those having sequences with a sense opposed to at least portions of selected viral or retroviral genomes; promoters; enhancers; inhibitors; other ligands for regulating gene transcription and translation. In addition, the bioactive agent can be any other biologically active molecule that can form a conjugate with an organocobalt complex. The bioactive agent may further contain a spacer which provides a covalent bond with the cobalt atom of the organocobalt complex, but which does not adversely affect the biological activity of the bioactive agent.

Bioconjugate: a conjugate containing a bioactive agent and an organocobalt complex in which the bioactive agent is covalently bound directly to the cobalt atom or is covalently bound indirectly to the cobalt atom via a spacer.

Non-reactive atom: an atom in the bioactive agent that will not lead to rearrangement or destruction of the bioactive agent under conditions of ligand exchange during receptor-mediated endocytosis, but that instead will reproduce the original form of the bioactive agent (or bioactive agent and spacer) and thereby unmask an active bioactive agent. The non-reactive atom may be a carbon atom, a nitrogen atom, an oxygen atom, a sulfur atom, a selenium atom or a silicon atom. A carbon atom (e.g. from an alkyl, acyl or aryl group) is particularly preferred. Such non-reactive atoms are also used in forming the covalent bond between the cobalt and the spacer.

Organocobalt complex: an organic complex containing a cobalt atom having bound thereto 4–5 calcogens as part of a multiple unsaturated heterocyclic ring system. In accordance with the present invention, suitable organocobalt complexes include, but are not limited to, cobalamin (coenzyme $B_{12}$), Co[SALEN] (which is a cobalamin analogue), organo (pyridine)-bis(dimethylglyoximato) cobalt, corrinoids (such as disclosed by Brown et al., 1996) and derivatives or analogues of any of the preceding, as well as pharmaceutically acceptable salts. The organocobalt complexes may be unsubstituted or substituted with conventional organic functional groups which will not alter the basic nature of the organocobalt complex. The basic nature of the organocobalt complex is to bind the bioactive agent covalently to the cobalt such that the cobalt-bioactive agent bond is readily cleavable as described herein. Examples of substituents which may be found on the organocobalt complex include amino, nitro, halogen (bromine, chlorine), sulfito, $C_{2-6}$-alkene and $C_{2-6}$ alkyne. For example, the organocobalt complex, can be formed having a nitro and/or halo (e.g., bromo) derivative of the corrin ring or having an extended conjugation with exocyclic olefin or alkylene groups. Other derivatives include cobalamin lactone, cobalamin lactame and those in which the benzimidiazole ring (e.g., of cobalamin, green corrinoid, and the like) are substituted with e.g., one or more halogen (bromine, chlorine), hydroxy or $C_{1-6}$ alkyl. Such substituents are useful for increasing the $\lambda_{max}$ to be used for cleavage of the bioconjugate as described herein. Further derivatives include anilide, ethylamide, mono-, di- or tri-carboxylic acid or proprionamide derivatives of cobalamin of Vitamin $B_{12}$. In one embodiment, the organocobalt complex is any organic complex, containing cobalt which is bound by transcobalamin and transported into a cell by a receptor-mediated process involving transcobalamin. In a second embodiment, the organocobalt complex, may also be covalently bound directly or indirectly (through a spacer) to a targeting molecule, wherein said targeting molecule is bound by its receptor and the complex is transported into a cell by a receptor-mediated process. Co[SALEN] and its derivatives or analogues can be represented by the general formula

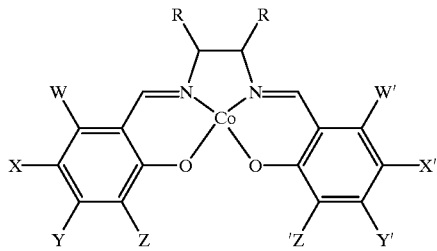

wherein the substituents may be included or omitted to modulate physical properties of the molecule, e.g., water solubility, stability or $\lambda_{max}$—the wavelength at which the complex absorbs. Thus, the substituents are as follows: R is H, a group which increases water solubility and/or stability or a group for attachment of a targeting molecule and W, W', X, X', Y, Y', Z and Z'are independently H, a group which increases water solubility and/or stability, a group for attachment of a targeting molecule or a group for modified absorbance of energy, or W and X together and W' and X' together are a 4–6 member cyclic or heterocyclic ring, or Y and Z together and Y' and Z' together are a 4–6 member cyclic or heterocyclic aromatic ring. Examples of groups for enhancing water solubility include amino, $C_{1-6}$ alcohol, $C_{1-6}$ carboxyl for any substituent, or also $SO_3$— for the substituents other than R. Examples of groups for attachment of a targeting molecule include amino, $C_{1-6}$ alcohol and $C_{1-6}$ carboxyl for any substituent. Examples of groups for modifying absorbance include $CH_2OH$, $CO_2H$, $SO_3$—, amino and nitro for the substituents other than R. Such groups are useful for increasing the wavelength of light to be used for cleavage of the bioconjugate as described herein, while targeting molecules are useful in selectively targeting the bioconjugate to the desired tissue. Therefore, when used in the context of the present application, the term organocobalt complex, unless specifically identified, shall be inclusive of $B_{12}$ in all its embodiments, including coenzyme $B_{12}$, Co[SALEN] and other $B_{12}$ or $B_{12}$-like molecules, the organocobalt complexes defined herein, as well as any derivatives and analogues thereof.

Spacer: an atom or molecule which covalently binds together two components. In the present invention, a spacer is intended to include atoms and molecules which can be used to covalently bind a bioactive agent to the cobalt atom of an organocobalt complex or to covalently bind a targeting molecule to an organocobalt complex. The spacer must not prevent the binding of the organocobalt complex or the targeting molecule with its appropriate receptor. Examples of suitable spacers include, but are not limited to, polymethylene [—$(CH_2)_n$, where n is 1–10], ester [bioactive agent attached to O and Co to C=O], carbonate, ether, acetal or any combination of two or more of these units. A skilled artisan will readily recognize other spacers which can be used in accordance with the present invention.

Several of these spacers are useful as a "self-destructing" linker group. That is, some or all of the linkage would be consumed in a fragmentation reaction. This means that, following cleavage of the C—Co bond by photolysis or sonolysis, an additional cleavage will take place several bonds away, leading to the formation of a small, unsaturated (and typically volatile) molecule made up of atoms of the former linker. This is shown schematically below:

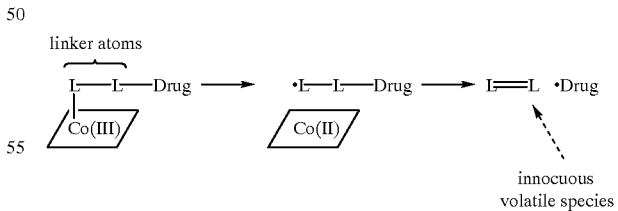

The most typical scenario is the subsequent cleavage of a second bond, two bonds removed from the first. Thus, most self-destructive linkers would contain a two-atom unit whose extrusion as a small, gaseous molecule is favorable. Another design feature is to have the new radical species which is generated after the second cleavage step be an especially stable kind of radical. Examples of self-destructing linkers are shown below:

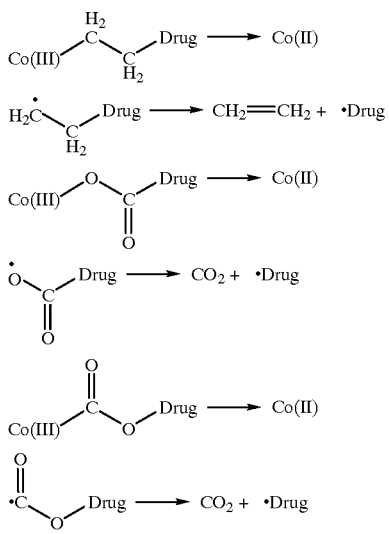

Targeting Molecule: a molecule which is bound by a receptor and transported into a cell by a receptor-mediated process. Examples of suitable targeting molecules include, but are not limited to, glucose, galactose, mannose, mannose 6-phosphate, transferrin. asialoglycoprotein, α-2-macroglobulins, insulin, a peptide growth factor, cobalamin, folic acid or derivatives, biotin or derivatives, YEE (GalNAcAH)$_3$ or derivatives, albumin, texaphyrin, metallotexaphyrin, porphyrin, any vitamin, any coenzyme, an antibody, an antibody fragment (e.g., Fab) and a single chain antibody variable region (scFv). A skilled artisan will readily recognize other targeting molecules (ligands) which bind to cell receptors and which are transported into a cell by a receptor-mediated process. The present invention is intended to include all such targeting molecules.

The present invention takes advantage of the cellular properties of cobalamin and cobalamin analogues or derivatives, as well as the cellular properties of other targeting molecules. For example, studies have shown that the absorption of physiological amounts of vitamin $B_{12}$ by the gut requires that it be complexed with a naturally occurring transport protein known as intrinsic factor (IF). (Castle, 1953; Fox and Castle, Allen and Majerus. 1972b). This protein is released into the lumen of the stomach by parietal cells in the fundus. Once bound to intrinsic factor, the $B_{12}$-IF complex interacts with a membrane bound receptor for IF located on the terminal ileum of the small intestine. The receptor-IF-$B_{12}$ complex is then internalized by a process of receptor-mediated endocytosis (RME). Allen and Majerus demonstrated that it is possible to chemically modify $B_{12}$, couple it to a resin and use the $B_{12}$-resin to affinity purify IF (Allen and Majerus, 1972a). This finding suggests the possibility of coupling a large macromolecule (such as the resin used by Allen and Majerus, 1972a) to $B_{12}$ while still preserving its ability to interact specifically with intrinsic factor and thus be part of the active transport system. By coupling molecules to $B_{12}$ in such a way as to preserve the ability of $B_{12}$ to interact with intrinsic factor, it was found that the natural uptake mechanism for orally administered $B_{12}$ could be used to deliver various proteins, drugs or other pharmaceutically active molecules from the intestinal lumen to the circulation. It has been found that $B_{12}$ is naturally concentrated in cancer tissue through a similar transport mechanism.

In mammals, $B_{12}$ is transported in the blood by transcobalamin proteins TC-I, TC-II, and TC-III. The major form of $B_{12}$ in the blood is methylcobalamin and the largest store of $B_{12}$ is adenosylcobalamin in the liver. Rapidly dividing cells, including cancer cells, require coenzyme $B_{12}$ for thymidine production during DNA synthesis. It has been reported by Carmel (1975) that, in some patients with tumors, up to 50-fold increases in the major cobalamin transport proteins TC-I and TC-II have been observed. Waxman et al. (1972), report the finding of tumor specific $B_{12}$ binding proteins that circulate in the blood. In each instance, these increases in TC transport proteins and the corresponding systemic depletion of $B_{12}$ were not the result of megaloblastosis, granulocyte proliferation, or any other pathogenic $B_{12}$ deficiency.

In a second example of receptor-mediated endocytosis, folate receptors that mediate endocytotic activity have previously been identified in bacterial cells (Kumar et al., 1987) and used for delivery of biologically active materials (Low et al., 1995). Folic acid, folinic acid, pteropolyglutamic acid, and folate receptor-binding pteridines such as tetrahydropterins, dihydrofolates, tetrahydrofolates and their deaza and dideaza analogs are useful as targeting molecules in accordance with the present invention. The terms "deaza" and "dideaza" analogs refer to the art-recognized analogs having a carbon atom substituted for one or two nitrogen atoms in the naturally-occurring folic acid structure. For example, the deaza analogs include the 1-deaza, 3-deaza, 5-deaza, 8-deaza, and 10-deaza analogs. The dideaza analogs include, for example, 1,5-dideaza, 5,10-dideaza, 8,10-dideaza, and 5,8-dideaza analogs. The foregoing folic acid derivatives are conventionally termed "folates," reflecting their capacity to bind with folate-receptors, and such ligands when complexed with exogenous molecules are effective to enhance trans-membrane transport. Other folates useful as complex forming ligands for this invention are the folate receptor binding analogs aminopterin, amethopterin (methotrexate), $N^{10}$-methylfolate, 2-deaminohydroxyfolate, deaza analogs such as 1-deazamethopterin or 3-deazamethopterin, and 3'5'-dichloro4-amino-4-deoxy-$N^{10}$-methylpteroyl-glutamic acid (dichloromethotrexate). Other suitable ligands capable of binding to folate receptors to initiate receptor-mediated endocytotic transport of the complex include anti-idiotypic antibodies to the folate receptor. An exogenous molecule in complex with an anti-idiotypic antibody to a folate receptor is used to trigger trans-membrane transport of the complex. Such molecules are used in accordance with the present invention as a targeting molecule.

In a further example of receptor-mediated endocytosis, biotin receptors have been used to mediate endocytotic activity (Low et al., 1995). Biotin analogs such as biocytin, biotin sulfoxide, oxybiotin and other biotin receptor-binding compounds are ligands that may also be used as suitable targeting molecules to promote the trans-membrane transport of exogenous molecules in accordance with this invention. Other compounds capable of binding to biotin receptors to initiate receptor-mediated endocytotic transport of the complex are also contemplated. These can include other receptor-binding ligands such as, for example, anti-idiotypic antibodies to the biotin receptor. An exogenous molecule complexed with an anti-idiotypic antibody to a biotin receptor could be used to trigger trans-membrane transport of the complex. Such molecules are used in accordance with the present invention as a targeting molecule.

Other examples of targeting molecules include glucose, galactose, mannose, mannose 6-phosphate, hormones (e.g., insulin, growth hormone, and the like), growth factors or cyokines (e.g., TGF-βEGF, insulin-like growth factor, and the like), YEE(GalNAcAH)$_3$ or derivatives, cobalamin, α-2 macroglobulins, asialoglycoprotein, albumin, texaphyrin, metallotexaphyrin, antibodies, antibody fragments (e.g., Fab), single-chain antibody variable region (scFv), transferrin, any vitamin and any coenzyme.

As previously described, a bioconjugate of the present invention comprises a bioactive agent conjugated directly or indirectly via a covalent bond to the cobalt atom of an organocobalt complex. The bioactive agent is conjugated directly to the cobalt atom through a non-reactive atom in the bioactive agent or is conjugated indirectly to the cobalt atom through the use of a spacer. Therefore, in contrast to the conjugates formed under U.S. Pat. No. 5,428,023, the attachment of a bioactive agent to the cobalt atom in the axial position does not interfere with receptor-mediated endocytosis from the blood into cells.

The unusually weak cobalt-non-reactive atom bond (e.g., C—Co bond) of the bioconjugate provides a readily addressable trigger for the controlled in vivo release of the bioactive agent from the organocobalt complex. The bond dissociation energy (BDE) of Co-non-reactive atom bond in the bioconjugate is in the range of 30 to 50 kcal/mol (e.g., 30–40 kcal/mol range for a Co—C bond) which make them among the weakest covalent bonds known, yet the bond is relatively stable in aqueous solution.

A common strategy will employ the modification of the anticancer drug so that it possesses an electrophilic site which can react with the highly nucleophilic Co(I) intermediate generated upon treatment of hydroxycobalamin with NaBH$_4$. This structural modification will be sufficiently far removed from the active site (pharmacophore) to preclude any interference with the desired biological activity. Approaches used in the case of chlorambucil are typical: the carboxylic acid group of chlorambucil is converted to either an acid chloride or a bromoethyl ester, either of which can be efficiently coupled with cob(I)alamin.

General Strategy

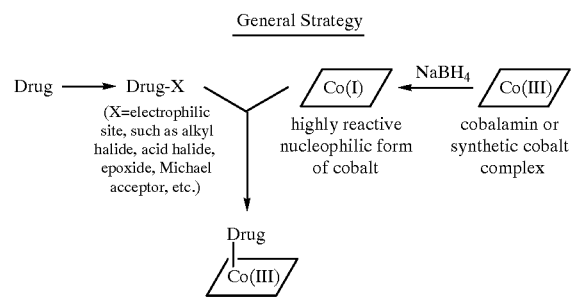

For example, reduced Cbl$^1$ is prepared by NaBH$_4$ or zinc dust reduction, e.g. of hydroxo-cob(III)alamin. In the above scheme, the drug can be a cytotoxic agent, other drug or other bioactive agent as described herein. In other schemes, a spacer containing a carbon atom or other atom such as that specified for the non-reactive atom for binding to the cobalt atom and which also contains a reactive grouping, e.g. —OH or —CN, which is further reacted with the bioactive agent, is introduced. Other reactive groups, e.g. —NH$_2$, —SH, —COOH, etc., can also be utilized for coupling to a bioactive agent. It is important to note that, in some cases (e.g., chlorambucil, doxorubicin), the small organic molecule released is not the parent drug, but rather retains some of the modification installed to allow coupling. In other cases (e.g., topotecan), the structure of the released drug may correspond to the parent molecule.

More specific details of the synthesis of representative bioconjugates according to the present invention are as follows, using a "drug" which can be replaced by any suitable bioactive agent and cobalamin which can be replaced by any suitable organocobalt complex. In this synthesis, all procedures are under argon. Hydroxocob(III) alamin is dissolved in aqueous CH$_3$OH(1:1 v/v) at 25° C. A 2–10 fold excess of NaBH$_4$ is added. The solution slowly changes color from red to brown and gradually green (Cbl$^1$). After approximately 15 min. the electrophilic drug ligand (dissolved in the same deoxygenated solvent) is added, e.g., as an alkyl, acyl or aryl chloride. Strictly anaerobic conditions are maintained and the reaction mixture is stirred gently at 25° C. The color gradually changes back to red as Cb$^1$ is converted to alkyl-, acyl-, or aryl-Cbl$^{III}$. After about 1.5 h, the solution is acidified to pH 3.0 with dilute HCl. Methanol is removed under reduced pressure by rotary evaporation at less than 40° C. The resulting aqueous solution is diluted with an equal volume of H$_2$O and loaded onto a Dowex AG-50-X2 (200–400 mesh) cation exchange column. The column is washed sequentially with H$_2$O and 0.1 M NaOAc, pH 6.4. Fractions containing drug-cob(III) alamins appear red and are collected appropriately. Unreacted hydroxocob(III)alamin is retained on the column. Combined fractions of drug-cob(III)alamin are extracted with phenol and concentrated by rotary evaporation. Drug-cob(III)alamins can often be crystallized by the addition of acetone to a concentrated aqueous solution. Characterization of the alkyl-, acyl-, or aryl-cobalamin conjugates is by NMR, mass spectrometry (FAB, Cl, or electrospray), and IR methods.

A methotrexate-containing bioconjugate can be synthesized by the following methods.

In method one utilizing the above procedure, methotrexate (MIX) is converted to its corresponding acyl chloride and reacted with cobalamin and/or Co(III)[SALEN] and/or other disclosed organocobalt complexes to yield methotrexate-cobalamin and methotrexate-Co(III)[SALEN] according to the following reaction scheme I. In the alternative method two, the C—Co bond is first formed from an acyl chloride having a protected amino group. The amino group is then deprotected, followed by formation of the amide bond to an aminobenzoylpterin according to the following reaction scheme II.

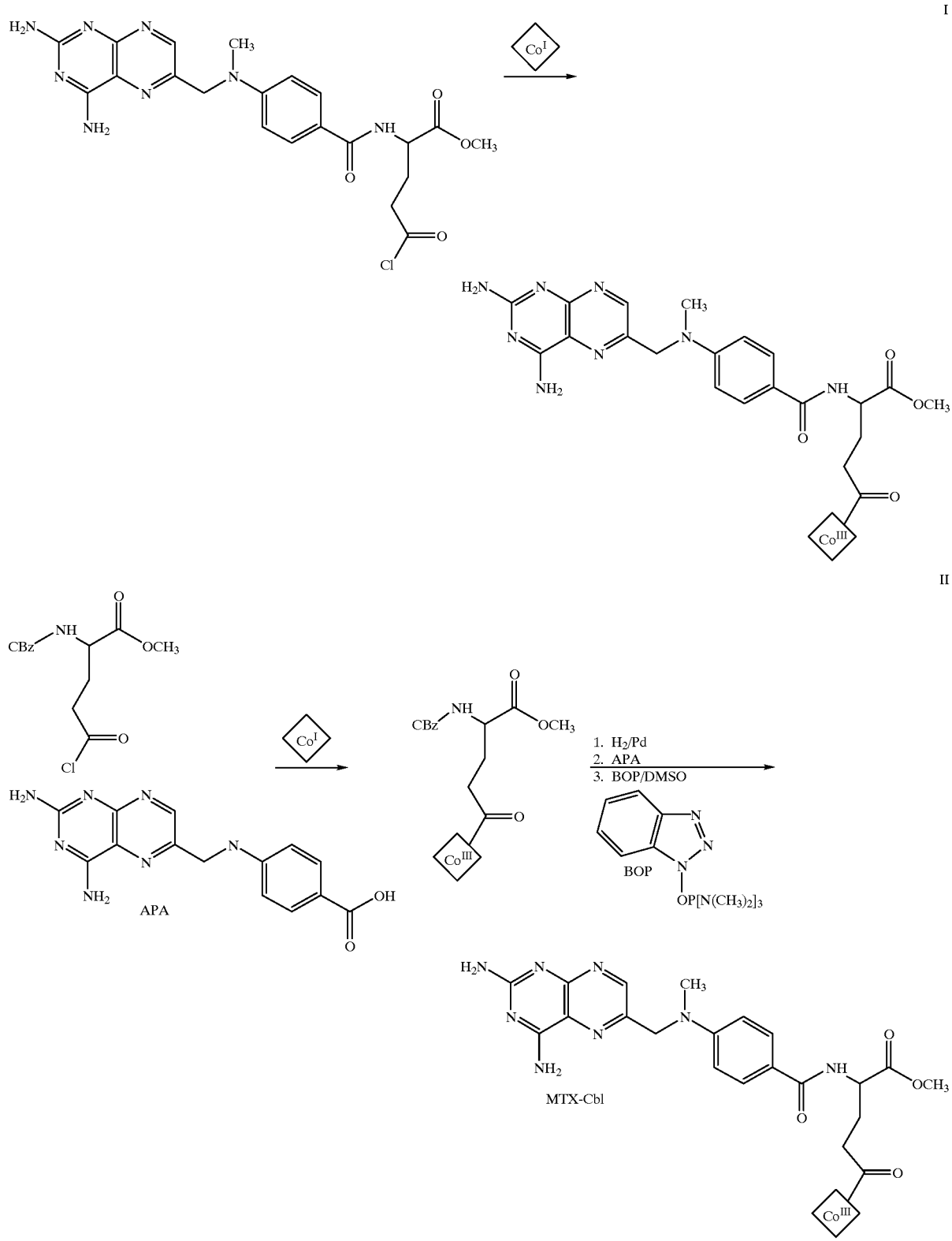

An aminopterin-containing bioconjugate can be synthesized by the following method. The des-methyl derivative of methotrexate (aminopterin) is coupled to cobalt as shown by the following reaction formula, in which the iminium ion is either reacted with Co(I) directly, or the iminium ion is converted to the aminonitrile and then slowly unmasked to reveal the iminium cation.

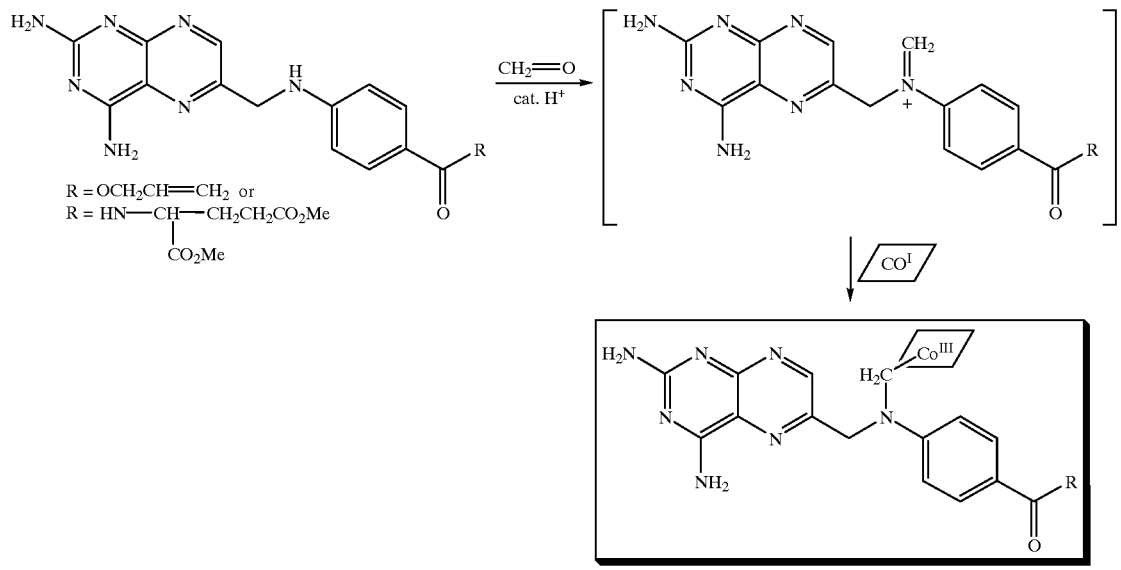

A topotecan-containing bioconjugate can be synthesized by the following method. The cytotoxic activity of topotecan (TPT) or camptothecin (CPT) arises from their ability to freeze topoisomerase I-DNA "cleavable complexes." (Pommier et al., 1995) Since some tumor types display greatly elevated levels of topo I (Giovanella et al., 1989), topoisomerase poisons of this type are likely to have a higher therapeutic index in the treatment of those cancers. However, treatment with camptothecin derivatives could be made more general if used in conjunction with the targeted delivery approach.

Topotecan is conjugated to cobalamin, Co[SALEN] and other organocobalt complexes according to the following reaction schemes. Camptothecin is conjugated in a similar manner. Preparation of 10a and 10b involves similar chemistry to that discussed above for 8a,b. Selective generation of the phenyl chloroformate (25) of topotecan (5) and acylation of Co(I) gives 10a. Exposure of 25 to 18 or treatment of 5 with the previously discussed chloroformate 19 furnishes 10b. Conjugates 10c,d will require somewhat longer routes, as they cannot be prepared directly from 5. However, the established synthetic route for conversion of the natural product camptothecin to 5 can be modified at the appropriate point to allow for attachment of the cobalt complex. The first three steps to prepare phenolic intermediate 26 are known (Mulliez et al., 1994). Mannich-type substitution with formaldehyde/dimethylamine then gives 5. Use of methylamine gives the corresponding secondary amine 27. At this point, linkage to Co via a methylene to give 10c is possible via Co(I) trapping of a second, in situ generated imminum salt. Alternatively, N-alkylation with 23 gives 10d. Cleavage of 10a and 10b provides 5 directly via fragmentative pathway or indirectly via other products. Cleavage of 10c with hydrogen extraction yields 5. Cleavage of 10d yields the product 5 having an ethylmethylamino group in place of the dimethylamino group.

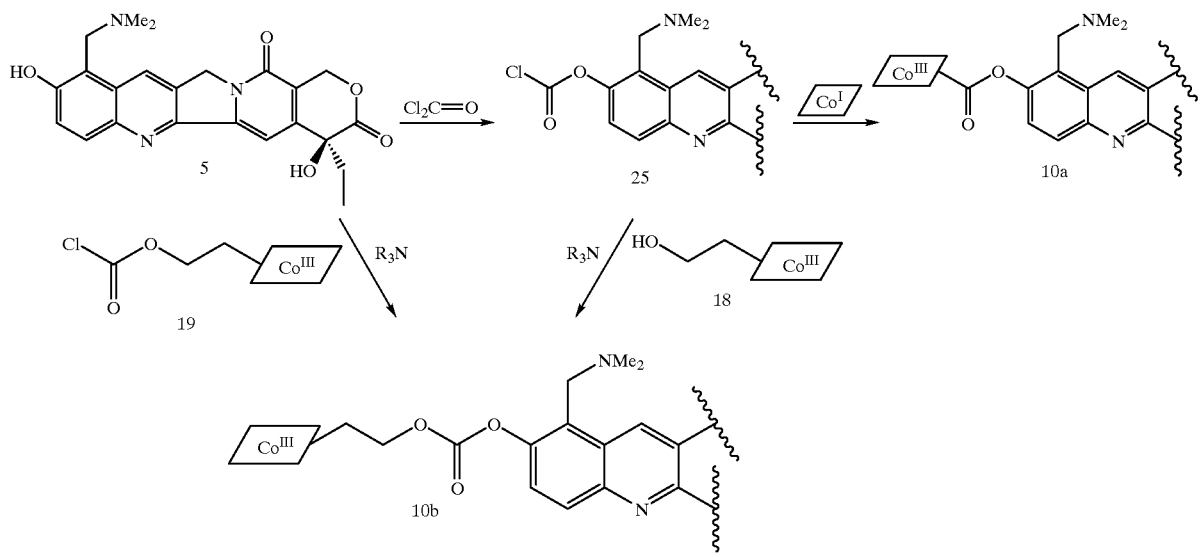

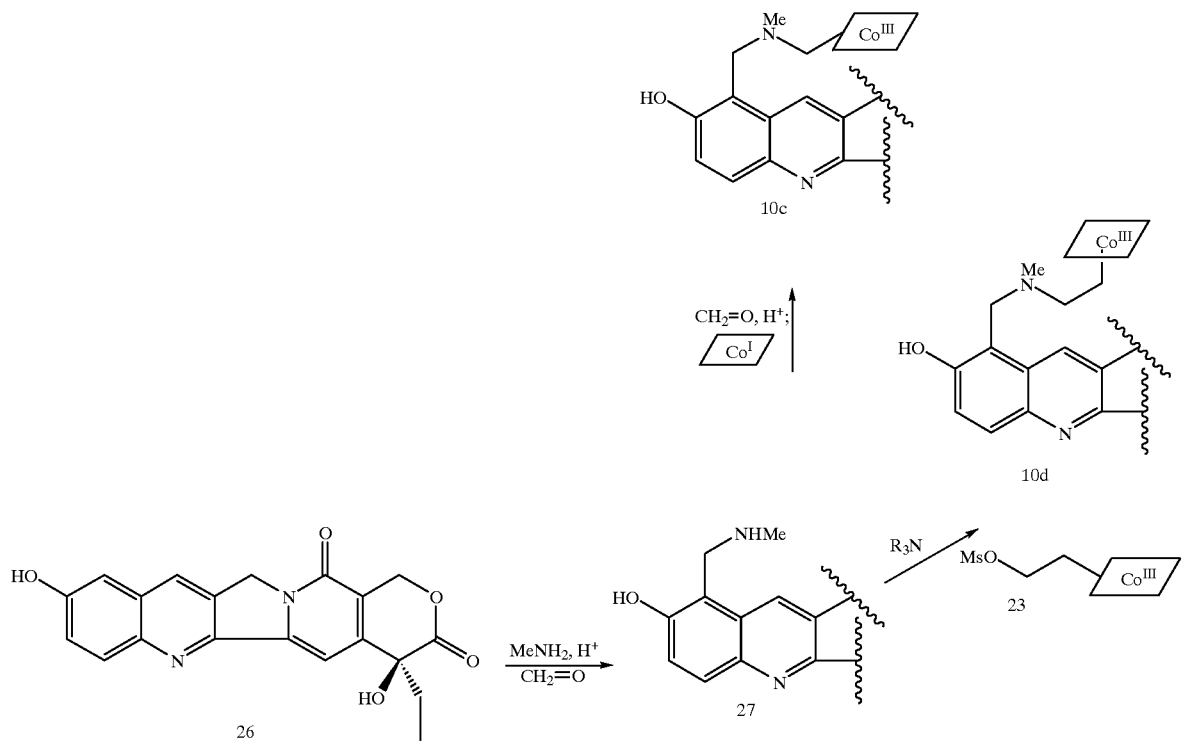

A busulfan-containing bioconjugate can be synthesized by the following method. Busulfan is an alkylating agent used therapeutically against chronic myelogenous leukemia (CML). The preferred point for attaching busulfan to the organocobalt complex, is on one of the alkanesulfonate units. A slight change in the structure of the sulfonate portion of the ester is will not exert a large effect on the ability of the released drug to crosslink DNA. Cleavage of 7a followed by hydrogen abstraction furnishes the mixed ethanesulfonate/methanesulfonate 2b. Trapping of the carbon radical under oxidative conditions produces mixed bis(sulfonate) 2c, which is also a competent crosslinking agent. Cleavage of 7b results in the release of the parent drug 2a after hydrogen abstraction.

Bis-methylsulfonate busulfan is conjugated to cobalamin, Co[SALEN] and other organocobalt complexes according to the following reaction schemes. For the preparation of 7a, the commercially available sodium salt of bromoethanesulfonic acid (11) serves as the starting point. Heating with phosphorus pentachloride furnishes the corresponding sulfonyl chloride 12 as a distillable liquid. Treatment with Co(I) leads to preferential displacement of the bromide to furnish 13, which is converted to 7a by sequential treatment with 1,4-butanediol and mesyl chloride. The order of the final three steps can be changed; for example, treatment of 12 with excess butanediol, followed by mesyl chloride gives the mixed bis(sulfonate) 14. Selective displacement of the primary bromide by Co(I) then gives 7a. In the case of conjugate 7b, treatment of 2-bromobutane-1,4-diol (which is readily available from malic acid diester) with Co(I) gives adduct 15. Bis(mesylation) gives 7b. Alternatively, 7b is prepared from 16 (X=Br or I) with selective displacement of the halide.

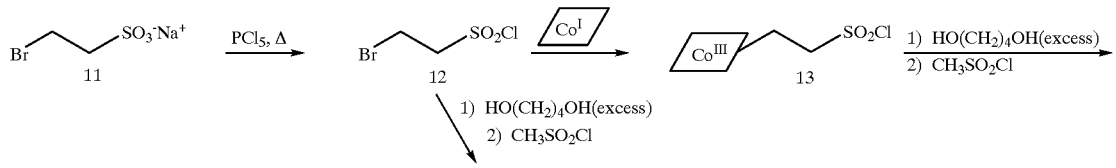

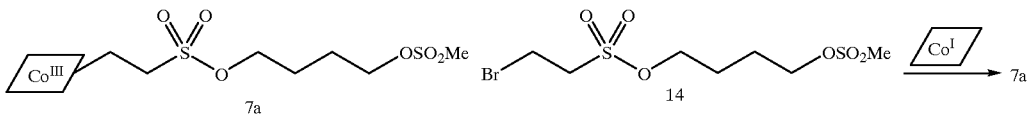

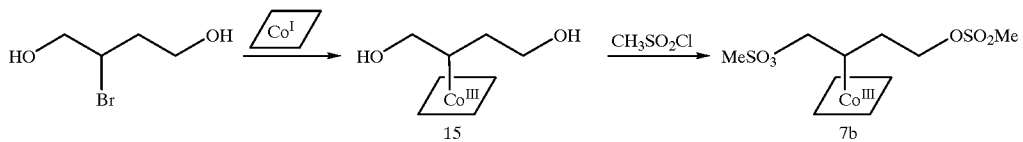

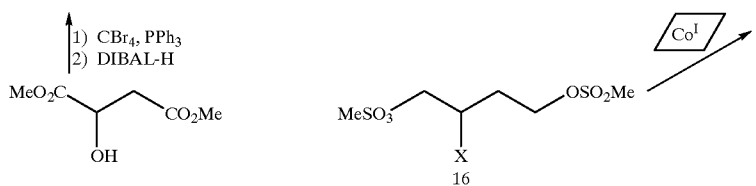

A chlorambucil-containing bioconjugate can be synthesized by the following methods. Chlorambucil is a relatively stable nitrogen mustard with attenuated alkylating ability, presumably as a consequence of the less-basic aniline nitrogen.

Method One: In this procedure, chlorambucil is converted to the acid chloride followed by reaction with cob(I)alamin or Co(I)[SALEN] according to reaction sequence I. In situations where the acyl linkage to the organocobalt complex is too labile towards serum nucleophiles, two alternate bioconjugation procedures can be utilized.

Method Two: The procedure involves bromination of a carbon atom adjacent to the carboxyl group under standard Hell-Vollhardt-Zelinski conditions to permit attachment of the Co complex in the α-position according to reaction sequence II. In scheme II, replacement of the C—Co with C—H provides chlorambucil. The reactant stoichiometry, temperature, and dilutions conditions can be manipulated to avoid competing displacement of one of the chloroethyl groups, or of the Cl by $S_N2$ attack.

Method Three: The BOC-protected p-aminophenylacetaldehyde can be conjugated to the Co moiety, followed by formation of the active nitrogen mustard product according to the following reaction sequence III.

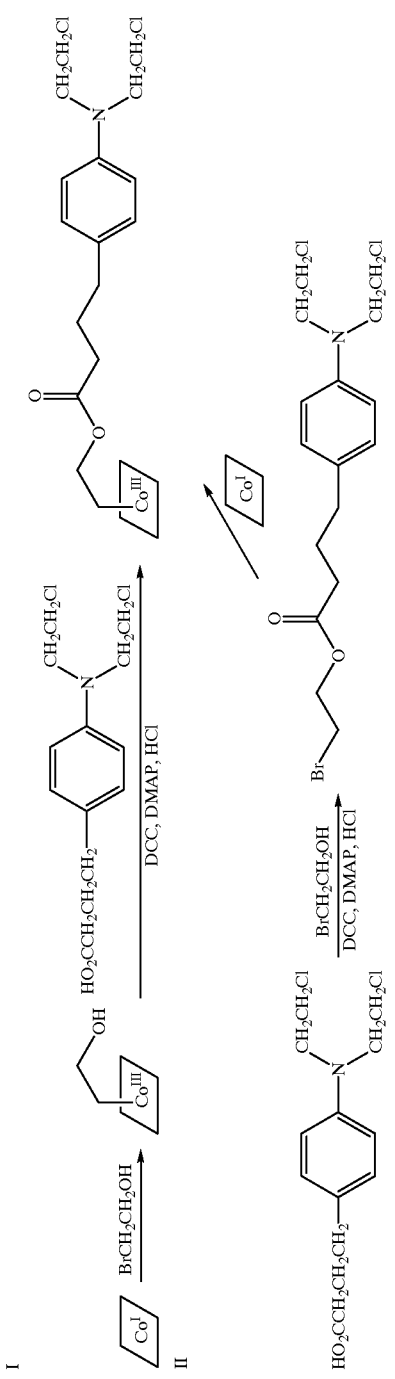
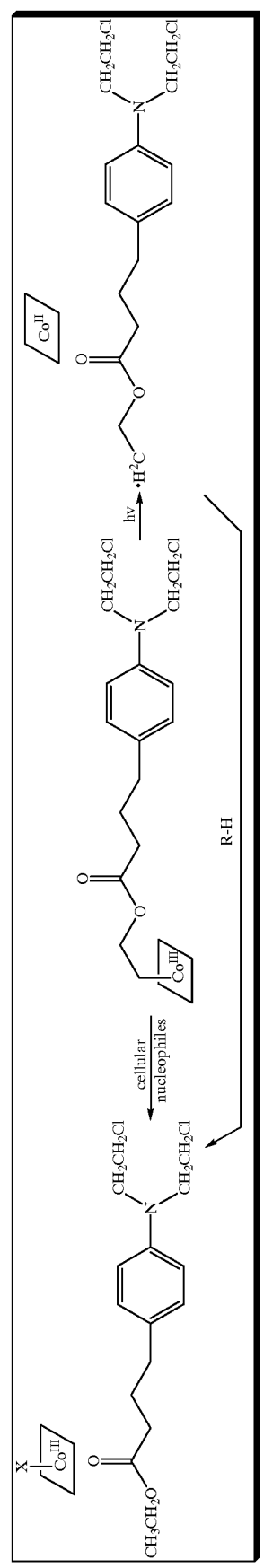

A chlorambucil, ethyl ester-containing bioconjugate can be synthesized by the following methods. When conjugating a drug via a carboxyl group, as in the case of chlorambucil, linking the drug to the cobalamin via a hydroxyethyl tether may be desirable. This can be accomplished by one of two convenient routes, both of which are schematically illustrated below. First, 2-hydroxyethyl-cob(III)alamin can be readily prepared from cob(I)alamin and bromoethanol. Esterification is carried out under standard conditions, i.e. by reaction of a carboxylic acid (chlorambucil) with an alcohol (2-hydroxyethylcob(III)alamin) in the presence of dicyclohexylcarbodiimide (DCC) (or water-soluble derivatives such as EDCI) and a catalytic amount of 4-N,N-dimethylaminopyridine (DMAP) and its hydrochloride salt (DMAP-HCl) in dichloromethane or toluene. Alternatively, the ester-linked conjugate can be prepared by first forming the 2-bromoethyl ester of chlorambucil and then reacting the ester with cob(I)alamin to provide the same product. The reaction schemes (I, II) are shown below. With this mode of attachment, cleavage from the bioconjugate leads to release of the ethyl ester of chlorambucil according to reaction scheme III.

lung carcinoma and germ cell tumors (De Jong et al., 1995). It has also shown considerable promise in the treatment of refractory cases of ovarian and breast cancer. Etoposide appears to function as a topoisomerase II poison.

Etoposide is conjugated to cobalamin, Co[SALEN] and other organocobalt complexes according to the following reaction schemes. Bioconjugates 8a and 8b require conversion of the free phenol of etoposide (3) to the corresponding chloroformate 17. Direct acylation with Co(I) gives acyl-Co(III) derivative 8a, while treatment with the previously described hydroxyethylCo(III) derivative 18 furnishes carbonate 8b. This derivative is also available via acylation of 3 with the chloroformate 19 derived from 18. Preparation of acetal-modified conjugate 8c may be more challenging. The ethylene acetal of 3 can be hydrolyzed and then the acetal reformed using aldehyde 20a or dimethyl acetal 20b (Keller-Jusl et al., 1971). Compound 20a may also be accessed via careful, selective oxidation of 18. while 20b should be available via alkylation of the Co(I) derivative with commercially available bromoacetaldehyde dimethyl acetal. In addition, the acetal of glucose can be formed and then the secondary alcohol of 21 can be glucosylated. Cleavage of 8a

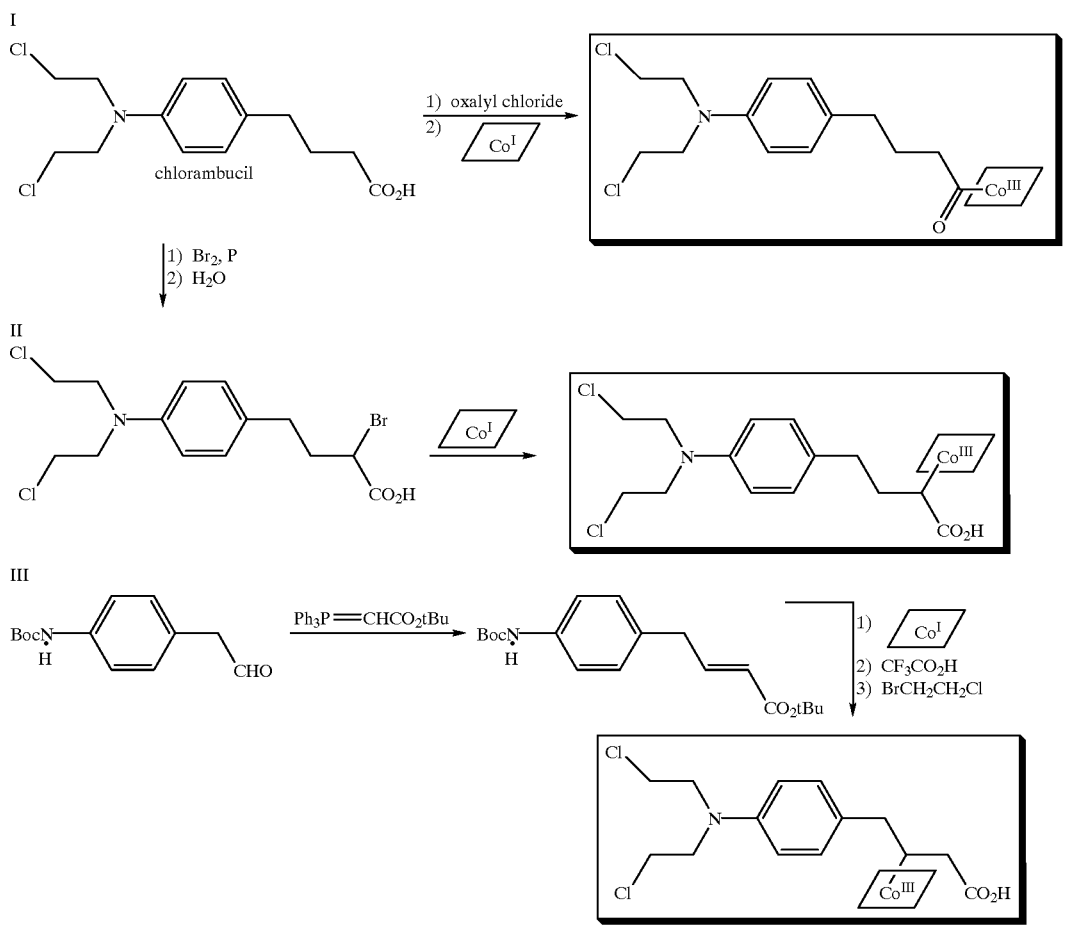

An etoposide-containing bioconjugate can be synthesized by the following method. Etoposide is a semisynthetic derivative of the natural product epipodophyllotoxin that is widely used against a variety of tumors especially small cell or 8b either give 3 directly via fragmentative pathways, or furnish products which can undergo eventual hydrolysis to 3. Trapping with H. following homolysis of 8c would then furnish 3.

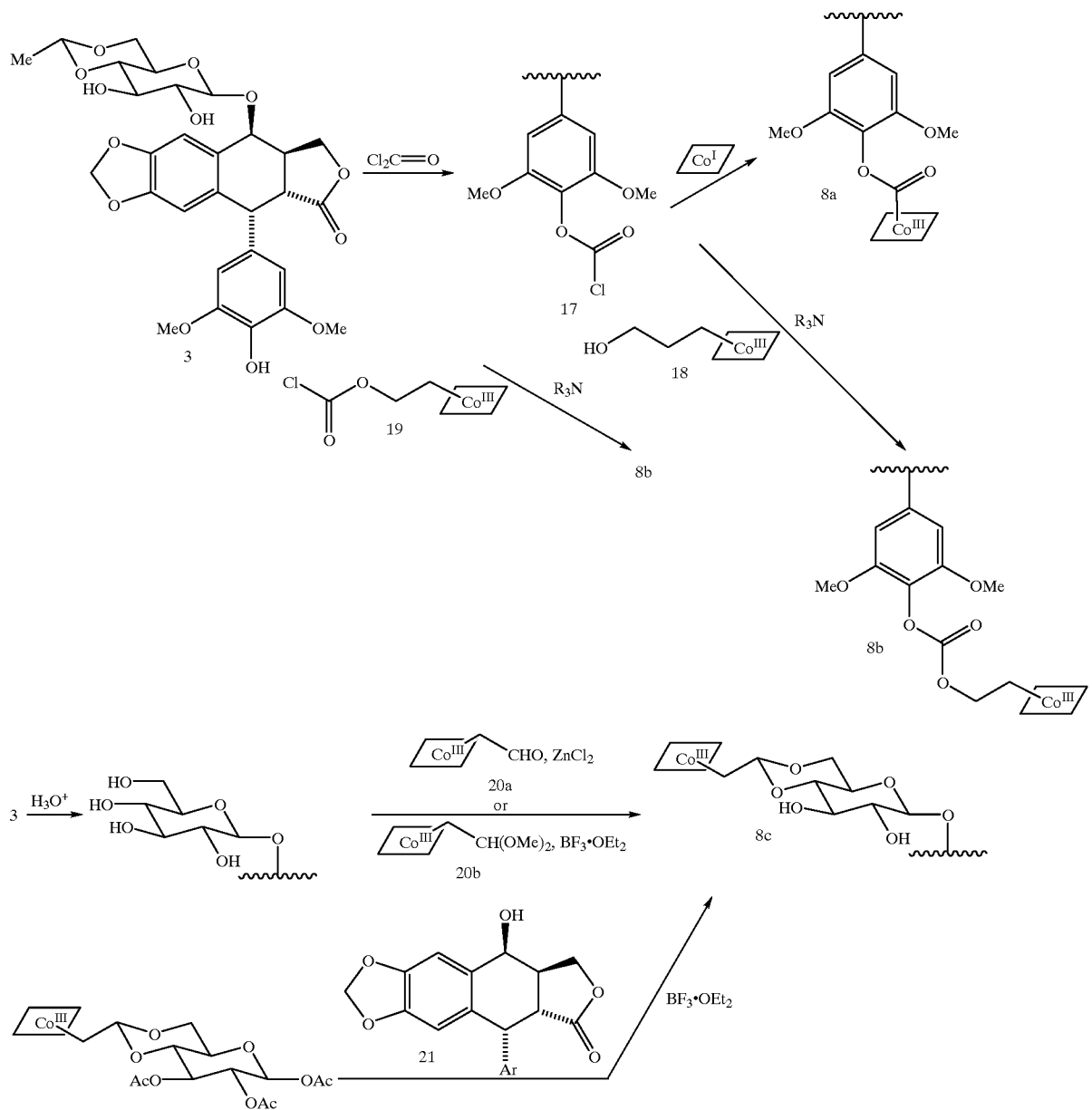

A doxorubicin-containing bioconjugate can be synthesized by the following method. Doxorubicin (4) is the most widely used of the anthracycline antibiotics, and is clinically useful against a broad spectrum of solid and hematological tumors. Like etoposide, doxorubicin appears to target topoisomerase II, ultimately leading to growth arrest and non-apoptotic cell death (Fornari et al., 1996; Ling et al., 1996). The clinical usefulness of doxorubicin is limited by non-specific toxicity, especially cardiotoxicity. Thus, it would appear to be a particularly good candidate for selective delivery. This is confirmed by its frequent use in liposome-based methods (Hu et al., 1996; Longman et al., 1995; Hosada et al., 1995), as part of immunoconjugates (Johnson et al., 1995; Sivam et al., 1995), or in prodrug approaches (Svensson et al., 1995).

Doxorubicin conjugated to cobalamin, Co[SALEN] and other organocobalt complexes, according to the following reaction schemes. For the synthesis bioconjugate 9a, the condensation of the daunosamine amino group with acyl-Co(III) complex 22 is performed. This, reaction forms the 2-pyrroline ring in analogy to published routes using 4-iodobutyraldehyde and 5-iodo-2-pentanone.(9b) The acyclic tertiary amine derivative 9b is available from 4 via initial reductive amination with acetaldehyde, then alkylation of the resulting secondary amine with the mesylate 23 derived from 18. Alternatively, treatment of 4 with chloroformate 19 provides carbamate 9c. If alternative points of attachment are desired, hydrazone-linked derivatives such as 9d can be used using simple cobalamin alkyl hydrazides such as 24, obtainable from 23. The cleavage of these bioconjugates is shown in the reaction scheme below.

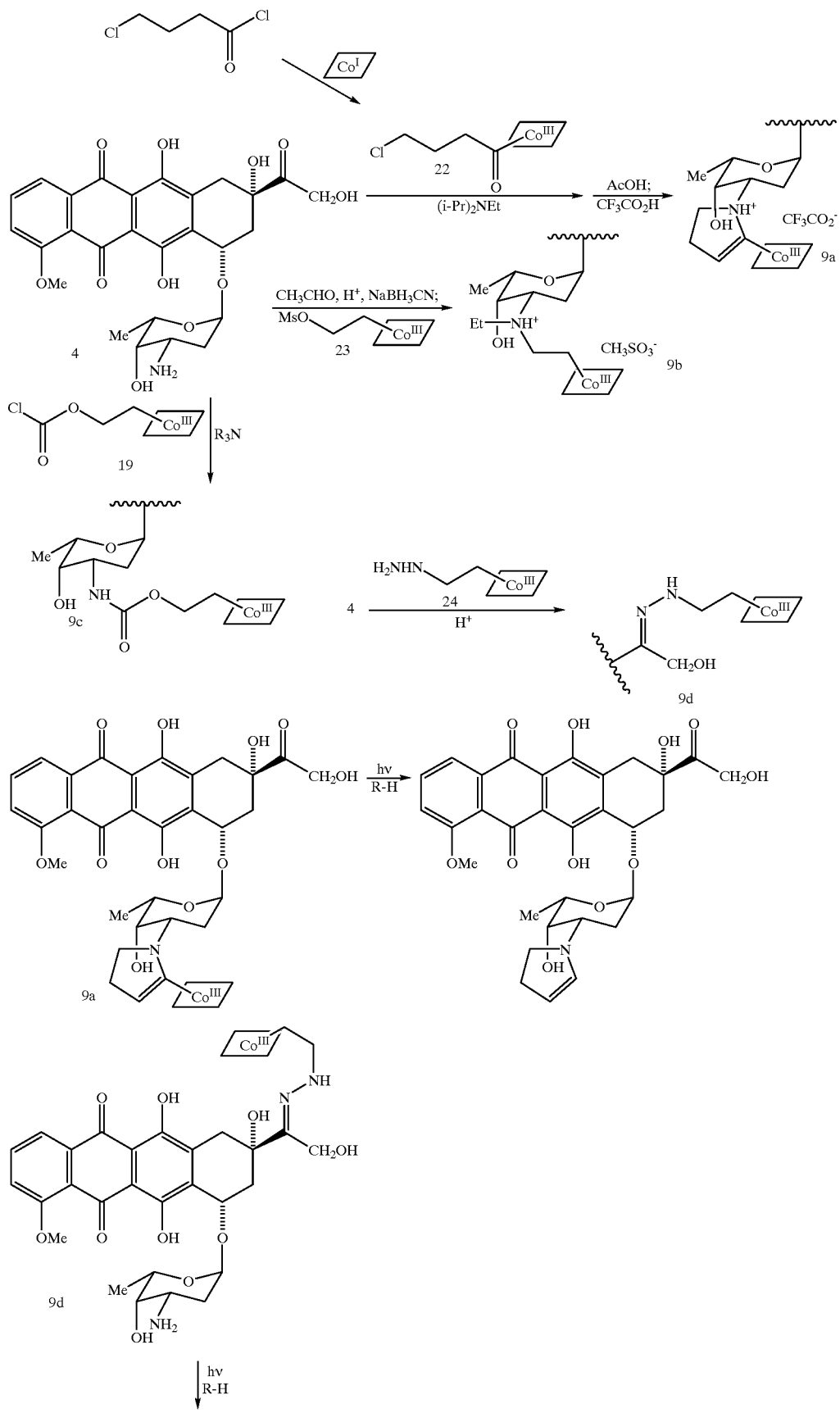

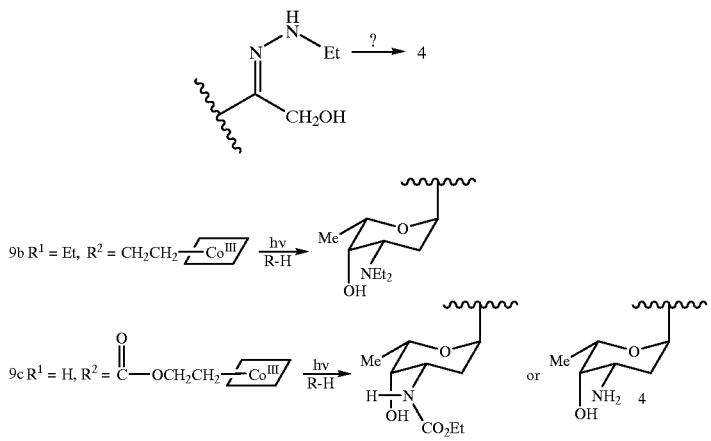

A carboplatin containing bioconjugate can be synthesized as shown in the following reaction scheme.

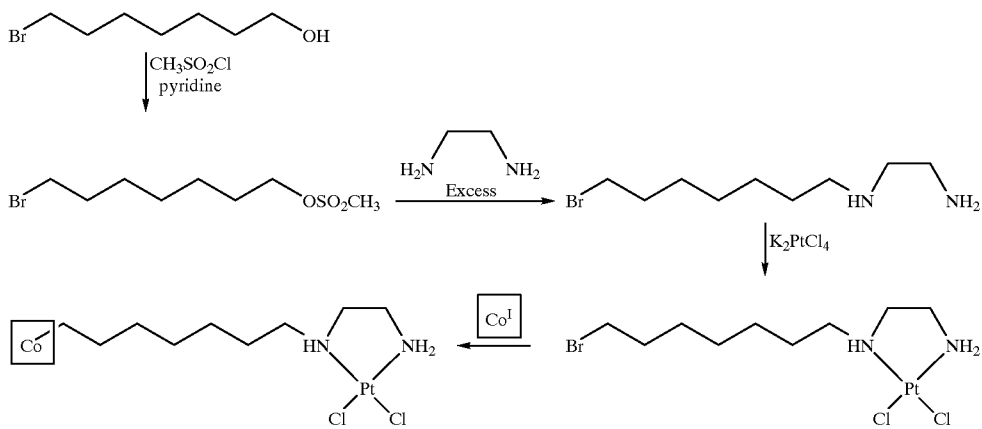

A peptide-containing bioconjugate can be synthesized by the following methods: (1) The C-terminal carboxyl group of the peptide can be activated and used to acylate Co(I), in analog), to the acylation of Co with chlorambucil acid chloride. (2) The C-terminal carboxyl group can be esterified with bromoethanol, in analogy to the other chlorambucil route, and the bromide displaced with Co(I). (3) The N-terminal amino group of the peptide can be treated with CH$_2$=O and Co(I) to form a Co(III)—CH$_2$—NH-peptide linkage, in analogy to the synthesis of the topotecan bioconjugate. (4) A Co(III)-amino acid complex can be prepared, and used in a coupling step with the remainder of the peptide. These methods can involve attachment of the Co at either the N- or C-terminus, or via a side-chain. A longer linker may be employed in any of these routes, if it is desirable to keep the cobalt complex further removed from the peptide chain.

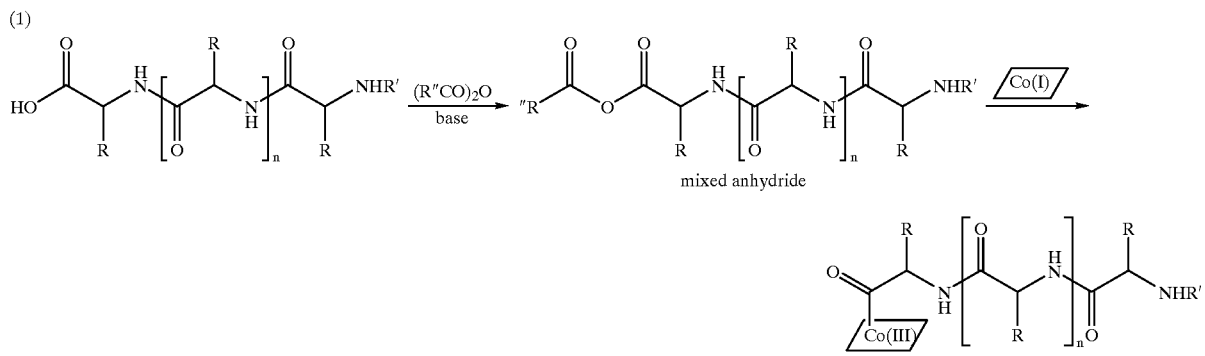

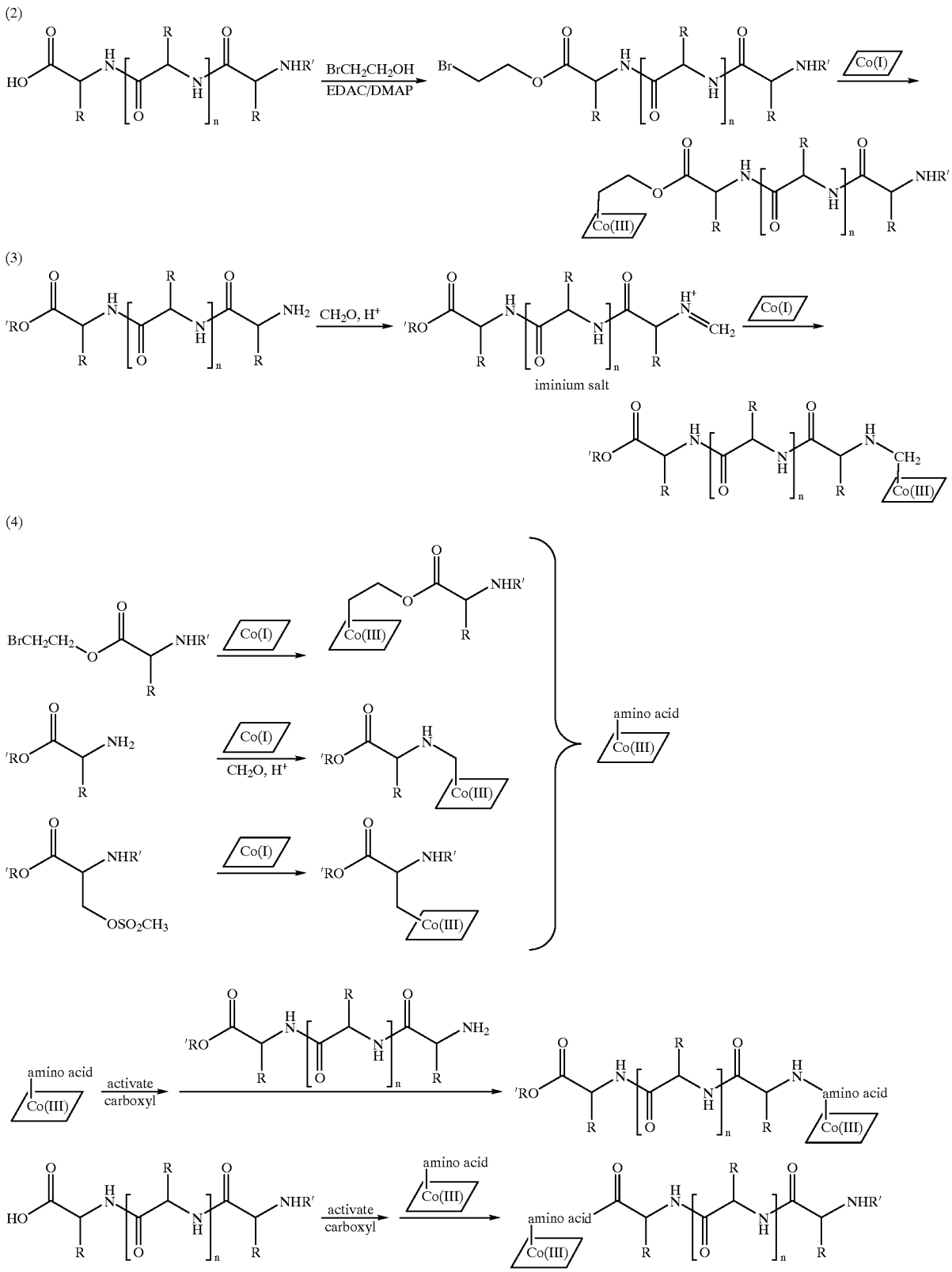
An oligonucleotide or nucleic acid containing bioconjugate can be synthesized by the following methods. In both methods, a phosphate ester is used to link the end of the nucleotide and a hydroxyethyl-Co group. This linkage can be accomplished by either directly coupling Co—CH$_2$CH$_2$—OH and Nucl-OPO$_3^{2-}$, or by esterifying Nucl-OPO$_3{}^{2-}$ with Br—CH$_2$CH$_2$—OH, then displacing the Br with Co(I), as above.

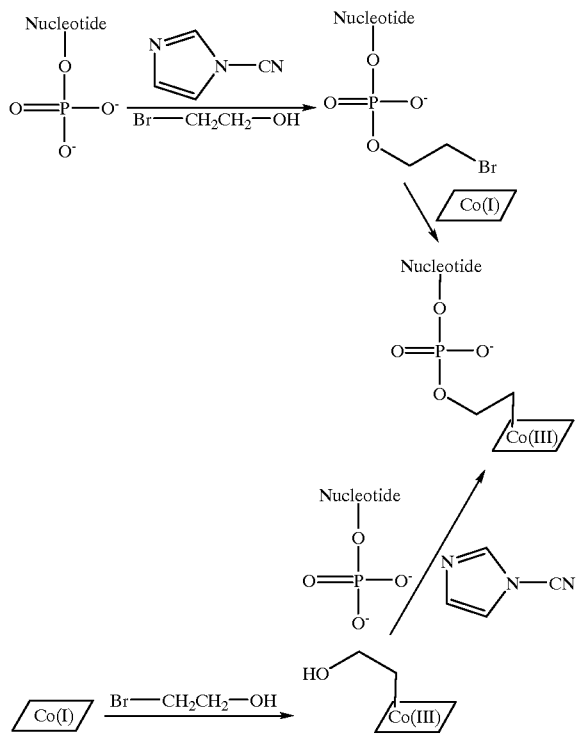

An unsymmetrically substituted Co[SALEN] complex can be prepared from 5-amino-salicylaldehyde and the glycolate ether of 2,5-dihydroxybenzaldehyde. The amino group, which is prepared from commercially available 5-nitrosalicylaldehyde, functions as the attachment for the targeting molecule (binding domain, BD) by way of EDCI-catalyzed amide formation. The other molecule has a carboxylic acid unit attached for solubility enhancement. Coupling of these two molecules with ethylenediamine and Co(II) acetate furnishes a mixture of three complexes: the two symmetrical complexes and the mixed one. All of these are useful, although the one lacking a BD-unit attached to either side of the SALEN is less preferred.

With regard to binding domains, two possibilities are shown: a cobalamin derivative, and a peptide. In the former case, the known carboxylic acid is used to attach cobalamin to the amino group of the SALEN. This bioconjugate still uses cobalamin-based receptor-mediated endocytosis to get into the cell, but the drug is attached through the SALEN instead of the cobalamin. The latter case uses a peptide known to bind to cell surface receptors of tumor cells (e.g., a fragment of epidermal growth factor), with the carboxyl terminus attached to the amino group on the SALEN. Alternatively, one of the glutamate carboxyl groups of folate is used to obtain a folate-based bioconjugate. In addition to connecting the binding domain via an amide linkage, one could use reductive amination if the targeting molecule contained an aldehyde (BD-CHO+SALEN-NH$_2$+NaBH$_4$), or one could use the carboxyl group on the other piece to form an amide or ester linkage. Many other approaches (e.g., ether formation, olefination by Wittig reaction, attachment via a diester or diamide linker, etc.) are also possible.

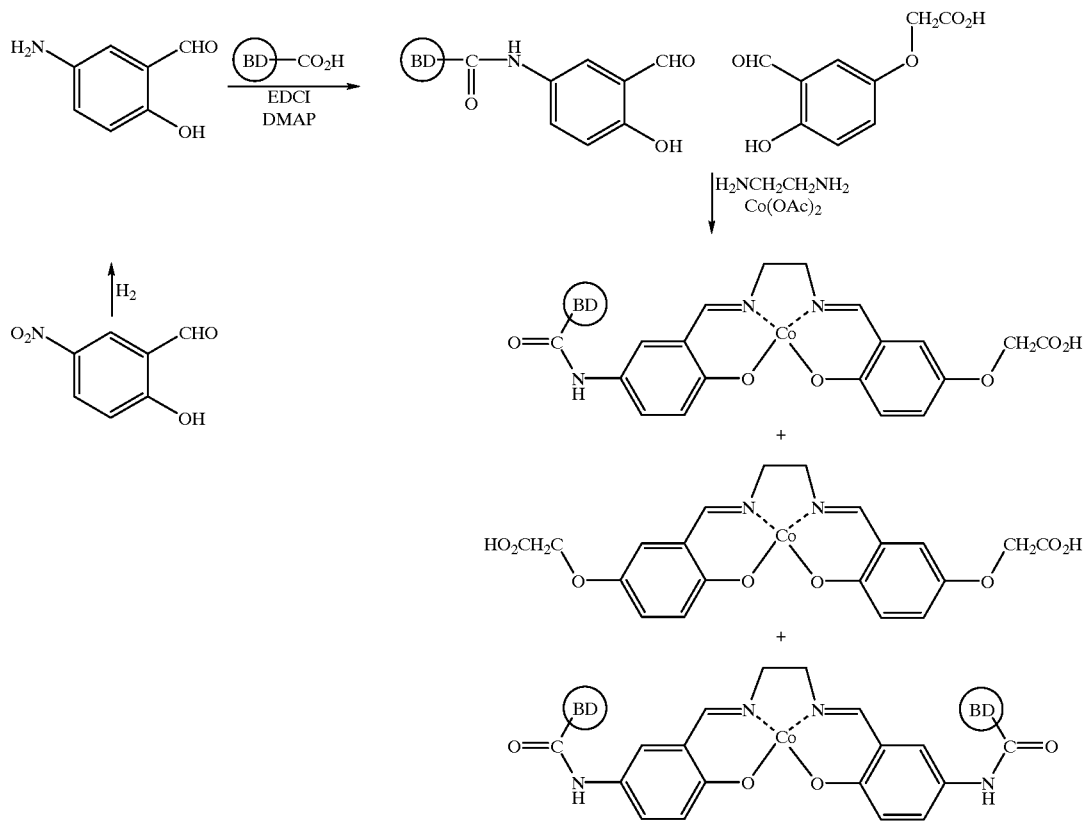

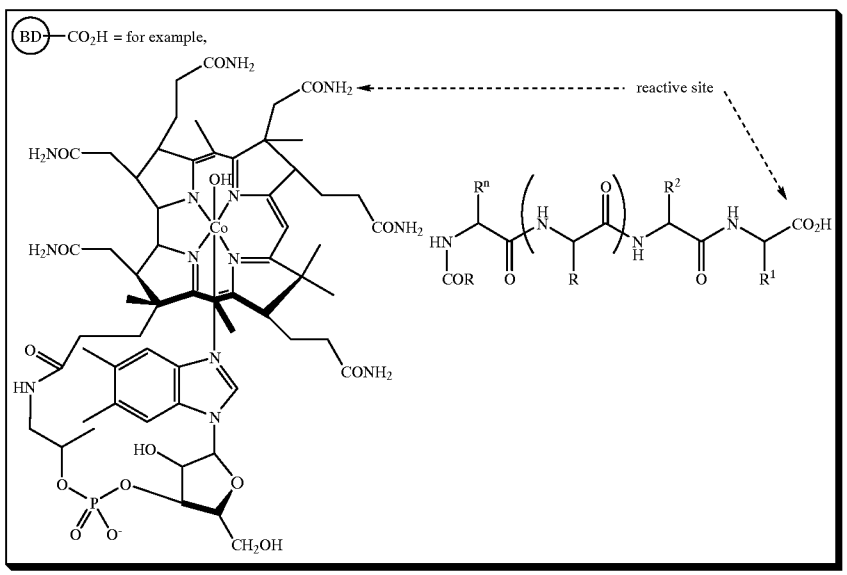

Extended benzenoid systems of the SALEN ligands are shown below.

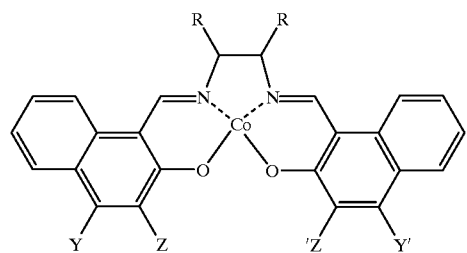

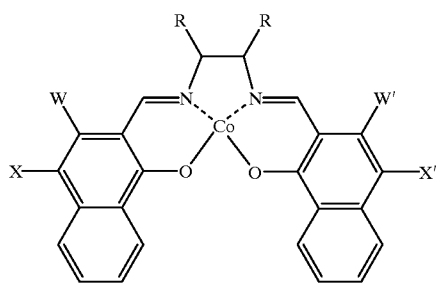

As a starting point in their synthesis, any of the commercially available naphthalene diols can be used. The diols undergo formylation reactions to furnish the molecules shown below. These molecules are then be coupled with Co(II) acetate and various diamines to give the extended Co[SALEN] complexes. The OH groups on the second ring can be left intact, used to attach the binding domain, or modified to enhance water solubility through attachment of a polar group, such as polyamine, polycarboxylic acid, or carbohydrate moiety.

1,5-dihydroxynaphthalene ⟶ 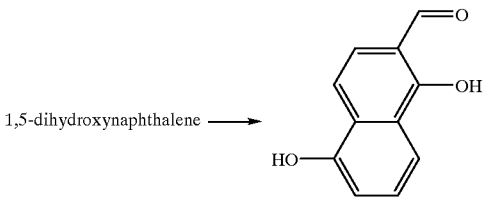

2,7-dihydroxynaphthalene ⟶ 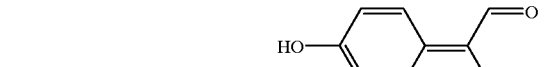

1,3-dihydroxynaphthalene ⟶ 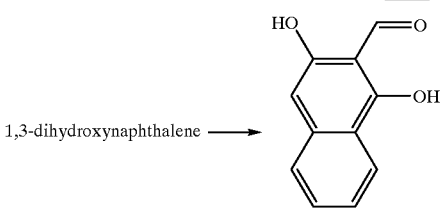

2,3-dihydroxynaphthalene ⟶ 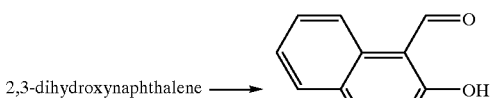

1,6-dihydroxynaphthalene ⟶ 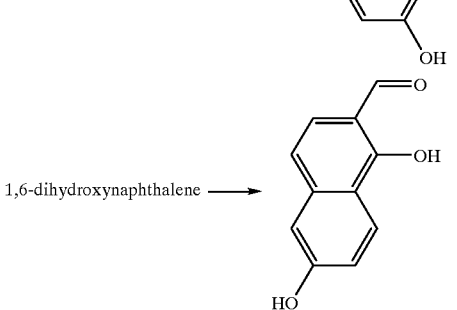

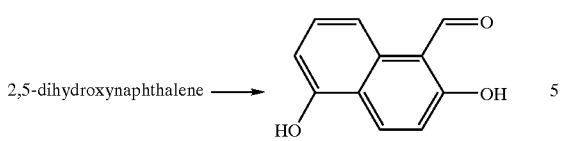

Modification of quinolines and isoquinolines are also carried out to give pyridine-fused SALENs.

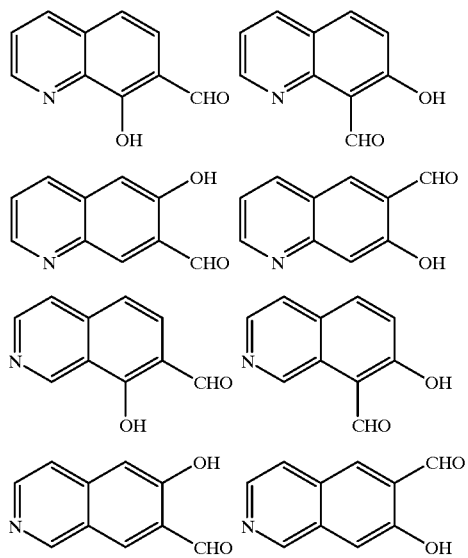

Along similar lines, SALENs derived from monocyclic heteroyclic hydroxyaldehydes are made, examples of which are shown below.

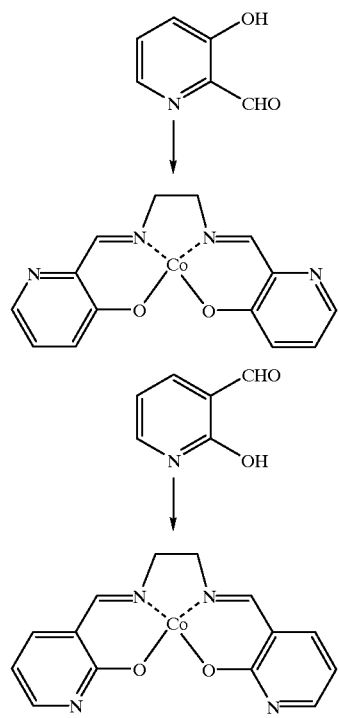

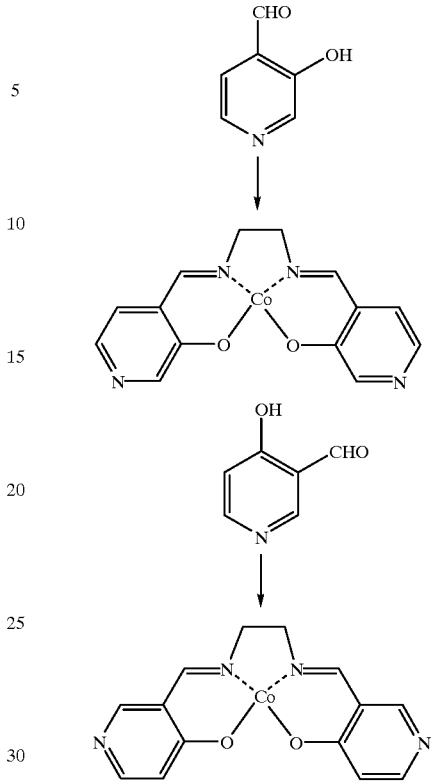

A bioconjugate containing the "green corrinoid" (Brown et al., 1996) can be synthesized as follows. The "green corrinoid" can be reduced in analogy to cobalamin, and that the reduced corrinoid will react with iodomethane to form the methylCo(III) corrinoid. Since the methylCo(III) corrinoid exhibits similar behavior to natural cobalamin, similar conjugation procedures with the electrophilic drug derivatives described above can be carried out.

The bioconjugates of the present invention have the improved property of being capable of targeted, selective release of the bioactive agent from the bioconjugate. The bioactive agent is is released from the bioconjugate by cleavage. In one embodiment, the cleavage may occur as a result of normal displacement by cellular nucleophiles or enzymatic action. In a second embodiment, the cleavage is caused to occur selectively at the release site by an external signal. The external signal may be light or photoexcitation, i.e. photolysis, or it may be ultrasound, i.e. sonolysis. Further, if the photolysis takes place in the presence of a magnetic field surrounding the release site, the release of the drug, such as a cytotoxic agent, into surrounding healthy tissue can be minimized.

Although it is desired to cause the bioactive agent to be released at the desired cells, tissue or organs, e.g., at the site of the tumor or other cancer cells, it is also desirable to protect adjacent tissues from the negative side effects of such potent agents. The bioactive agent is released from the bioconjugate at the targeted site preferably by application of an external signal, such as light or ultrasound. The photolysis of the bioconjugates of the present invention occurs though cleavage of the Co—C bond to produce a solvent-caged radical pair consisting of Co(II) and the bioactive agent radical (R.). Lott et al. (1995) demonstrate that alkylcob(III)alamin photolysis can undergo magnetic field dependent recombination. A magnetic field application of 100–3000 gauss can be used to enhance radical pair recombination in surrounding tissue where drug release from the conjugate is not desired, leading up to at least a 2-fold decrease in photochemically-triggered drug release in such surrounding healthy tissue.

The sonolysis of the bioconjugates of the present invention occurs through cleavage of the Co-non-reactive atom bond in aqueous solution to produce the bioactive agent and a Co(II) (e.g., cob(II)alamin ($Cbl^{II}$)) under anaerobic conditions or the bioactive agent and a aquoCo-(III) (e.g., aquocob(III)alamin ($H_2O$—$Cbl^{III}$)) under aerobic conditions. In either event, sonolysis from the focused application of ultrasound, results in Co-non-reactive atom bond cleavage and the irreversible release of the bioactive agent from the organocobalt complex.

The bioconjugates of the present invention can undergo natural cleavage as follows. Bioconjugates may be cleaved by natural means such as by serum nucleophiles. Once inside the cell, cobalamin-drug bioconjugates (utilized here only as an example and not intended to limit the invention) can undergo cleavage by a variety of mechanisms. Standard $B_{12}$ ligand exchange mechanisms permit the displacement of the drug. Alternatively, cellular nucleophiles can attack at either the carbon or the cobalt atoms of the CO—C bond. Cyanide is the most common example of a nucleophile which attacks at cobalt, leading to cyanocob[III]alamin and a free drug in which the former C—Co bond has been replaced with a C—H bond. Thiols (such as are found in cysteine or glutathione) can attack at carbon, leading to a reduced cob[I]alamin and a free drug which incorporates the former thiol group.(e.g., R—Co[III]+R'—SH+base→R—S—R'+Co[I]+base—H.) Hydroxide and other basic agents can also cleave organic ligands from Co[III] complexes, although this typically occurs via an elimination process which alters the structure of the ligand through incorporation of a new double bond. In addition, $B_{12}$ metabolic enzymes present in cells can result in the cleavage of the bioactive agent from the co-atom.

The bioconjugates of the present invention can undergo cleavage by photoactivation or photolysis as follows. The photochemical release of the bioactive agent from the organocobalt complex can be triggered by the application of visible light at 400–800 nm. It is preferred to use organocobalt complexes which require longer wavelengths of visible light (600–800 nm), more preferably red light (600 to 750 nm). When photolysis is utilized for the release of the bioactive agent form the bioconjugate, it is particularly preferred that the non-reactive atom of the bioactive agent or the atom of the spacer bound to the cobalt atom be a carbon atom.

The vitamin $B_{12}$ cofactor occurs naturally in two forms: adenosylcob(III)alamin. ($AdoCbl^{III}$), also known as coenzyme $B_{12}$, and methylcob(III)alamin ($CH_3Cbl^{III}$). The remarkably weak C—Co bond from the corrin ring to the 5'-deoxyadenosyl or methyl ligand imparts a most unusual chemistry to cobalamins. The C—Co bond energy in $AdoCbl^{III}$ and $CH_3Cbl^{III}$ is estimated to be as low as 31 and 37 kcal/mole, respectively. This makes the C—Co bond one of the weakest covalent bonds known and allows photocleavage of the bond by visible light. The initial product of the photocleavage of $AdoCbl^{III}$ is the geminate radical pair {$CH_2$-Ado: $Cbl^{II}$}. Brackets {: } indicate the radical pair is geminate (born of the same parent molecule) and held in close proximity by solvent interactions. Picosecond laser flash photolysis experiments of $AdoCbl^{III}$ have shown this to be a reversible process with a geminate recombination rate constant of $k_{rec} \approx 1 \times 10^9 s^{-1}$, following photolysis. Recent nanosecond laser flash photolysis studies have probed a slower radical pair recombination that occurs in the solvent and is limited by diffusion.

Figure 2:
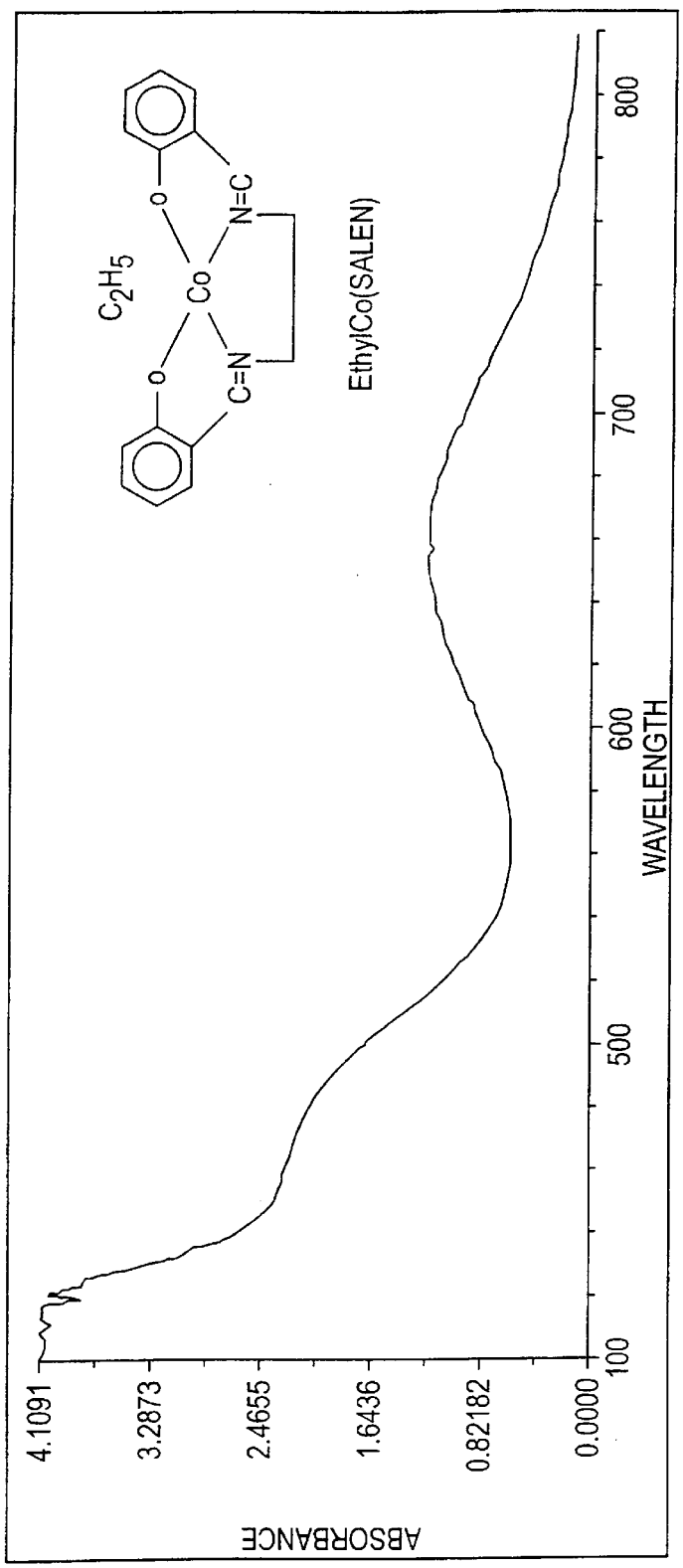
FIG. 2 shows the structure and absorption spectrum of ethyl-Co[SALEN] (cobalt-bis-[salicylidene]-ethylenediamine.

The $\pi$-$\pi^*$ electronic transition of the corrin ring of cobalamin produces a long wavelength absorption maximum at 525 nm, as shown by FIG. 1. Irradiation of alkylcobalamins at this wavelength leads to cleavage of the C—Co bond with a photolysis quantum yield of 0.1–0.3. The in vivo photolysis of bioconjugates according to the present invention is preferably accomplished by delivering the light with a fiber optic probe because of the strong absorption of hemoglobin near this wavelength. To avoid potential problems with the absorption spectrum of cobalamin while maintaining a photolabile C—Co bond, Co[SALEN], which is a five-coordinate analogue of coenzyme $B_{12}$, can be used. Alkyl-Co [SALEN] complexes have absorption maxima near 650 nm, with significant absorption beyond 700 nm as shown by FIG. 2. This is a distinct advantage for photoactivatable drug release, as human tissue becomes increasingly transparent above 610 nm. Other synthetic or naturally occurring $B_{12}$ derivatives are, or may become, available that have absorption maxima above 600 mn. For example, a green cobalt corrinoid having an absorption maximum at about 624 nm is reported by Brown et al. (1996). Human tissue becomes transparent to depths of up to about 5.7 cm at wavelengths of between about 600 and 800 nm. The use of longer wavelengths enables the more selective irradiation of limited portions of a subject's body, with consequent release in a small target region.

The bioconjugates of the present invention can undergo cleavage by photoactivation or photolysis in the presence of a magnetic field as follows. The use of the magnetic field further limits the release of the bioactive agent to the desired site. For example, because of the toxicity of antineoplastic agents to healthy tissues, it is incumbent upon any effective site specific delivery system to limit damage to cells other than at the site of activity. In the photohomoylsis cleavage reaction, the electrons in the broken covalent bond start out with their spins paired ↑↓ (singlet state) from having participated in the covalent bond. During the early lifetime of the radical pair, the spins retain their original orientation R↑+↓R' until the electron spins randomize over time. During the time the spins are paired, the radicals can recombine and revert to the starting material. If either of these paired radical spins should intersystem cross (ISC) to the triplet spin state (R↑+↓R') they can no longer recombine until their spins are once again paired. That situation is preferred to release the bioactive agent from the bioconjugate. However, in healthy tissue, it is desired to prevent, or at least minimize, the cleavage of the conjugate. It that event, it is desirable to alter the rate of ISC by introducing an external magnetic field that increases the gap between the triplet state energy levels, thus encouraging the recombination of the original bioconjugate in the healthy tissues.

The recombination rate can be increased by application of a magnetic field in the range of 100–3000 gauss to the healthy tissues leading to a net decrease in the photochemical quantum yield and a decrease in drug release into healthy tissues by a factor of at least 2. Application of about 300 to 1000 gauss is considered to be optimal. See, Grissom (1995).

The bioconjugates of the present invention can undergo cleavage by ultrasound or sonolysis as follows. Although any non-reactive atom can be bound to the cobalt atom in the bioconjugate and cleaved by sonolysis, it is preferred that the atom be a carbon atom. The vitamin $B_{12}$ cofactor occurs naturally in two forms: adenosylcob(III)alamin, (AdoCbl$^{III}$), also known as coenzyme $B_{12}$ and methylcob(III)alamin, (CH$_3$Cbl$^{III}$). The remarkably weak C—Co bond from the corrin ring to the 5'-deoxyadenosyl or methyl ligand imparts a most unusual chemistry to cobalamins. The C—Co bond energy in AdoCbl$^{III}$ and CH$_3$Cbl$^{III}$ is estimated to be as low as 31 and 37 kcal/mole, respectively. This makes the C—Co bond one of the weakest covalent bonds known and allows sonolysis of the bond by the application of ultrasound in the range of about 20 kHz–500 MHz, preferably 20 kHz–100 MHz, more preferably 20 kHz to 10 MHz.

Sonolysis of aqueous solutions produces a high concentration of hydroxyl radicals and hydrogen atoms according to the equation:

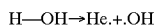

$$H-OH \rightarrow He. + .OH$$

These reactive oxidizing and reducing species are responsible for initiating most reactions in aqueous solvents. Ultrasound irradiation and sonochemistry are often not described as high-energy processes, but during sonolysis, the development, growth and implosion of bubbles in a liquid create extreme reaction environments on a microscopic scale. The collapse of cavitation bubbles produces pressures >500 atm. and temperatures >5000° C. The radicals formed survive the collapse of the bubbles. The formation of hydroxyl radicals in vivo has been the focus of several investigations because of the potentially deleterious effects of oxidizing free radicals in human tissue. However, such radicals do not present an unacceptable health risk, as clinical experience has demonstrated that diagnostic ultrasound is a benign procedure. The ability to form these radicals by sonolysis in vivo provides a mechanism for the triggered release of active neoplastic and other agents from conjugation with $B_{12}$, Co[SALEN] or other suitable cobalamin or cobalamin like substrates.

In the sonolysis of drug-$B_{12}$ conjugates (utilized here only as an example and not intended to limit the invention), the C—Co bond is cleaved in aqueous solution to produce the drug and a cob(II)alamin (Cbl$^{II}$) under anaerobic conditions or the drug and aquocob(III)alamin (H$_2$O—Cbl$^{III}$) under aerobic conditions. The cleavage is not a direct breaking of the C—Co bond. Rather, under anaerobic conditions the predominant pathway for C—Co bond cleavage by sonolysis is through reduction of drug-Cbl$^{III}$ to the labile drug-Cbl$^{II}$ by H., followed by dissociation to the closed-shell drug and Cbl$^{II}$. The reaction of HO. with drug-Cbl$^{II}$ leads to H$_2$O—Cbl$^{III}$, as well as degradation of the corrin ring. Under aerobic conditions, the pathway for the C—Co bond cleavage by sonolysis is through reduction of the drug-Cbl$^{III}$ to produce drug and Cbl$^{II}$, but O$_2$ oxidizes Cbl$^{II}$, to H$_2$O—Cbl$^{III}$. In either event, sonolysis from the focused application of ultrasound, results in C—Co bond cleavage and the irreversible release of the drug from the cobalamin. Therefore, sonolysis-triggered release can occur under aerobic and hypoxic conditions alike.

The present invention is useful in the treatment of (including, but not limited to) cancer, hepatitis, psoriasis and other localized diseases, as well as for gene therapy and peptide therapy. The bioconjugates according to the present invention can be administered by any route, including intravenously, parenterally, orally, intramuscularly, intrathecally or as an aerosol. The mode of delivery will largely depend on the biological effect desired to be achieved. A skilled artisan will readily know the best route of administration for a particular treatment in accordance with the present invention. The appropriate dosages will depend on the route of administration and the treatment indicated, and can be readily determined by a skilled artisan, such as by extrapolation from current treatment protocols. If the organocobalt complex of the bioconjugate is cobalamin or derivative or analogue, it is preferred to administer orally a bolus of vitamin $B_{12}$ prior to administration of the bioconjugate to reduce or eliminate potential hepatotoxicity which might otherwise result from the administration of the bioconjugate. The oral dose of $B_{12}$ will saturate the enterohepatic shuttle system and load hepatocytes with cobalamin. It is preferred that 0.1 mg to 100 mg, more preferably 1.0 mg to 10 mg, of vitamin $B_{12}$ be administered prior to the administration of the bioconjugate containing cobalamin. In addition, vitamin $B_{12}$ can be administered, preferably intravenously, following the selective cleavage of bioconjugate to wash out all bioconjugate which has not been cleaved, and thus further reduce potential systemic effects. It is preferred that 0.1 mg to 100 mg, more preferably 10 mg to 100 mg, of vitamin $B_{12}$ in saline be administered intravenously over 4–5hrs. Finally, prior to the administration of a cobalamin-based bioconjugate, nitrous oxide can be administered to the subject in order to deplete body stores of cobalamin in its various forms, such as methylcobalamin. Administration of nitrous oxide has the effect of creating a greater body deficit of cobalamin before administration of the cobalamin-based bioconjugate.

Pharmaceutical compositions containing a compound of the present invention as the active ingredient can be prepared according to conventional pharmaceutical compounding techniques. See, for example, *Remington's Pharmaceutical Sciences*, 17th Ed. (1985, Mack Publishing Co., Easton, Pa.). Typically, an antagonistic amount of active ingredient will be admixed with a pharmaceutically acceptable carrier. The carrier may take a wide variety of forms depending on the form of preparation desired for administration, e.g., intravenous, oral, parenteral, intrathecal, transdermal, or by aerosol.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent must be stable to passage through the gastrointestinal tract. If necessary, suitable agents for stable passage can be used, and may include phospholipids or lecithin derivatives described in the literature, as well as liposomes, microparticles (including microspheres and macrospheres).

For parenteral administration, the compound may dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intracerebroventricularly or intrathecally, they may also be dissolved in cerebrospinal fluid.

In the treatment of cancer (sarcomas, carcinomas or leukemias), a distinction can be made between the types of systemic adjuvant chemotherapies that are typically used in concert with the more extreme methods of surgical excision and radiation therapy. There are two broad classes of chemotherapeutic adjuvants: (1) endocrine and antivasogenic therapeutic agents which are aimed at altering the body's physiology; and (2) cytotoxic chemotherapeutic agents which are typically administered systemically to kill or inhibit the growth of transformed cells.

Cytotoxic or antineoplastic agents are represented by a number of drug classes. Alkylating agents undergo chemical reactions that generate highly reactive electrophilic carborationsnium ions that readily form covalent linkages (alkylate) with various nucleophilic biologically important moieties such as nucleic acid bases and phosphate, amine, sulfhydryl, hydroxyl, carboxyl and imidazole groups. These agents, among other functions, have cytotoxic actions that disturb the fundamental mechanisms concerned with cell growth, mitotic activity, differentiation and function. Chlorambucil, modified busulfan, cyclophosphamide, ifosfamide and cisplatin and its structural analogs are representative alkylating agents.

Antimetabolites such as folic acid analogs (e.g. methotrexate) and pyrimidine analogs (e.g. fluorouracil and fluorodeoxyuridine) exert cytotoxic activity by blocking or preventing metabolic pathways leading to neoplastic cell destruction. Methotrexate is also known to be useful in the treatment of psoriasis by inhibiting the proliferation of epidermal cells.

Another potent cytotoxic class is mitotic inhibitors such as the paclidaxel or the alkaloids camptothecin, vincristine and vinblastine.

Also, certain antibiotics, such as doxorubicin and daunorubicin, (tetracyclic aglycone glycosides), intercalcate with DNA and inhibit nucleic acid synthesis.

In accordance with the present invention, bioconjugates for the treatment of cancer are formed preferably using chemotherapeutics selected from the group consisting of alkylating, agents, antimetabolites and mitotic inhibitors. For example, methotrexate is an antimetabolite; chlorambucil, cisplatin and modified busulfan are alkylating agents, and camptothecin and its derivatives are alkaloids. The bioconjugates formed from these cytotoxic agents can be administered intravenously for the treatment of the specific classes of cancer for which they are known to be effective, e.g. cancer of the colon, lung, kidney, breast, prostate, melanoma, nasopharyngeal, T-cell leukemia, myelogenous leukemia, lymphocytic leukemia and the like. When delivered intravenously to the blood stream and the bioconjugates contain cobalamin, the natural affinity of cancer cells for $B_{12}$ will target the bioconjugates to these tissues or cell sites. Alternatively, the bioconjugates can be engineered to be selective for the delivery of the chemotherapeutic agent to the desired cancer cell by the incorporation of a suitable targeting, molecule (such as those set forth above) on the organocobalt complex.

In accordance with the present invention, solid tumors are treated as follows, with use of a drug-$B_{12}$ bioconjugate as an example. This example is not intended to limit the present invention in any manner, and a skilled artisan could readily determine other bioconjugates of the present invention which could be utilized for the treatment of solid tumors. The drug-$B_{12}$ bioconjugate is administered, preferably intravenously, to a cancer patient to target metastatic cancer when the cancer cell has a significant requirement for cobalamin. This propensity of cobalamins to migrate to the cancer cells significantly reduces cardiotoxicity, myelotoxicity, hepatotoxicity and similar side effects that limit the size and frequency of effective dosing of antineoplastic agents. Furthermore, problems associated with toxicity to non-targeted cells is minimized. Delivery is further enhanced by the triggering of the release of the antineoplastic agent from the bioconjugate by the mechanism of photolysis or sonolysis which provides for a high degree of spatial and temporal control of the drug release at a localized area over a short time. The application of a magnetic field with photolysis further serves to protect health cells by recombination of the bioconjugate and limit the release of active agent to the specific cancer cell-containing site(s).

Although chemotherapy is generally reserved for targeting metastasized cells after the surgical excision of the primary tumor mass, the triggered release of a bioactive agent drawn to the tumor site allows for treatment of the primary tumor, as well as metastatic neoplasms that have spread to a limited and known area. The bioconjugate dosage, length of treatment, degree of photoactivation, and other treatment parameters can be determined by one skilled in the art based on the type of cancer, antineoplastic agent administered, specific cobalamin used, condition of the patient and other factors which are variable and best determined on a case-by-case basis.

In accordance with the present invention, leukemia is treated as follows, with use of a drug-$B_{12}$ bioconjugate as an example.. This example is not intended to limit the present invention in any manner and a skilled artisan could readily determine other bioconjugates of the present invention which could be utilized for the treatment of leukemia. At least two forms of leukemia, chronic myeloid leukemia (CML) and acute promyeloctyic leukemia (APL), produce high levels of $B_{12}$ binding proteins that result in a 3- to 36-fold increase in the unsaturated $B_{12}$ binding capacity in the blood. The increased concentration of $B_{12}$ binding proteins is consistent with the rapid turnover of immature blood cells and provides an opportunity to target the delivery of antileukemic drugs, such as bis-alkylating agents derived from busulfan, to the transformed hematopoietic cells responsible for the leukemic condition. The bioconjugates of this invention provide a means for the effective administration of such alkylating agents to cell sites from which the active agent can be released from the conjugate. This targeted delivers and release provides a significant advance in the treatment of CML and APL, for which current chemotherapy methods sometimes provide incomplete remission.

The present invention is also useful for the treatment of psoriasis. Psoriasis is a prime target for the transdermally or orally controlled delivery of antimetabolites activated by photolytically induced cleavage. Although not life-threatening, psoriasis can significantly diminish the quality of life of patients who experience severe exfoliation associated with psoriatic and rheumatoid arthritis. Antimetabolites, such as methotrexate and 5-fluorouracil, are effective in controlling severe cases of skin proliferation. Effective oral therapy is limited by hepatotoxicity in spite of low dosing, and the risk of cumulative liver damage requires such therapy to be reserved for only the most severe episodes during a patient's life. The delivery of such agents to the skin improves the appearance and psychological quality of life of patients whose lives have been dominated by severe psoriasis.

The present invention is further useful for peptide therapy. One example of peptide therapy is as a cytotoxic agent, for example as an antineoplastic agent. In this example, a bioconjugate containing the enzymatic domain of diphtheria toxin (DT) is administered to a subject such as described above for solid tumors or leukemia. The targeted release of the DT peptide results in the inhibition of protein synthesis and eventual cell death.

The present invention is also useful for gene therapy. One example of gene therapy is the delivery of an antisense oligonucleotide to inhibit viral gene expression and viral replication. In this example, a bioconjugate containing an antisense oligonucleotide against hepatitis B virus is administered to a patient having a hepatitis B infection. The accumulation of the bioconjugate and release of the antisense oligonucleotide in the liver inhibits hepatitis B virus gene expression and replication.

The present invention is further described by reference to the following Examples, which are offered by way of illustration and are not intended to limit the invention in any manner. Standard techniques well known in the art or the techniques specifically described below were utilized.

EXAMPLE 1

Photolysis of $B_{12}$ and Co[SALEN] Bioconjugates

A protocol for a typical anaerobic continuous-wave photolysis of methylcob(III)alamin or $CH_3Cbl^{III}$ is as follows. An aqueous solution of 200 μM $CH_3Cbl^{III}$ and 50 mM $K^+$Hepes pH 7.3 is placed in a 1 cm quartz cuvette. Samples that are to be photolyzed under anaerobic conditions are either subjected to repeated freeze-pump-thaw cycles, or purged with Ar for 40 minutes immediately prior to photolysis and sealed. Continuous-wave visible light irradiation is accomplished at the desired wavelength with an $Ar^+$pumped dye laser. The incident light on the face of the cuvette is reduced to 12 mW $cm^{-2}$ with neutral density filters. The light flux is determined by potassium ferrioxalate actinomety and by a Scientech surface-reading thermopile. The cuvette is placed in a thermostated cell holder at 25–37° C. For quantum yield measurements as a function of magnetic field, the cuvette is placed in the gap of a GMW Associates electromagnet with 7.5 cm diameter cylindrical poles. The magnetic field within the area of the cuvette is homogeneous to within 2% and the long term stability is better than 0.5% as monitored by a transverse Hall probe and digital teslameter.

Absorption spectra from 300–600 nm are recorded in one second with a diode array spectrophotometer at variable time intervals from 10 seconds to 2 minutes (depending upon the fluence of the photolyzing light source) for a total of 3 $\tau_{1/2}$. Exposure to light during analysis is kept to a minimum. The concentration of $CH_3Cbl^{III}$ is determined using the measured absorbance at 350 or 520 nm by the method of Chen and Chance (1993). The plot of $[CH_3Cbl^{III}]$ vs. time (t) appears zero-order in all cases.

Selection of Photolysis Wavelength: The absorption spectra for $CH_3Cbl^{III}$ and ethyl-Co[SALEN] are shown in FIGS. 1 and 2. For $CH_3Cbl^{III}$ the π-π* electronic transitions that lead to cleavage of the C—Co bond are maximal at 377 and 528 nm. Much preliminary work with $B_{12}$ photolysis has been carried out with 514 nm light from an Argon-ion ($Ar^+$) laser. This is close to the long-wavelength maximum absorbance and gives a quantum yield of about 0.3 for $CH_3Cbl^{III}$.

The absorbance of blood and tissue is significant at this optimal wavelength for cob(III)alamin excitation. Blood has a low (partial) transmittance window near 514 nm. This absorbance is sufficient to quickly pyrolize whole bovine blood placed in the light path of a 20 W/cm² beam of 514 nm light.

It would therefore be beneficial to provide a cobalamin for conjugation wherein the π-π* electronic transitions that lead to cleavage of the C—Co bond are maximal at a wavelength where there is minimal or no interference. Above about 610 nm blood becomes partially transparent and losses beyond 50% transmittance are largely due to light scattering from the erythrocytes. Heparinized bovine blood placed in the light path of a 20 W/cm² beam of 630 nm light shows only minor heating over long exposure times. There is also demonstrated a high transmittance of tissue at 610–800 nm.

This suggests the use of an organocobalt complex for conjugation having an absorption wavelength where tissue and blood are relatively transparent. FIG. 2 shows that ethyl-Co[SALEN] complexes have absorption maximums near 650 mm, with significant absorption beyond 700 nm. An $Ar^+$-pumped dye laser or a Krypton-ion ($Kr^+$) laser can be a suitable high-intensity source of photons in the region of $610^+$ nm. $Ar^+$-pumped dye lasers are often used for photodynamic therapy with hematoporphyrins. Also, an inexpensive He—Ne laser, having a principal line at 633 nm might be used. However, such lasers are typically limited to 50 mW maximum output.

There are laser dyes in the 600–700 nm region that can achieve energy conversion efficiencies of up to 45%. This means that a 6 W $Ar^+$ pump laser can yield nearly 3 W of spatially-coherent monochromatic light in the region of 610–750 nm. The exact wavelength can be chosen to optimize the continuous-wave quantum yield and still maintain a reasonable degree of tissue penetration. In tests with alkyl-Co[SALEN] complexes it has been found that 690 nm light from an $Ar^+$-pumped dye laser operating with rhodamine 6-G dye is satisfactory Optimization can be determined depending on the specific cobalamin chosen for animal and/or clinical trials of the bioconjugates. In addition, high-power diode lasers that emit red light of the desirable wavelength are commercially available. These diode lasers have the advantage of providing up to 100 watts of optical power in a narrow region of the optical spectrum that is useful for triggering cleavage of the bioconjugates.

EXAMPLE 2

Sonolysis of $B_{12}$ and Co[SALEN] Bioconjugates

Sonolysis was carried out with a Branson ultrasonic bath (model 3200) operating at 47 kHz. The correct placement of the reaction vessel at a focal point of high-intensity ultrasound was determined by the oxidation of iodide to iodine in the presence of starch (Mason, 1991) and the temperature of the bath was maintained at 21° C. by a constant temperature circulator. Aerobic sonolysis was typically carried out in a test tube or Erlenmeyer flask, whereas anaerobic sonolysis was carried out in a closed reaction vessel fitted with a sidearm and quartz cuvette. Anaerobic conditions were produced by sparging with Ar for 30 min prior to sonolysis. In some experiments, the pH was buffered by the use of 100 mM phosphate (aerobic experiments) or 100 mM N-(2-hydroxyethyl)piperazine-N-2-ethanesulfonate (Hepes) (anaerobic experiments), as specified. All procedures were carried out in the absence of light to prevent photolytic cleavage of the Co—C bond. Absorption spectra were recorded on a diode array spectrophotometer (HP 8452A). The solutions were transferred to a quartz cuvette with a 1 cm light path for all optical measurements and care was exercised to ensure that insignificant photolysis occurred during the 1 s measurement time.

Figure 3A:
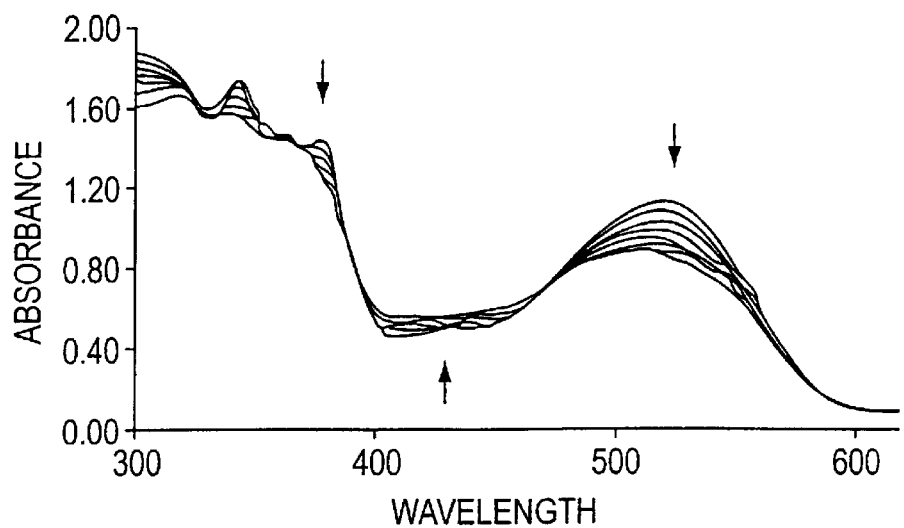
FIG. 3A shows a sequential absorption spectra of aqueous $CH_3$—$Cbl^{III}$ as a function of anaerobic sonolysis (pH 7.38, 100 mM Hepes, saturating Ar).

Sonolysis of Methylcob(III)alamin: Sequential absorption spectra of aqueous $CH_3$—$Cbl^{III}$ as a function of anaerobic sonolysis (pH 7.38, 100 mM Hepes, saturating Ar) are shown in FIG. 3A. The absorbance at 340, 374, and 520 nm decreases linearly as a function of sonolysis time and the absorbance at 316 and 420 nm increases linearly, thereby indicating the reaction is zero order in substrate concentration. The isosbestic points at 336, 390, and 585 nm are in agreement with those obtained through anaerobic photolysis of $CH_3$—$Cbl^{III}$. Under the conditions of sonolysis, an additional isosbestic point occurs at 476 nm, rather than at 486 nm, as typically observed in the course of photolysis. This slight shift in the isosbestic point is caused by a minor product that has an absorbance maximum near 490 nm. This may be cob(I)alamin that has a sufficient lifetime ($t_{1/2}$=22 min at pH 6) to be observed spectrophotometrically. The absorption band at 374 nm is characteristic of a C—Co bond, and its disappearance unambiguously indicates displacement of the axial carbon ligand.

Under aerobic conditions, molecular oxygen scavenges H. and prevents the reduction of $CH_3$—$Cbl^{III}$ via the equation $$O_2 + H. \rightarrow .OOH$$

In the absence of an organic buffer with abstractable hydrogen atoms, reaction via HO. remains to be a viable process.

Figure 3B:
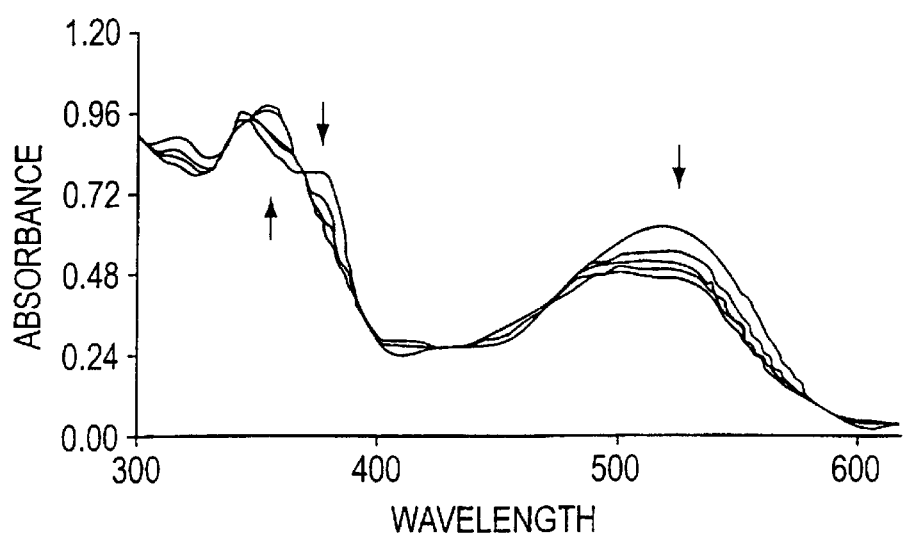
FIG. 3B shows the change in absorbance spectra following aerobic sonolysis in the absence of organic buffer.

FIG. 3B shows the change in absorbance spectra following aerobic sonolysis in then absence of organic buffer. The decrease in absorbance at 340 and 374 nm is linear with increasing sonolysis time indicating the reaction is zero order in substrate concentration, but the unexpected increase in absorbance at 520 nm indicates the stable product of cobalamin sonolysis is not hydroxocob(III)alamin, as would be expected if molecular oxygen were to reoxidize cob(II) alamin to cob(III)alamin. Aerobic photolysis under the same conditions shows the expected decrease in absorbance at 374 nm but no change at 520 nm. This difference suggests that HO. is able to displace the alkyl ligand from $Co^{III}$, but other HO. reactions also occur (perhaps through the secondary products HOO. and $.O_2^-$) to oxidize the corrin ring. Similar absorbance spectra are obtained from sonolysis of an aerated aqueous solution containing 100 mM phosphate buffer.

A similar result is seen in the reaction of $CH_3$—$Cbl^{III}$ with H. and HO. when these radical species are generated by pulse radiolysis (Blackburn et al., 1972). Reducing species H. reacts to produce the same spectral changes as shown in FIG. 3A. Multiple oxidizing species (HOO. and $.O_2$) can react with $CH_3$—$Cbl^{III}$ to cleave the Co—C bond, but these species also lead to the irreversible degradation of the corrin ring, as evidenced by the spectral changes similar to those seen in FIG. 3B. A precedent for irreversible oxidation of the corrin ring exists in the photooxygenolysis of alkylcobalamins by singlet oxygen (Krautler and Stepanek, 1985).

Aerobic sonolysis of solutions containing 100 mM Hepes or 100 mM t-butyl alcohol produces no change in the absorption spectra over comparable time. This is because molecular oxygen quenches the H. reaction pathway, and t-butyl alcohol quenches the HO. reaction pathway. Although Hepes has not previously been reported to be a scavenger of HO. many reports indicate that organic solute molecules such as formate, can inhibit the reaction of HO. (Weissler, 1962). The absence of any spectral changes under these conditions suggests that direct sonolysis of the Co—C bond is not an important reaction pathway.

EXAMPLE 3

Biological Testing Against NCI Human Tumor Cell Lines

The efficacy of the bioconjugates is tested against tumor cell lines using existing protocols for assessing the effectiveness of targeted coenzyme $B_{12}$ antineoplastic agent-containing bioconjugates. Representative cell lines tested include HCT 116 (human colon tumor), A549 (human lung), ACHN (human kidney), MCF7 (human breast), human prostate, SK5-mel (human melanoma), KB (human nasopharyngeal), CCRF-CEM (human T-cell leukemia), HL-60 (human promyelocytic leukemia), RD-995 (mouse fibrosarcoma), B-16 (mouse melanoma) and Meth-A (mouse carcinoma). Drug screening is carried out with a calorimetric cell viability assay in a 96-well plate.

Additionally, selected bioconjugates are radiolabeled with $^{14}C$ or $^3H$ to assess the level of uptake by human tumor cells. As noted above, the prior art reports that some tumor and leukemia cells produce high levels of $B_{12}$ binding proteins in the serum and sequester $B_{12}$ in high concentrations of up to 50 fold.

Tumor Cell Line Testing Protocol: The drug bioconjugates, synthesized under procedures described herein or adaptions thereof, are diluted over 5 orders of magnitude (approximately 0.005 to 50 μg/mL). Four hours after seeding of the cell in the plate, the cells are treated with the appropriate drug dissolved in isotonic buffered solution. In control experiments, without photolysis triggered drug release, the drug is left on the cells for three days, as in the normal basic cancer screen. In the wells for triggered drug release, the laser output is focused on selected wells for varying times and with varying intensity. Alternatively, a matrix of light-emitting diodes (LEDs) is used. The cells are incubated under standard mammalian tissue culture conditions under the proper $CO_2$ balanced atmosphere. After three days, the cells are re-fed and the colorimetric dye 3-[4,5-dimethylthiazol-2-yl]-2,5-diphenyltetrazolium bromide (MTT) is added. The reduction of the MTT to purple formazan product is quantified in a 96 well plate reader. The concentration of the purple formazan dye is correlated with the number of viable cells. The reduction in cell survival at a given dose rate and photolysis exposure give a quantitative estimation of cell death and drug delivery effectiveness. Care is taken not to expose portions of the plate to photolysis conditions through adventitious spillover of radiation. This is accomplished by using 96 well plates with an opaque mask (Fisher cat#07-200-565) for photolysis.

Uptake of Drug-$B_{12}$ and Drug-Co[SALEN] Bioconjugates: The uptake of drug-$B_{12}$ and drug-Co[SALEN] bioconjugates by cultured tumor cells is monitored by radiolabeling the drug or cobalamin during synthesis. $^3H$-Labeled 5-fluorouracil, methotrexate and chlorambucil are purchased from DuPont/NEN (New England Nuclear). These drug bioconjugates, as well as $^{14}C$-labeled methylcob(III)alamin (synthesized from Cob(I)alamin and $^{14}CH_3I$ ) provide an indication of receptor-mediated uptake by the various tumor cell lines. In this study, the cells are exposed to the radiolabeled drug as described in the preceding section, except no MTT is added at the end of the three-day incubation period. Since all of the cell lines except the leukemia cells grow while attached to the bottom of the microtiter plate well, the growth medium is aspirated to remove the unincorporated radiolabeled drug, followed by several washes with fresh medium. The labeled cells are detached from the bottom of the wells and the radioactivity quantified by scintillation counting. Growth of non-attached leukemia cell takes place in round-bottom microtiter plates such that centrifugation sediments the cells and allows washing with fresh growth medium before solubilizing the cells and quantifying the incorporated radiolabeled drug by scintillation counting.

EXAMPLE 4

Synthesis of Co[SALEN]

Synthesis of N,N'-bis(salicylidene)ethylenediamine

To a stirred solution of salicylaldehyde (12.21 g/10.62 mL) in 70° C. ethanol (100 mL) was added ethylenediamine (3.01 g/3.33 mL). A yellow crystalline material immediately formed, and the reaction mixture was allowed to cool to room temperature with stirring. The solution was filtered, and the crystals were washed with cold ethanol. The ethanol layers were combined and reduced to approximately 20 mL and allowed to stand at 0° C. overnight. The resulting crystals were collected by vacuum filtration and washed with water. The collected solids were dried in vacuo to obtain 13.15 g (98%) N,N'-bis(salicylidene)ethylenediamine as yellow platelets with a melting point of 126° C. (literature value (24) 127–128° C.). $^1$H NMR (DMSO-d$_6$) δ8.57 (s 2H, HC=N), 7.42 (d, 2H aromatic, J=7.3 Hz), 7.31 (t, 2H, aromatic, J=9.0 Hz), 6.88 (t, 4H, aromatic, J=8.3, 16.1 Hz), 3.89 (s, 4H, CH$_2$). $^{13}$C NMR (DMSO-d$_6$) δ166.94 (2C, CO), 160.57 (2C, HC+N), 132.38 (2C, aromatic), 131.69 (4C, aromatic), 118.59 (2C, aromatic), 116.51 (2C, aromatic), 58.88 (2C, CH$_2$).

Synthesis of N,N'-bis(salicylidene)ethylenediaminecobalt (II) (Co[SALEN])

To a hot (100° C.) deoxygenated solution of the above product (2.68 g) in dimethylformamide (25 mL) was added via cannula needle an aqueous solution (10 mL) of cobalt (II) acetate tetrahydrate (2.49 g). The red precipitate which formed was collected by vacuum filtration, washed with cold dimethylformamide, and dried in vacuo to obtain 2.6 g (80%) of N,N'-bis-(salicylidene)ethylenediaminocobalt(II) as red crystals.

EXAMPLE 5

Synthesis of Modified Co[SALEN]

The diglycolate ether of Co[SALEN] is prepared as described in Example 4, using the glycolate ether of 2,5-dihydroxybenzaldehyde in place of salicylaldehyde. An unsymmetrically substituted (glycolate ether/amide) complex is prepared as described in Example 4 by using a mixture of the glycolate ether of 2,5-dihydroxybenzaldehyde and 5-aminosalicylaldehyde in place of salicylaldehyde.

EXAMPLE 6

Synthesis of Chlorambucil-Cobalamin Bioconjugates

Synthesis of 1-bromo-2-[4-(4'-[bis-(2-chloroethyl)amino] phenyl)butyroxy]ethane

Twenty-five mL of freshly distilled CH$_2$Cl$_2$, 0.343 g dicyclohexylcarbodiimide (1.66 mmol), 0.305 g 4-dimethylaminopyridine (2.5 mmol), and 0.263 g 4-dimethylamino-pyridinium chloride (1.66 mmol) were added to a flame-dried 50 mL round bottom flask equipped with a stir bar, reflux condenser, and Ar inlet (Boden and Keck, 1985). The solution was purged with argon and brought to reflux. While refluxing, a solution of 0.304 g chlorambucil (1.0 mmol) and 0.125 g 2-bromoethanol (1.0 mmol) in 5 mL CH$_2$Cl$_2$ (purged under argon for 30 min.) was transferred via cannula to the refluxing solution over a period of 30 min. After addition was complete, the reaction mixture was stirred for 2 h at room temperature. Precipitated dicyclohexylurea was removed by filtration and the solution was concentrated by rotary evaporation. The resulting residue was taken up in CH$_2$Cl$_2$, filtered, and purified by flash silica column chromatography. The desired product was eluted using 1:9 ethyl acetate:hexanes (v/v) to give 0.374 g of a yellow oil in 91% yield (ester 2). $^1$H NMR (CDCl$_3$, 300 MHz) d 7.06 (d, 2H, J=8.4 Hz), 6.60 (d, 2H, J=8.7 Hz), 4.35 (t, 2H, J=6.15 Hz), 3.56–3.72 (m, 8H) 3.48 (t, 2H, J=6.15 Hz), 2.56 (t, 2H, J=7.65 Hz), 2.35 (t, 2H, J=7.35 Hz), 1.91 (quintet, 2H, J=7.58 Hz). $^{13}$C NMR (CDCl$_3$, 75 MHz $^1$H decoupled) d 173.05, 144.35, 130.37, 129.75 (2), 112.12 (2), 63.68, 53.55 (2), 40.60 (2), 33.94, 33.41, 29.05, 26.72.

Synthesis of 2-[4-(4'-[bis-(2-chloroethyl)amino]phenyl) butyroxy]ethylcob(III)alamin (3)

Two hundred mg of hydroxocob(III)alamin (0.15 mmol) was dissolved in 10 mL water and purged with Ar while stirring (Brown and Peck, 1988). The exiting gas was conducted in sequence through: (1) a flask containing 0.025 g NaBH$_4$ (0.66 mmol); (2) a flask containing 5 mL H$_2$O; and (3) a flask containing 0.226 g ester 2 (0.55 mmol) in 5 mL CH$_3$OH. After deaerating for 1 h, the water from flask (2) was transferred to flask (1) containing NaBH$_4$ via cannula and swirled to promote dissolution. This solution was transferred via cannula to the aqueous cobalamin solution. Reduction was allowed to proceed for 20 min, after which the chlorambucil bromoethylester was added to the solution. The reaction mixture was allowed to stir for an additional 5 min. and then 0.2 mL acetone was added to destroy the excess borohydride. The solution was concentrated to approximately 2 mL by rotary evaporation and the resulting solution was applied to a 2.5×30 cm column of Amberlite XAD-2 resin. The column was washed with 1 L H$_2$O desalt and the cobalamin was eluted with 50% aqueous acetonitrile (v/v). The eluent was reduced to approximately 2 mL by rotary evaporation and the solution was applied to a 1×40 cm column of SP-Sephadex C25 (Na$^+$ form). Elution with water removed the major red band which was reduced to a minimal volume. Acetone was added until faint turbidity persisted after swirling. The solution was allowed to stand for 1 h at 0° C. and excess acetone was added to promote further crystallization. The crystals were collected by vacuum filtration and dried in vacuo. 3 was obtained as red crystals (122.5 mg) with a yield of 53%. MS (FAB+) calcd for C$_{68}$H$_{112}$N$_{14}$O$_{16}$CoPCl$_2$, 1541; found 1541.

4-[4'-(bis-[2-chloroethyl]amino)phenyl]butyroylcob(III) alamin (4) was synthesized in a similar manner starting with the acid chloride of chlorambucil and reacting it with hydroxocob(III)alamin as above.

Synthesis of 2-[4-(4'-[bis-(2-chloroethyl)amino]phenyl) butyroxy]ethyl-Co[SALEN] and 4-[4'-(bis-[2-chloroethyl] amino)phenyl]butyroyl-Co[SALEN] are synthesized in a similar manner using Co[SALEN] in place of hydroxocob (III)alamin.

Synthesis of 2-[4-(4'-[bis-(2-chloroethyl)amino]phenyl) butyroxy]ethyl-(Co[SALEN]-folate) and 4-[4'-(bis-[2-chloroethyl]amino)phenyl]butyroyl-(Co[SALEN]-folate) are synthesized in a similar manner using Co[SALEN]-folate in place of hydroxocob(III)alamin.

Synthesis of 2-[4-(4'-[bis-(2-chloroethyl)amino]phenyl) butyroxy]ethyl-(green corrinoid) and 4-[4'-(bis-[2- chloroethyl]amino)phenyl]butyroyl-(green corrinoid) are synthesized in a similar manner using $CH_3$—Co(III) corrinoid (prepared by reacting methyliodide with the green corrinoid of Brown et al. (1996) after it had been reduced with $NaBH_4$) in place of hydroxocob(III)alamin.

EXAMPLE 7

Sonolysis of 2-[4(4'-[bis-(2-chloroethyl)amino]phenyl) butyroxy]ethylcob(III)alamin (3)

The products released by exhaustive sonolysis, as described in Example 2, of compound 3 (prepared in Example 6) were isolated by reverse-phase HPLC (Rainin Microsorb C-18). Elution and separation of the sonolysis products were carried out with an increasing gradient of acetonitrile (A) and 0.05 M phosphoric acid (B): initial condition 5% A: 95% B, increased linearly for 10 min to 30% A and 70% B, maintained for 2 min; followed by a linear increase to 70% A and 30% B over 10 min (Rinchik et al., 1993). The solvent was evaporated from each fraction and the products were extracted with $CH_2Cl_2$ and characterized by $^1H$ and $^{13}C$ NMR.

Figure 4A:
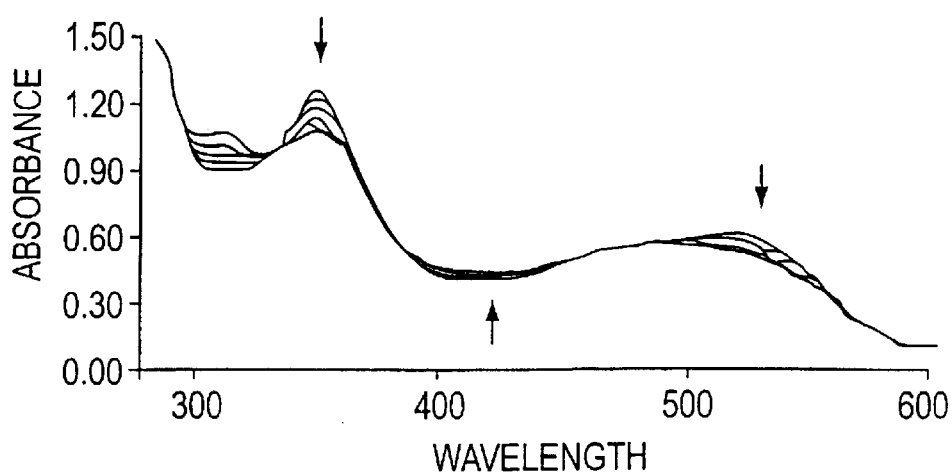
FIG. 4A shows a sequential absorption spectra of aqueous compound 3 (Example 6) as a function of anaerobic sonolysis at pH 7.4, 100 mM Hepes, saturating Ar.

Sequential absorption spectra of aqueous 3 as a function of anaerobic sonolysis at pH 7.4, 100 mM Hepes, saturating Ar, are shown in FIG. 4A. The absorbance at 374 and 520 nm decreases linearly as a function of sonolysis time, and the absorbance at 316 and 420 nm increases linearly, thereby indicating the reaction is zero order in substrate concentration. The isosbestic points at 336, 390, 486 and 585 nm are in agreement with those obtained through anaerobic photolysis of $CH_3$—$Cbl^{III}$. The absorption band at 374 nm is characteristic of a Co—C bond, and its disappearance unambiguously indicates displacement of the axial carbon ligand.

Figure 4B:
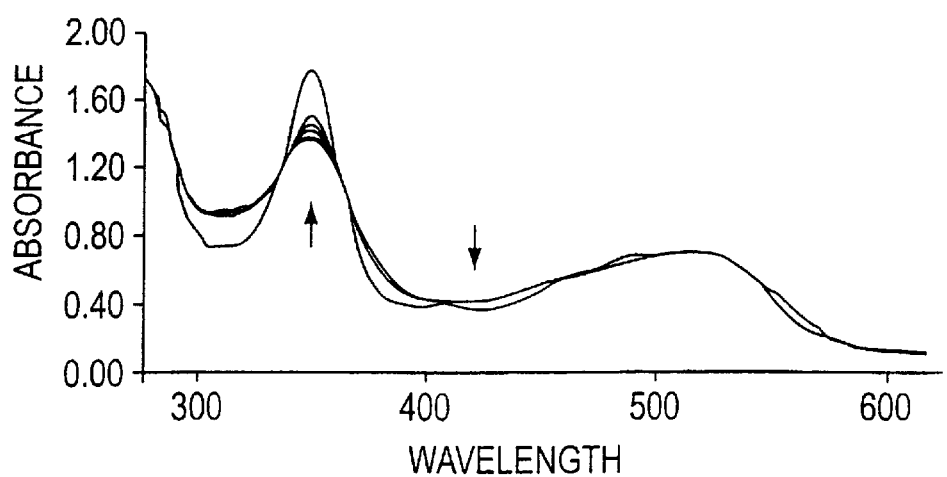
FIG. 4B shows the change in absorbance spectra following aerobic sonolysis of a compound 3 (Example 6) solution containing phosphate buffer.

FIG. 4B shows the change in absorbance spectra following aerobic sonolysis of a 3 solution containing phosphate buffer. Different stable products are obtained under aerobic conditions. Because of the presence of molecular oxygen, the released product was shown by NMR to be 2-[4-(4'-[bis-(2-chloroethyl)amino]phenyl)butyroxy]ethan-1-al. $^1H$ NMR ($CDCl_3$, 300 MHz) 9.59 (s, 1H), 7.08 (d, 2H, J=2.9 Hz), 6.62 (d, 2H, J=2.9 Hz), 4.67 (s, 2H), 3.73–3.59 (m, 8H), 2.60 (t, 2H, J=7.5 Hz), 2.45 (t, 2H, J=7.4 Hz), 1.95 (quintet, 2H, J=7.4); $^{13}C$ NMR ($CDCl_3$, 75 MHz $^1H$ decoupled) 195.85, 173.09, 144.54, 130.43, 129.92 (2), 112.29 (2), 68.73, 53.74 (2), 40.69 (2), 33.99, 33.13, 26.79. The decrease in absorbance at 374 nm is linear with increasing sonolysis time indicating the reaction is zero order in substrate concentration.

The Co—C bond of $CH_3$—$Cbl^{III}$ can be cleaved by sonolysis in aqueous solutions to produce the alkane and cob(II)alamin under anaerobic conditions or to produce the aldehyde and hydroxocob(III)alamin under aerobic conditions. Unlike photolysis and thermolysis that lead to direct Co—C bond cleavage, the predominant pathway for Co—C bond cleavage by sonolysis is through H. mediated reduction of $CH_3$—$Cbl^{III}$ to the labile 19 e-$CH_3$—$Cbl^{II}$-species followed by dissociation to the closed-shell alkane and $Cbl^{II}$, or through the reaction of HO. with $CH_3$—$Cbl^{III}$ that leads to formation of hydroxocob(III)alamin as well as degradation of the corrin ring.

A parallel exists between the reactions of alkylcob(III) alamin under the conditions of sonolysis and pulse radiolysis, (Blackburn et al., 1972) but without the need for expensive equipment. Although the violent cavitation during sonolysis has sufficient energy to break the Co—C bond to produce the {R..$Cbl^{II}$} radical pair by a dissociative pathway analogous to the photolysis of $CH_3$—$Cbl^{III}$, (Endicott and Netzel, 1979; Chagovetz and Grissom, 1993; Natarajan and Grissom, 1996), alkylcob(III)alamins are not sufficiently volatile to be found in the extreme environment of the collapsing bubbles. Therefore, direct Co—C bond cleavage by sonolysis is not possible in spite of the more than 80 kcal/mol difference in bond-dissociation energy between Co—C and H—OH.

Anaerobic sonolysis of the Co—C bond is irreversible because a closed-shell alkane is formed. Under aerobic conditions, the rate of H. reaction with $O_2$ is on the same order of magnitude as the reaction of H. with $CH_3$, thereby suggesting the closed-shell alkane, $CH_4$, should be one of the end products of $CH_3$—$Cbl^{III}$ sonolysis (Buxton et al., 1988; Baulch et al., 1992). In contrast, Co—C bond cleavage of $CH_3$—$Cbl^{III}$, via anaerobic photolysis, is reversible from the {$CH_3$..$Cbl^{II}$} radical pair.

In summary, the ability to form cob(II)alamin and the closed-shell alkane without the use of chemical reductants and without the use of electrochemical, photochemical, or pulse radiolysis equipment may be a useful method to promote activation of drug-cobalamin complexes in vivo.

EXAMPLE 8

Materials and Methods for in vitro Assays of Bioconjugate Activity

Media Preparation

All media were purchased from Sigma and materials used to supplement the media were purchased from Atlanta Biologicals. The HL-60 cell culture was grown in an α-MEM media. The media was completed prior to inoculation by the addition of reagents to bring the final media concentration to 7.5% w/v sodium bicarbonate, 10% fetal calf serum, 100 ug/mL, penicillin and streptomycin, and 50 units/mL mystatin. McCoy's media, with sodium bicarbonate buffer, was used for HCT-116 cell culture. It was completed in the same manner with 8% newborn calf serum and 2% fetal calf serum. Completed media could be stored at 4° C. for several weeks. The culture medium was warmed to 37° C. before inoculation with cells.

Stock Culture Preparation and Maintenance

Stock cell cultures were started from ATCC cell lines. The original ATCC cell line was aliquoted in 10% DMSO and stored in liquid nitrogen. Stock cultures of 40 mL were grown and maintained in collagen-treated, sterile 75 mL culture flasks purchased from Corning. The cultures were incubated at 37° C. in a 5% $CO_2$ environment to maintain a pH of 7.1. Humidity within the incubator was maintained to prevent hypertonicity in the media by placing an open pan of water in the bottom of the incubator.

The concentration of cells within the stock culture was controlled and cell concentrations were estimated in several ways. The media became more purple and subsequently orange as a result of cell metabolism and metabolic byproducts that accumulated in the media. The cells were also visually observed under microscope at 40x and 100x power. Normal HCT-116 cells appeared rounded, flat, and adhered strongly to the walls of the culture flask. When the cells almost covered the bottom of the flask, the cell concentration was reduced. Normal HL-60 cells appeared round, but were well differentiated and easily suspended in the media. Changes in cell morphology were often indicative of bacterial or fungal contamination. For the accurate determination of cell concentrations, a Coulter Cell Counter™ was employed. Stock cultures were not allowed to grow to greater than 100,000 cells/mL. Both of the cell lines were observed to have a doubling time of about 24 hrs.

Assay Preparation

The assays were performed in collagen-treated, sterile 96-well plates that were purchased from Corning. HL-60 cells were grown in round-bottomed wells (Corning catalog #25850) and HCT-116 cells were grown in flat-bottomed wells (Corning catalog #25860). Cell concentrations were measured by a Coulter Cell Counter™. Cells were diluted in bulk and loaded onto the plates with 200 $\mu$L in each well. The assays were performed using approximately 25,000 HL-60 cells/well and 40,000 HCT-116 cells/well.

Since HL-60 cells grow in suspension, the cell concentration was measured and diluted directly. HCT-116 cells, however, adhere to the walls of the flask and must be suspended by treatment with trypsin. A 0.025 mg/mL trypsin solution was thawed immediately before use. The bulk culture medium was removed by aspiration and 2 mL of the cold trypsin solution were added to the flask. The flask was agitated periodically to promote suspension of the cells. Care was taken to limit cell exposure to the trypsin solution to less than five minutes, since prolonged exposure will damage the cell membrane. When the cells were suspended, as observed by a microscope, 8 mL of media were added to inactivate the trypsin. The cell concentration in the resulting suspension was measured, the suspension diluted appropriately, and loaded onto the 96-well plates. Once on the plates, the cells were allowed to adhere for 3 hrs before treatment with 5FU or one of the derivatives.

Cell Growth and MTT Determination of Cell Viability

HL-60 cells were treated and placed in the incubator for 24 hrs. The plates were centrifuged and the supernatant was carefully aspirated without disturbing the cell pellet. A 200 $\mu$L aliquot of media was added immediately. The cells were allowed to grow for 48 hrs. HCT-116 cells were treated and allowed to grow undisturbed for 72 hrs. The culture medium was removed by aspiration (after centrifugation in the case of HL-60 cells). 100 mL of McCoy's media and 11 $\mu$L MTT dye were added. The cells were incubated at 37° C. for 3 hrs. During this time, viable cells reduce the MTT dye to purple formazan by the action of alcohol dehydrogenase. The cells were lysed by the addition of 100 $\mu$L of a solution 1.2M Hcl in 60% ethanol, thereby releasing the reduced dye into solution. The absorbance at 405 nm was measured for each well using a BIO-RAD Microplate Reader (Model 450)™/

EXAMPLE 9

In Vitro Activity of Chlorambucil-Cobalamin Bioconjugates

Thermal Stability of Bioconjugates in Media

It was noted that the chlorambucil bioconjugates 3 and 4 (prepared in Example 6) have thermal lability. Thus, they are expected to thermally decompose during the assay, perhaps before entering the cells or before release by photolysis. Thermal decomposition of both bioconjugates was monitored by a UV-vis diode array spectrophotometer (HP8452) at 37° C. in water, cell-free media, and filtered media in which HCT-116 cells had been grown to a concentration of about 100,000 cells/mL. Spectra were taken hourly for a total of 8 hrs. The presence of intact bioconjugate was then determined by photolysis, 20 min, with a high-pressure mercury lamp. If photolysis had no effect on the spectrum, all of the bioconjugate was assumed to have decomposed.

In Vitro Assays of 3 and 4 Activity

Both bioconjugates were assayed against HCT-116, HL-60, B-16, Meth-A, and RD-995 cell lines. The assays were performed in the same manner as described in Example 8 as modified herein. The B-16, RD-995 and Meth-A cells lines are all Balb/c derived carcinoma lines which were provided by Dr. R. Daynes of the University of Utah. These cell lines were grown in RPMI media which was completed with 5% fetal bovine serum and other media components as previously described. Both the B-16 and RD-995 cell lines were suspended in trypsin, as in the case of HCT-116 cells. The Meth-A cells loosely adhere to the walls of the flask and grow both attached to the flask and suspended in solution. These cells could be completely suspended by successive washing of the flask wall with media.

Assays were performed at cell concentrations of about 40,000 cells per well, with the exception of the HL-60 assay which was performed at 25,000 cell per well. The HCT-116, B-16 and RD-995 cells were assayed in flat bottomed, 96-well plates, while the HL-60 and Meth-A cells were assayed in round bottomed plates. Chlorambucil, unconjugated, was tested prior to the bioconjugates. The cells were treated with the bioconjugates in both non-photolytic and photolytic conditions. The cells were incubated for three days (media was aspirated and replaced after 24 h. in the case of the HL-60 cells) and the resulting viability measured by an MTT assay.

The MTT assay was somewhat altered for this experiment. The culture medium was aspirated after 72 hrs. The Meth-A and HL-60 cells were centrifuged prior to aspiration. Then, 100 $\mu$L of McCoy's media and 11 $\mu$L of the MTT solution were added as before. At the end of 4 hours, the culture medium was aspirated a second time (following centrifugation in the case of HL-60 and Meth-A cells) and 100 $\mu$L of DMSO was added. The DMSO lysed the cells releasing the MTT dye into solution. The absorbance of each well at 450 nm was measured as before. The HCl/ethanol solution previously used has a tendency to precipitate proteins from the resulting solution, which may give falsely increased absorbance measurements. The replacement of DMSO avoids this problem.

The concentration of chlorambucil and the bioconjugates were varied from 0.04 $\mu$M to 400 $\mu$M within the assay. The cells were treated with the bioconjugates under dim, red lights to avoid photolysis. Non-photolytic conditions were maintained by wrapping the 96 well plates with foil during the incubation periods. Photolysis was performed in black plates with flat, clear bottomed wells (Costar catalog number: 3603). These plates are sterile, collagen treated, and made of optically clear plastic. Growth of the cells in these plates did not show any differences to those grown in the normal clear plastic plates. Photolysis was achieved by an array of high intensity green LEDs (Hewlett Packard catalog number: 782-6124). The array was constructed from one of the black plates in which one LED was placed in each well. The LEDs could be turned on and off as vertical rows. In each assay, two rows of cells were left untreated as growth controls. One of these rows was not photolyzed by the LEDs to demonstrate any unexpected effects of photolysis; irradiation did not demonstrate any effects on the untreated control cells. An empty plate was placed between the array and the assay plate to avoid heating the cells. Ten minutes of irradiation produced complete photolysis for the bioconjugate in cell-free media. The cells were irradiated for 10 min during the assay. The time of irradiation, following treatment with drug, was determined by a timecourse assay. The entire plate was treated with one of the bioconjugates at a concentration equal to the $IC_{50}$ of chlorambucil in that cell line. The rows were irradiated separately one half hour after treatment and then hourly.

Irradiation at 1 h after treatment demonstrated the greatest bioconjugate activity in all of the cell lines. Further assays were performed with irradiation one hour after treatment. In the case of the Meth-A cell line, the cells were transferred from the round-bottomed plate into the black plate for photolysis and then returned to the round bottomed plate.

The HL-60 cell line could not be tested under these photolytic conditions.

Results and Discussion

Both bioconjugates show significant thermal decomposition in both water and cell free media at 37° C. At the end of 8 hrs, photolysis has no effect on the spectrum, indicating that all of the bioconjugate has decomposed. In the HCT-116 cell media both bioconjugates show fast initial decomposition and are significantly stabilized at subsequent time. Haptocorrin, a cobalamin binding protein is known to stabilize alkylcobalamins by several orders of magnitude. This protein is present in the cell-free media from the added bovine serum. However, most of this protein in serum is saturated with cobalamin, so binding to the bioconjugates may be inhibited. It is known that several types of tumor cells secrete high amounts of cobalamin binding proteins, especially haptocorrin. Thus, media in which cells have been growing has a higher concentration of apo-haptocorrin. The initial fast decomposition of the bioconjugates represents the amount remaining after the saturation of haptocorrin in the media. The bound bioconjugates are significantly stabilized by haptocorrin and the haptocorrin complex associates and dissociates in a dynamic fashion in solution, especially in the presence of significant concentrations of other cobalamins in the media. Thus, the bioconjugates are still susceptible to decomposition when not bound to haptocorrin. While haptocorrin does stabilize the bioconjugates by several orders of magnitude, slow decomposition is still seen during the assay. However, this assay does indicate that the bioconjugates are stabilized such that a significant amount is still intact during the time of uptake and photolysis.

Figure 5:
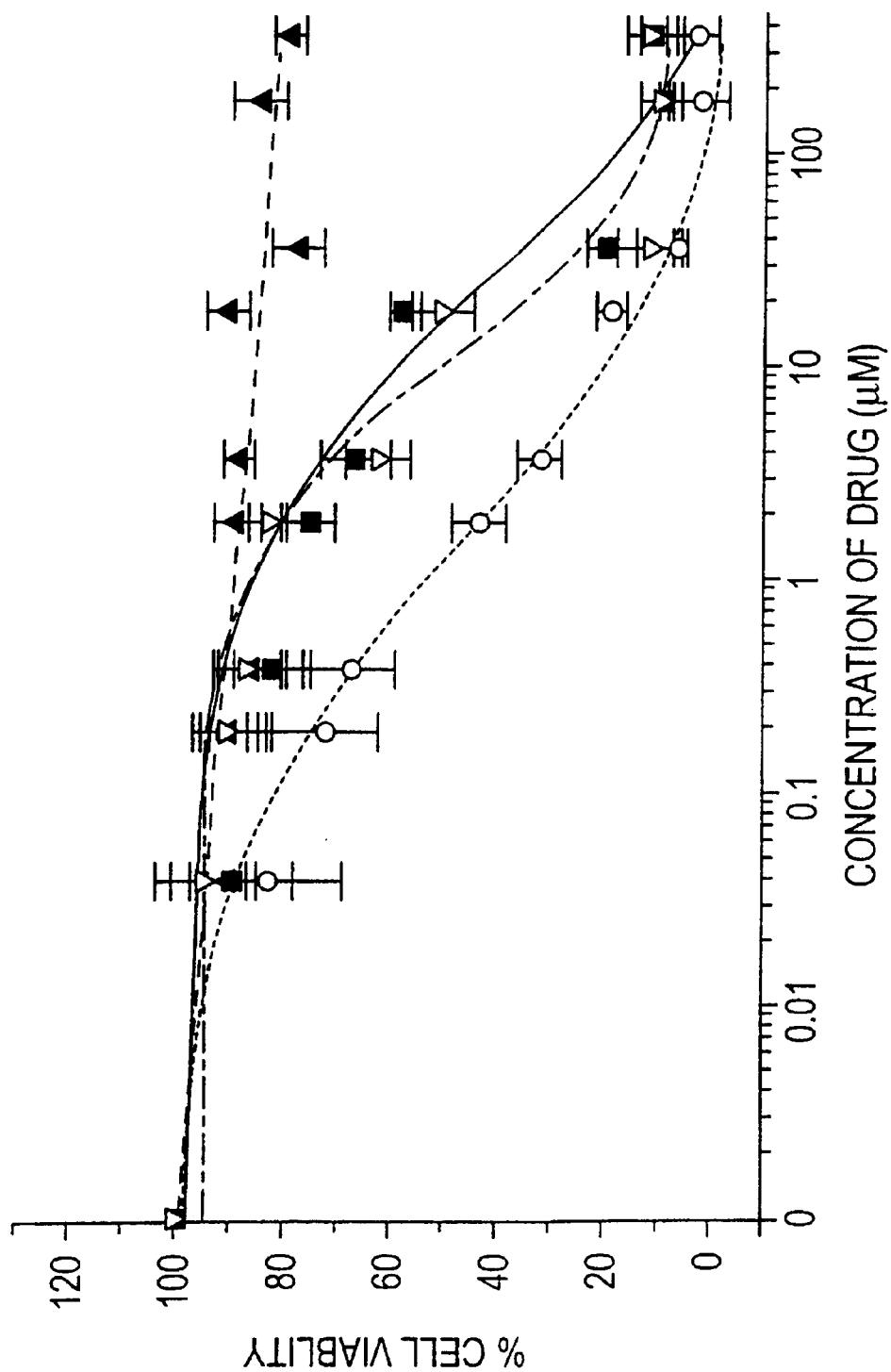
FIG. 5 shows the effect of a chlorambucil bioconjugate on cell viability for the HCT-116 cell line. The results are shown for chlorambucil (■), the chlorambucil bioconjugate with photolysis (○), the chlorambucil bioconjugate with no photolysis (▲) and the chlorambucil bioconjugate plus 10 equivalents of hydroxycobalamin with photolysis (▽).

The data from the photolysis timecourse and activity assays are summarized in FIGS. 5–9 for compound 3 in each of the cell lines tested. Similar results were seen for compound 4. In general, both bioconjugates showed similar uptake and photolysis behavior in the photolysis timecourse assay. The maximal photolytically induced toxicity is seen one hour after treatment with either of the bioconjugates. In all cases, photolysis of the bioconjugate demonstrated increased toxicity over that of unconjugated chlorambucil. FIG. 5 shows that the chemotherapeutic drug, chlorambucil, has an $LD_{50}$ of about 2 $\mu$M with respect to the HCT-116 cell line, whereas the bioconjugate shows no substantial toxicity at concentrations approaching 100 $\mu$M. If cells treated with the bioconjugate are subjected to brief irradiation with red light 12 hours after dosing, the $LD_{50}$ decreases by a factor of 25 to 0.08 $\mu$M. If a 10-fold excess of vitamin $B_{12}$ is added to saturate the cell surface receptors, the bioconjugate is not taken into the cells and photolysis triggers release of the active chlorambucil in the cell culture medium. The released chlorambucil now enters the cell by passive diffusion and an $LD_{50}$ of 2 $\mu$M is observed in close agreement with the value for chlorambucil standard.

Figure 6:
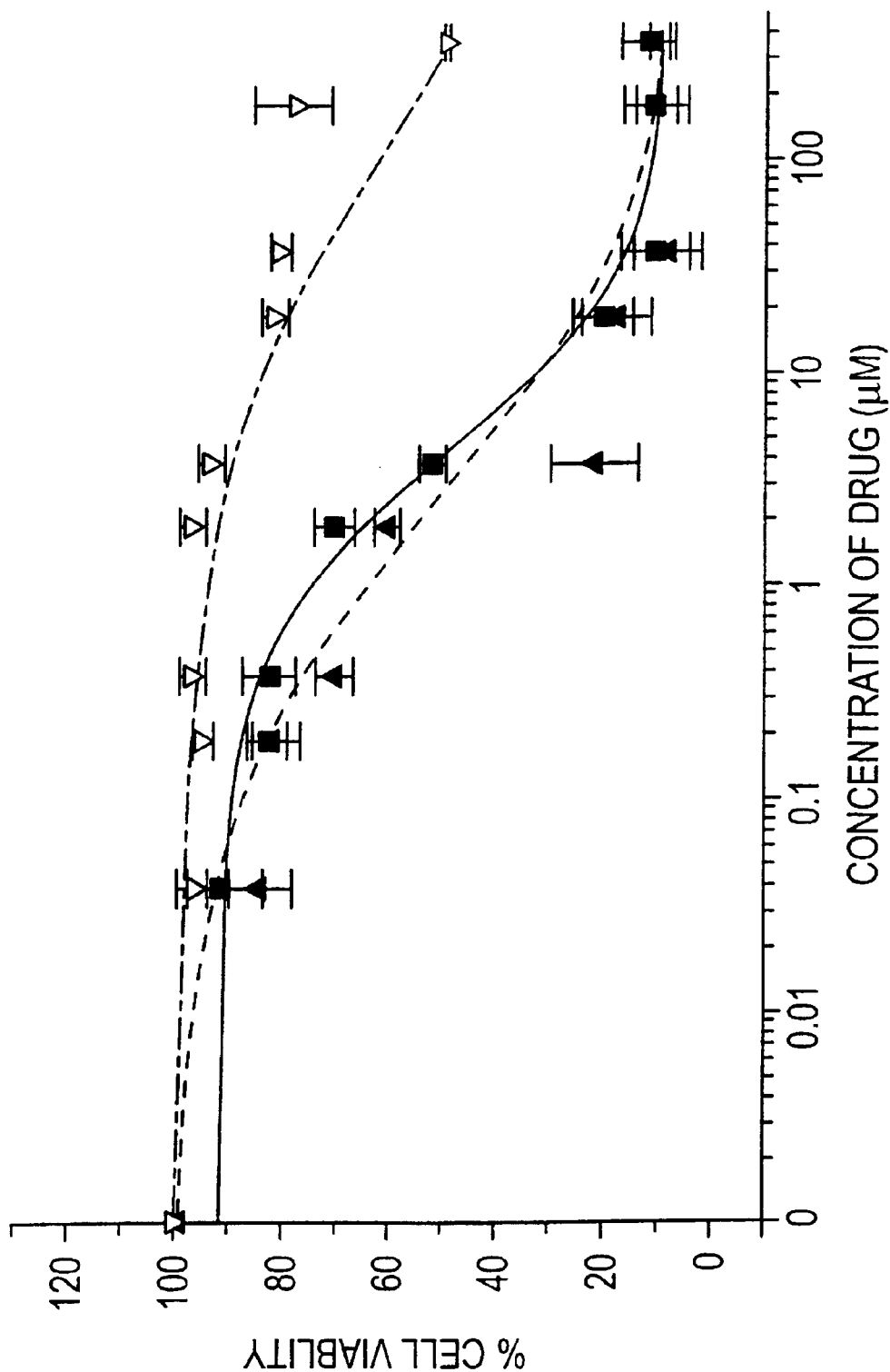
FIG. 6 shows the effect of a chlorambucil bioconjugate on cell viability for the HL-60 cell line. The results are shown for chlorambucil (■), the chlorambucil bioconjugate with no photolysis (▲) and the chlorambucil bioconjugate plus 10 equivalents of hydroxycobalamin with no photolysis (▽).
Figure 7:
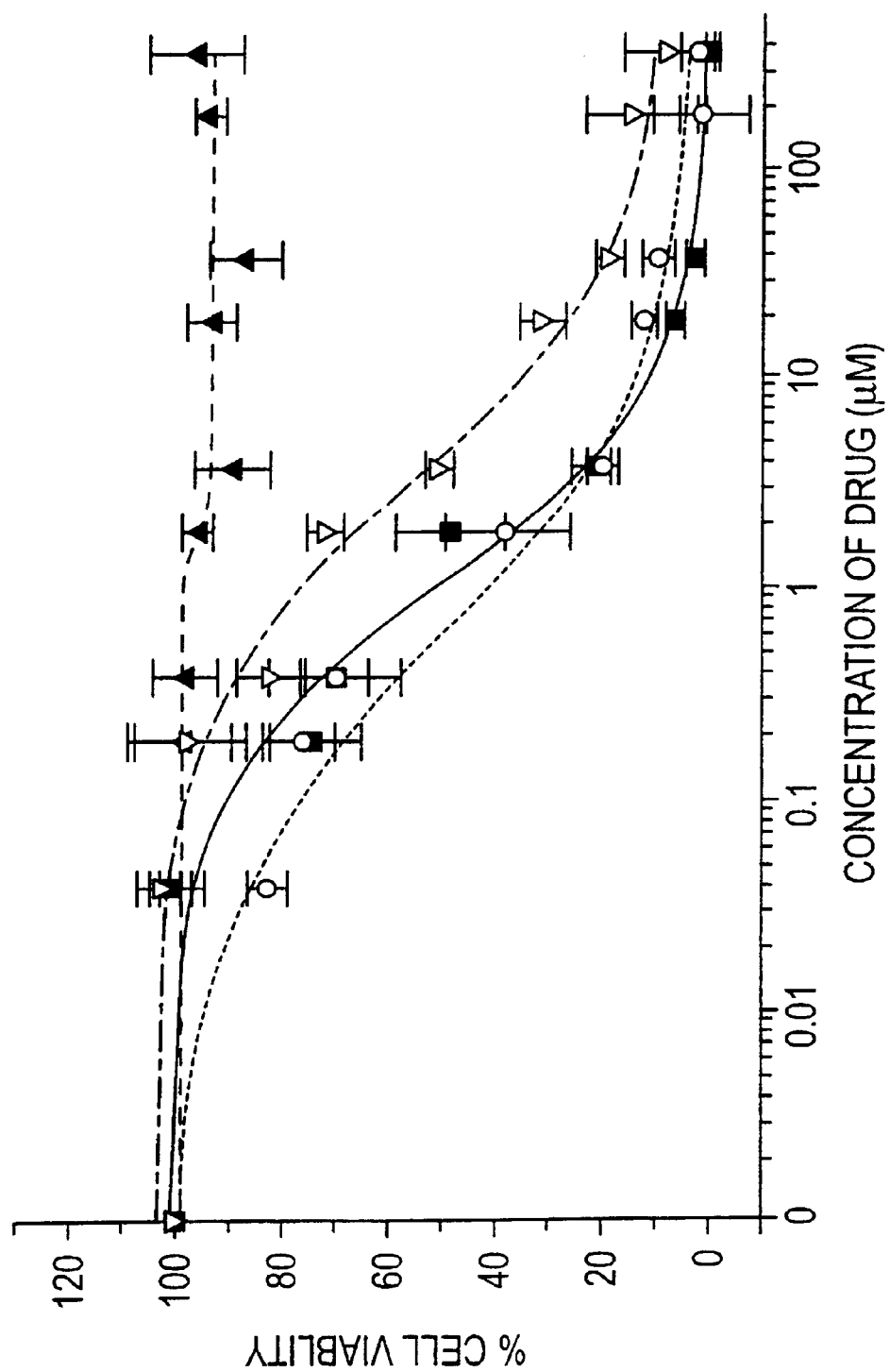
FIG. 7 shows the effect of a chlorambucil bioconjugate on cell viability for the B-16 cell line. The results are shown for chlorambucil (■), the chlorambucil bioconjugate with photolysis (○), the chlorambucil bioconjugate with no photolysis (▲) and the chlorambucil bioconjugate plus 10 equivalents of hydroxycobalamin with photolysis (▽).
Figure 8:
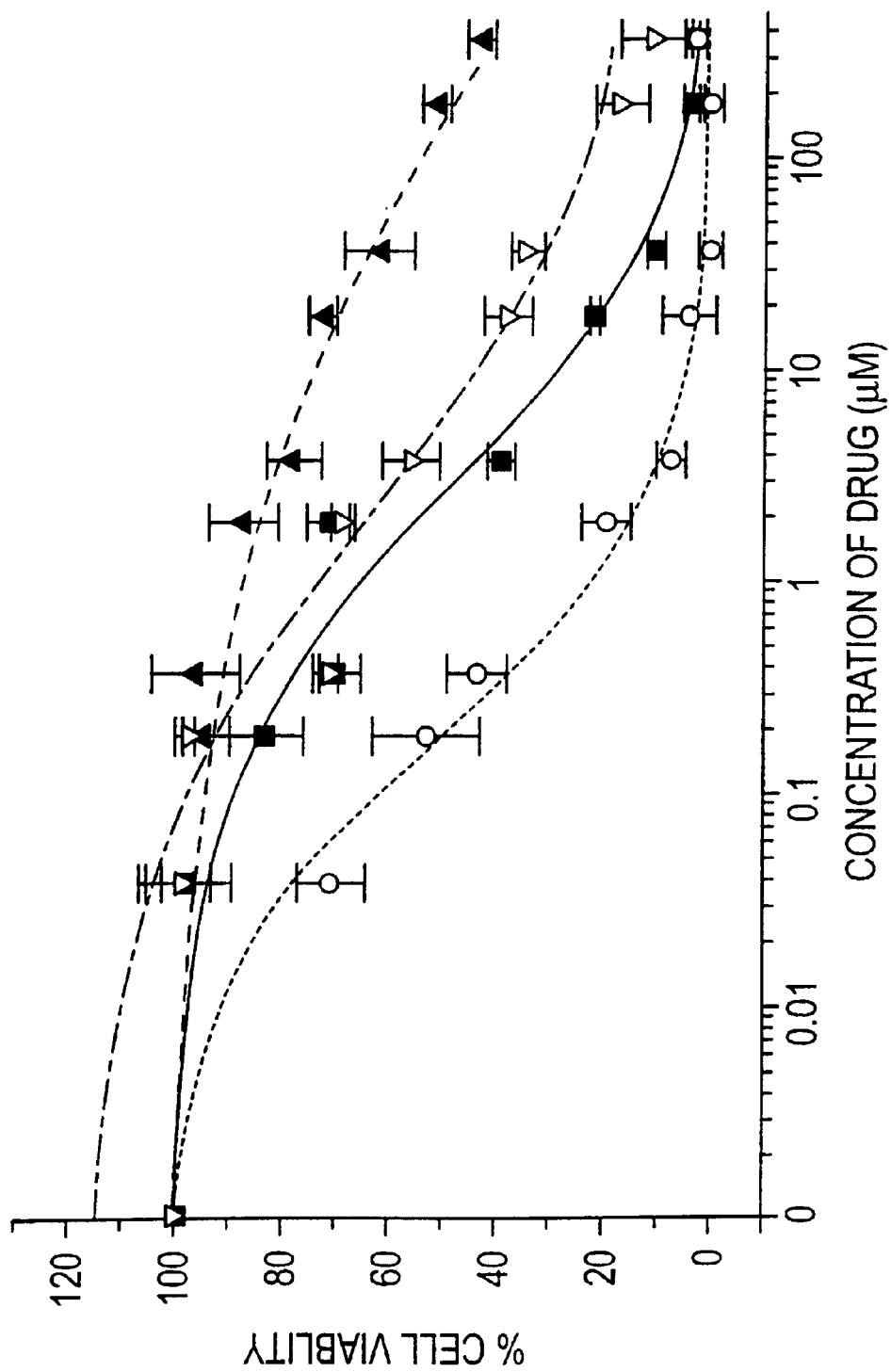
FIG. 8 shows the effect of a chlorambucil bioconjugate on cell viability for the Meth-A cell line. The results are shown for chlorambucil (■), the chlorambucil bioconjugate with photolysis (○), the chlorambucil bioconjugate with no photolysis (▲) and the chlorambucil bioconjugate plus 10 equivalents of hydroxycobalamin with photolysis (▽).
Figure 9:
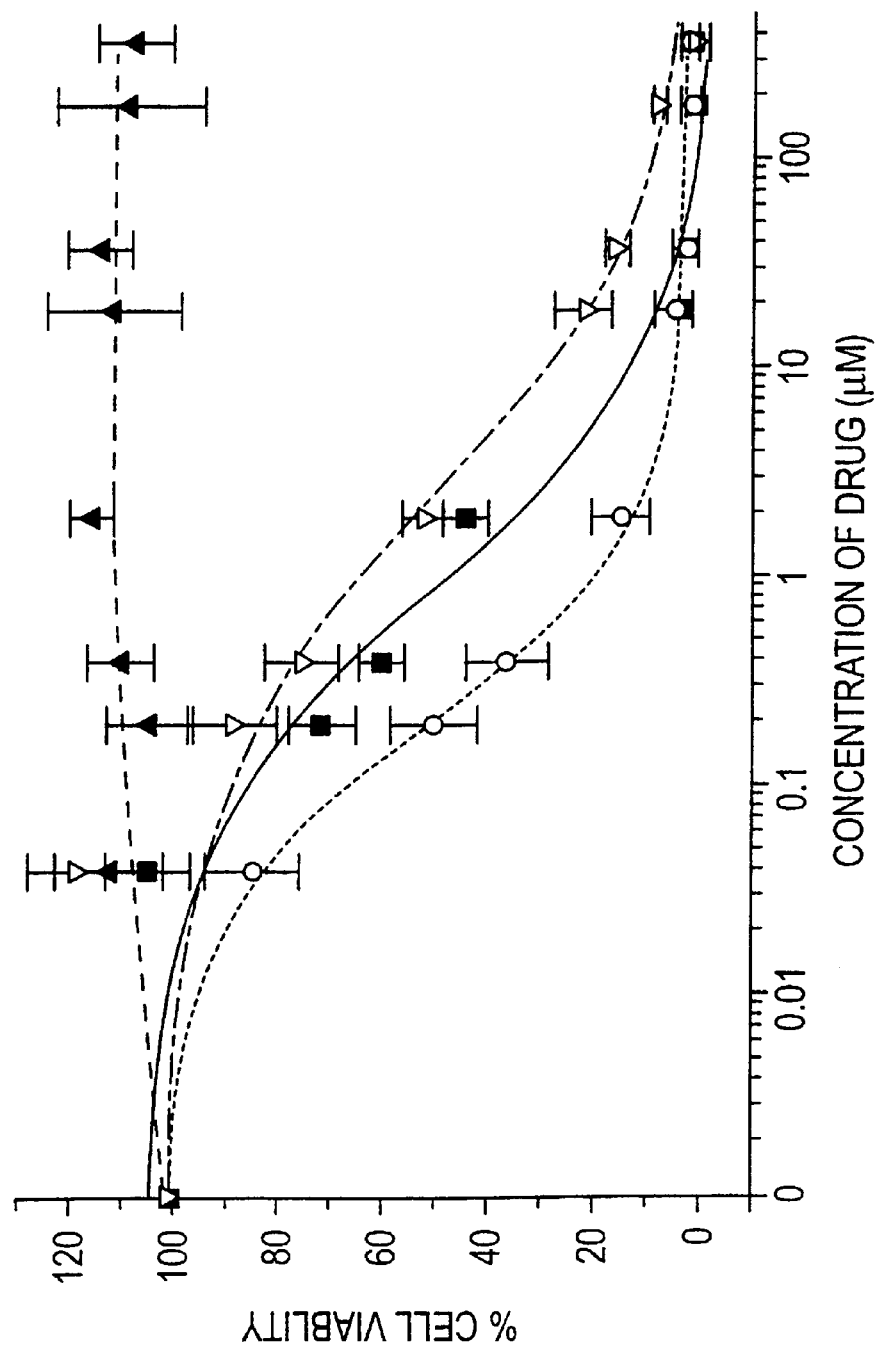
FIG. 9 shows the effect of a chlorambucil bioconjugate on cell viability for the RD-995 cell line. The results are shown for chlorambucil (■), the chlorambucil bioconjugate with photolysis (○), the chlorambucil bioconjugate with no photolysis (▲) and the chlorambucil bioconjugate plus 10 equivalents of hydroxycobalamin with photolysis (▽).

FIG. 6 shows that in cell line HL-60, the unconjugated chlorambucil standard exhibits an $LD_{50}$ of 0.5 $\mu$M, but the bioconjugate is at least 2-fold better with an $LD_{50}$ of 0.2 $\mu$M. The cytotoxicity of MC-121 against the leukemia cell line is still a dramatic result when compared with the absence of toxicity when the cellular uptake of the conjugate is outcompeted by the addition of 10 equivalents of vitamin $B_{12}$. Similar results were obtained with Meth-A cells. The HL-60 and Meth-A cells have a high turnover rate, and in the case of Meth-A divide more rapidly than the other cell lines. These cells may, in fact, metabolize cobalamin at a faster rate than the other cell lines and thus release the chlorambucil in significant concentrations without photolysis. In order for this to be practical, however, cobalamin metabolism must occur before significant hydrolysis of chlorambucil moiety. It is reported that HL-60 cells are able to convert vitamin $B_{12}$ into the other cobalamin forms efficiently (more quickly than normal lymphocytes) (Quadros and Jacobsen, 1995) and thus, would be able to efficiently release the conjugated chlorambucil. In the other cell lines, however, the bioconjugates are essentially not toxic in non-photolytic conditions, which is a promising indication that these bioconjugates may not be toxic in normal somatic cells or healthy hematopoetic cells. $IC_{50}$ values of the bioconjugates in both non-photolytic and photolytic conditions are summarized in Table 1.

TABLE 1

| | $IC_{50}$ values ($\mu$M) | | | | |
|---|---|---|---|---|---|
| Cell Line | HCT-116 | HL-60 | B-16 | Meth-A | Rd-995 |
| Chlorambucil Photolysis | 20.8 | 5.8 | 1.4 | 1.8 | 1.1 |
| 3 | 1.7 | — | 0.6 | 0.2 | 0.2 |
| 4 | 1.1 | — | 0.3 | 0.3 | 0.3 |
| No Photolysis | | | | | |
| 3 | — | 3.2 | — | 210.1 | — |
| 4 | — | 8.9 | — | 84.2 | — |

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

List of References

Allen, R. H. and Majerus, P. W. (1972a). *J. Biol. Chem.* 247:7695–7701.

Allen, R. H. and Majerus, P. W. (1972b). *J. Biol. Chem.* 247:7709–7717.

Baulch, D. L., et al., (1992). *J. Phys. Chem. Ref. Data* 21:411.

Bennett, C. F., et al. (1992). *Mol. Pharmacol.* 41:1023–1033.

Blackburn, R., et al. (1972). *J. Chem. Soc. Faraday I,* 1687.

Boden, E. F. and Keck, G. E. (1985). *J. Org. Chem.* 50:2394.

Brown, K. L. and Peck, S. (1988). *Organomat. Syn.* 4:304.

Brown et al. (1996). *J. Inorg. Chem.* 35:3442.

Bunnell, B. A., et al. (1992). *Somatic Cell Mol. Genet.* 18:559–569.

Buxton, G. V., et al., (1988). *J. Phys. Chem. Ref. Data* 17:513.

Carmel (1975). *New Engl. J Med.* 292:282–284.

Castle, W. B. (1953). *N. Engl. J. Med.* 24:603–611.

Chagovetz, A. M. and Grissom, C. B. (1993). *J. Am. Chem. Soc.* 115:12152.

Chang, E. H. and Miller, P. S. (1991). In *Prospects for Antisense Nucleic Acid Therapy of Cancer and AIDS*, ed. Wickstrom, E., Wiley-Liss, New York, pp. 115–124.

Chen and Chance (1993). *Biochem.* 32:1480–1487.

Cohen, J. S. and Hogan, M. E. (1994). *Sci. Am.* 76–82.

Cooney, M., et al. (1988). *Science* 241:456–459.

Endicott, J. F. and Netzel, T. L. (1979). *J. Am. Chem. Soc.* 101:4000.

Fornari, F. A., et al. (1996). *Biochem. Pharmacol.* 51:931–940.

Fox, H. J. and Castle, W. B. (??). *Am. J. Med. Sci.* 203:18–26.

Fritzer, M., et al. (1996). *Biochem. Pharmacol.* 51:489–493.
Gao, X. and Huang, L. (1991). *Biochem. Biophys. Res. Commun.* 179:280–285.
Gasparro (1986). *Biochem. Biophys. Res. Commun.* 141:502–509.
Ginobbi, P., et al. (1997). *Anticancer Res.* 17:29–36.
Grissom, C. B. (1995). *Chem. Rev.* 95:3–25.
Hosada, J., et al. (1995). *Biol. Pharm. Bull.* 18:1234–1237.
Howard, W. A., et al. (1997). *Bioconj. Chem.* 8:498–502.
Hu, Y.-P., et al. (1996). *Cancer Chemother. Pharmacol.* 37,556–560.
Johnson, D. A., et al. (1995). *Anticancer Res.* 15:1387–1394.
Kabanov, A. V., et al. (1995). *Bioconjugate Chem.* 6:639–643.
Krautler, B. and Stepanek, R (1985). *Angew. Chem. Int. Ed. Engl.* 24:62.
Kumar et al. (1987). *J. Biol. Chem.* 262:7171–7179.
Le Doan, T., et al. (1987). *Nucl. Acids Res.* 15:7749–7760.
Letsinger, R. L. (1993). *Nucl. Acids Symp. Ser.* 29:1–2.
Ling, Y.-L., et al. (1996). *Mol. Pharmacol.* 49:832–841.
Longman, S. A., et al. (1995). *Cancer Chemother. Pharmacol.* 36:91–101.
Lott et al., (1995). *J. Am. Chem. Soc.* 117:12194–12201.
Low, P. S. et al. (1995). U.S. Pat. No. 5,416,016.
Ma, D. D. F. and Wei A-Q. (1996). *Leukemia Res.* 20:925–930.
Madon, J. and Blum, H. E. (1996). *Hepatology* 24:474–481.
Mason, T. J. (1991). *Practical Sonochemistry: Users Guide to Applications in Chemistry and Chemical Engineering* Horwood, N.Y.
Merwin, J. R., et al. (1994). *Bioconjugate Chem.* 5:612–620.
Moser, H. E. and Dervan, P. B. (1987). *Science* 238:645–650.
Murray, G. J. and Neville, D. M. (1980). *J. Biol. Chem.* 255:11942–11948.
Myers (1988). European Patent Application 86810614.7
Natarajan, E. and Grissom, C. B. (1996). *Photochem. Photobiol.* 64:286.
Nichols, J., et al. (1997). *Eur. J. Cancer* 33 Suppl. 1:S34–S36
Oeltmann and Heath (1979). *J. Biol. Chem.* 254:1028.
Postel, E. H. (1992). *Ann. N.Y. Acad. Sci.* 660:57–63.
Quadros, E. V. and Jacobsen, D. W. (1995). *Biochim Biophys. Acta.* 1244:395–403.
Rando, R., et al. (1994). *Nucl. Acids Res.* 22:678–685.
Rinchik, E. M., et al. (1993). *Bioessays* 12:831–836.
Roth and Maddox (1983). *J. Cell. Phys.* 115:151
Russell-Jones, G. J. et al. (1995). U.S. Pat. No. 5,428,023.
Sivam, G. P., et al. (1995). *Cancer Res.* 55:2352–2356.
Skoog, J. U. and Maher, L. J., III (1993). *Nucl. Acids Res.* 21:2131–2138.
Stein, C. A. and Cohen, J. S. (1988). *Cancer Res.* 48:2659–2688.
Svensson, H. P., et al. (1995). *Cancer Res.* 55:2357–2365.
Szcylik, C., et al. (1991). *Science* 261:562–565.
Tanaka, T., et al. (1996). *Biol. Pharm. Bull.* 19:774–777.
Trubetskoy, V. S., et al. (1992). *Biochim. Biophys. Acta* 1131:311–313.
Uhlmann, E. and Peyman, A. (1990). *Chem. Rev.* 90:543–584.
Vlassov, V. V., et al. (1994). *Biochim. Biophys. Acta* 1197:95–108.
Wang, S., et al. (1995). *Proc. Natl. Acad. Sci. USA* 92:3318–3322.
Waxman, et al. (1972). *Clin. Res.* ??:572.
Weissler, A. (1962). *Nature* 193:1070.
Wickstrom, E., et al. (1992). *Cancer Res.* 52:6741–6745.
Wu, G. Y. (19887). *J. Biol. Chem.* 262:4429–4432.
Yao, Z., et al. (1996). *J. Viral Hepat.* 3:19–22.
Zon, G. (1993). *Methods Mol. Biol.* 20:165–189.

What is claimed is:

1. A bioconjugate of a bioactive agent and an organocobalt complex wherein the bioactive agent is covalently conjugated to the cobalt atom through a non-reactive atom in the bioactive agent molecule.

2. The bioconjugate of claim 1, wherein said non-reactive atom is selected from the group consisting of a carbon atom, a nitrogen atom, an oxygen atom, a sulfur atom, a selenium atom or a silicon atom.

3. The bioconjugate of claim 1, wherein said non-reactive atom is a carbon atom.

4. The bioconjugate of claim 3, wherein the non-reactive carbon atom is a carbon atom from an alkyl, acyl or aryl group that will not lead to rearrangement or destruction of the bioactive agent under conditions of ligand exchange during receptor-mediated endocytosis.

5. The bioconjugate of claim 1, wherein said bioactive agent is covalently bound directly to the cobalt atom of the organocobalt complex.

6. The bioconjugate of claim 1, wherein said bioactive agent is covalently bound indirectly to the cobalt atom of the organocobalt complex via a spacer.

7. The bioconjugate of claim 6, wherein said spacer is a self-destructing linker.

8. The bioconjugate of claim 1, wherein said bioactive agent is a diagnostic compound.

9. The bioconjugate of claim 1, wherein said bioactive agent is a drug.

10. The bioconjugate of claim 9, wherein said bioactive agent is an anticancer agent.

11. The bioconjugate of claim 1, wherein said organocobalt complex is cobalamin, cobalamin lactone, cobalamin lactam, or a cobalamin derivative, wherein said cobalamin derivative is (a) cobalamin in which the benzimidizaole ring is substituted with a halogen, hydroxy or a $C_{1-6}$ alkyl, (b) an anilide, ethylamide, monocarboxylic acid, dicarboxylic acid, tricarboxylic acid or propionamide derivative of cobalamin, or (c) cobalamin substituted with an amino, a nitro, a halogen, a sulfito, a $C_{2-6}$ alkylene or a $C_{2-6}$ alkyne.

12. The bioconjugate of claim 1, wherein said organocobalt complex is a compound having the following formula:

wherein the R is H, amino, $C_{1-6}$ alcohol, or $C_{1-6}$ carboxyl, W, W', X, X', Y, Y', Z and Z' are independently H, amino, $C_{1-6}$ alcohol, $C_{1-6}$ carboxyl, $SO_3$—, $CH_2OH$, $CO_2H$, or nitro, or W and X together form a 4–6 member cyclic or heterocyclic ring, or W' and X' together form a 4–6member cyclic or heterocyclic ring, or Y and Z together form a 4–6 member cyclic or heterocyclic aromatic ring or Y' and Z' together form a 4–6 member cyclic or heterocyclic aromatic ring.

13. The bioconjugate of claim 12, which further comprises a targeting molecule covalently linked to one of said R, W, W', X, X', Y, Y', Z or Z, wherein said targeting molecule is selected from the group consisting of glucose, galactose, mannose, mannose 6-phosphate, transferrin, cobalamin, asialoglycoprotein, α-2-macroglobulins, insulin, a peptide growth factor, folic acid or derivatives, biotin or derivatives, YEE(GalNAcAH)$_3$ or derivatives, albumin, texaphyrin, metallotexaphyrin, a vitamin, a coenzyme, an antibody, an antibody fragment and a single-chain antibody variable region (scFv).

14. The bioconjugate of claim 1, wherein said organocobalt complex is selected from the group consisting of organo(pyridine)bis(dimethylglyoximato)cobalt, a corrinoid or derivatives thereof, wherein said derivative is (a) a corrinoid in which the benzimidizaole ring is substituted with a halogen, hydroxy or a $C_{1-6}$ alkyl, (b) a corrinoid substituted with an amino, a nitro, a halogen, a sulfito, a $C_{2-6}$ alkylene or a $C_{2-6}$ alkyne, or (c) organo(pyridine)bis(dimethylglyoximato)cobalt substituted with an amino, a nitro, a halogen, a sulfito, a $C_{2-6}$ alkylene or a $C_{2-6}$ alkyne.

15. The bioconjugate of claim 1, wherein said organocobalt complex comprises a multiple unsaturated heterocyclic ring system bonded to a cobalt atom through 4–5-nitrogens and/or chalcogens which are part of said ring system.

16. The bioconjugate of claim 15, wherein said non-reactive atom is selected from the group consisting of a carbon atom, a nitrogen atom, an oxygen atom, a sulfur atom, a selenium atom or a silicon atom.

17. The bioconjugate of claim 15, wherein said non-reactive atom is a carbon atom.

18. The bioconjugate of claim 17, wherein the non-reactive carbon atom is a carbon atom from an alkyl, acyl or aryl group that will not lead to rearrangement or destruction of the bioactive agent under conditions of ligand exchange during receptor-mediated endocytosis.

19. The bioconjugate of claim 15, wherein said bioactive agent is covalently bound directly to the cobalt atom of the organocobalt complex.

20. The bioconjugate of claim 15, wherein said bioactive agent is covalently bound indirectly to the cobalt atom of the organocobalt complex via a spacer.

21. The bioconjugate of claim 20, wherein said spacer is a self-destructing linker.

22. The bioconjugate of claim 15, wherein said bioactive agent is a diagnostic compound.

23. The bioconjugate of claim 15, wherein said bioactive agent is a drug.

24. The bioconjugate of claim 23, wherein said bioactive agent is an anticancer agent.

25. The bioconjugate of claim 15, wherein said organocobalt complex is cobalamin, cobalamin lactone, cobalamin lactam, or a cobalamin derivative, wherein said cobalamin derivative is (a) cobalamin in which the benzimidizaole ring is substituted with a halogen, hydroxy or a $C_{1-6}$ alkyl, (b) an anilide, ethylamide, monocarboxylic acid, dicarboxylic acid, tricarboxylic acid or propionamide derivative of cobalamin, or (c) cobalamin substituted with an amino, a nitro, a halogen, a sulfito, a $C_{2-6}$ alkylene or a $C_{2-6}$ alkyne.

26. The bioconjugate of claim 15, wherein said organocobalt complex is selected from the group consisting of organo(pyridine)bis(dimethylglyoximato)cobalt, a corrinoid or derivatives thereof, wherein said derivative is (a) a corrinoid in which the benzimidizaole ring is substituted with a halogen, hydroxy or a $C_{1-6}$alkyl, (b) a corrinoid substituted with an amino, a nitro, a halogen, a sulfito, a $C_{2-6}$ alkylene or a $C_{2-6}$ alkyne, or (c) organo(pyridine)bis(dimethylglyoximato)cobalt substituted with an amino, a nitro, a halogen, a sulfito, a $C_{2-6}$ alkylene or a $C_{2-6}$ alkyne.

27. The bioconjugate of claim 15, wherein said organocobalt complex is a compound having the following formula:

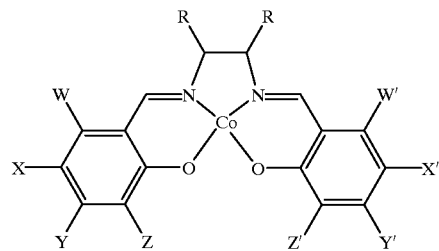

wherein R is H, amino, $C_{1-6}$ alcohol, or $C_{1-6}$ carboxyl, W, W', X, X', Y, Y', Z and Z' are independently H, amino, $C_{1-6}$ alcohol, $C_{1-6}$ carboxyl, $SO_3$—, $CH_2OH$, $CO_2H$, or nitro, or W and X together form a 4–6 member cyclic or heterocyclic ring, or W' and X' together form a 4–6 member cyclic or heterocyclic ring, or Y and Z together form a 4–6 member cyclic or heterocyclic aromatic ring or Y' and Z' together form a 4–6 member cyclic or heterocyclic aromatic ring.

28. The bioconjugate of claim 27, which further comprises a targeting molecule covalently linked to one of said R, W, W', X, X', Y, Y', Z or Z, wherein said targeting molecule is selected from the group consisting of glucose, galactose, mannose, mannose 6-phosphate, transferrin, cobalamin, asialoglycoprotein, α-2-macroglobulins, insulin, a peptide growth factor, folic acid or derivatives, biotin or derivatives, YEE(GalNAcAH)$_3$ or derivatives, albumin, texaphyrin, metallotexaphyrin, a vitamin, a coenzyme, an antibody, an antibody fragment and a single-chain antibody variable region (scFv).

* * * * *